(12) United States Patent
Van Herwijnen et al.

(10) Patent No.: US 11,091,513 B2
(45) Date of Patent: Aug. 17, 2021

(54) TOMATO PLANTS ALLOWING THE ESTABLISHMENT OF MITES

(71) Applicant: RIJK ZWAAN ZAADTEELT EN ZAADHANDEL B.V., De Lier (NL)

(72) Inventors: Zeger Otto Van Herwijnen, De Lier (NL); Dörthe Bettina Dräger, De Lier (NL); Karel Jozef Florent Bolckmans, De Lier (NL); Yvonne Maria Van Houten, De Lier (NL); Jasper De Joode, De Lier (NL)

(73) Assignee: RIJK ZWAAN ZAADTELLT EN ZAADHANDEL B.V., Di Lier (NL)

( * ) Notice: Subject to any disclaimer, the term of this patent is extended or adjusted under 35 U.S.C. 154(b) by 126 days.

(21) Appl. No.: 15/412,241

(22) Filed: Jan. 23, 2017

(65) Prior Publication Data

US 2017/0164570 A1 Jun. 15, 2017

Related U.S. Application Data

(63) Continuation-in-part of application No. PCT/EP2015/068860, filed on Aug. 17, 2015.

(30) Foreign Application Priority Data

Aug. 18, 2014 (EP) ..................... 14181306

(51) Int. Cl.
| | | |
|---|---|---|
| *C07K 5/00* | (2006.01) | |
| *C07K 14/415* | (2006.01) | |
| *A01H 1/02* | (2006.01) | |
| *A01H 5/08* | (2018.01) | |
| *A01K 67/033* | (2006.01) | |

(52) U.S. Cl.
CPC ............. *C07K 5/00* (2013.01); *A01H 1/02* (2013.01); *A01H 5/08* (2013.01); *A01K 67/033* (2013.01); *C07K 14/415* (2013.01); *A01K 2227/70* (2013.01)

(58) Field of Classification Search
CPC .............................. C12N 15/8286; C07K 5/00
See application file for complete search history.

(56) References Cited

U.S. PATENT DOCUMENTS

| 2014/0173771 A1 | 6/2014 | Schuurink et al. |
| 2015/0164014 A1 | 6/2015 | Van Den Enden et al. |

FOREIGN PATENT DOCUMENTS

| EP | 2 700 301 | 2/2014 |
| WO | 2012/169893 | 12/2012 |

OTHER PUBLICATIONS

Zhao et al (J Biol Chem. Apr. 20, 2012;287(17):14109-21 2012). (Year: 2012).*
Zhao et al (J Biol Chem. Apr. 20, 2012;287(17):14109-21 2012). (Year: 2012).*
Spyropoulou et al (BMC Genomics May 2014, 15:402) (Year: 2014).*
Dicke (Netherlands Journal of Zoology 38(2-4) 148-165 (1988)) (Year: 1988).*
Okabe et al (Plant Cell Physiol. 52(11): 1994-2005 (2011) (Year: 2011).*
Gupta et al (BMC Plant Biology 2014, 14:38) (Year: 2014).*
Hong et al (The Plant Cell, vol. 24: 2635-2648, Jun. 2012) (Year: 2012).*
NCBI Reference Sequence: NM_001301178.2 (Year: 2014).*
GenBank: KF428776.1 (Year: 2013).*
Spyropoulou et al (RNA sequencing on Solanum lycopersicum trichomes identifies transcription factors that activate terpene synthase promoters. BMC Genomics. 15:1-16, May 2014) (Year: 2014).*
Yan et al (Role of Tomato Lipoxygenase D in Wound-Induced Jasmonate Biosynthesis and Plant Immunity to Insect Herbivores. Plos Genomics. 7:1-16, 2013) (Year: 2013).*
Schmidt (Leaf structures affect predatory mites (*Acari: Phytoseiidae*) and biological control: a review. Exp Appl Acarol 62:1-17, published online Aug. 2013) (Year: 2013).*
Zhao et al (A Single Amino Acid Substitution in IIIf Subfamily of Basic Helix-Loop-Helix Transcription Factor AtMYC1 Leads to Trichome and Root Hair Patterning Defects by Abolishing Its Interaction with Partner Proteins in *Arabidopsis*. JBC. 287:14109-14121, 2012). (Year: 2012).*
Houten et al (Herbivory-associated degradation of tomato trichomes and its impacton biological control of Aculops lycopersici. Exp Appl Acarol 60:127-138, 2013). (Year: 2013).*
Xu et al (SlMYC1 Regulates Type VI Glandular Trichome Formation and Terpene Biosynthesis in Tomato Glandular Cells. The Plant Cell, vol. 30: 2988-3005, Dec. 2018) (Year: 2018).*
Boter et al (Conserved MYC transcription factors play a key role in jasmonate signaling both in tomato and *Arabidopsis*. Genes & Development 18:1577-1591, 2004). (Year: 2004).*
International Search Report and Written Opinion of the International Searching Authority dated Dec. 9, 2015, which issued during prosecution of International Application No. PCT/EP2015/068860.
Anonymous, "UPI0002BCB2F2", Jun. 2014, retrieved from http://www.uniprot.org/uniparc/UPI0002BCB2F2.

(Continued)

*Primary Examiner* — Ashley K Buran
*Assistant Examiner* — Wayne Zhong
(74) *Attorney, Agent, or Firm* — Duane Morris LLP; Thomas J. Kowalski; Deborah L. Lu

(57) ABSTRACT

The present invention relates to a modified Slmyc2 gene, which may comprise at least one modification as compared to the wild type sequence of SEQ ID No. 5, which modification leads to the reduction or absence of SlMYC2 protein activity, wherein the modified Slmyc2 gene is capable of conferring an aberrant glandular hair phenotype to a *Solanum lycopersicum* plant. The modification may be suitably selected from a modification that decreases the mRNA level of the Slmyc2 gene, a modification that decreases the level of the SlMYC2 protein and/or a modification that decreases the activity of the SlMYC2 protein, as compared to the wild type Slmyc2 gene of SEQ ID No. 5.

2 Claims, 22 Drawing Sheets
(2 of 22 Drawing Sheet(s) Filed in Color)
Specification includes a Sequence Listing.

(56) References Cited

OTHER PUBLICATIONS

Kang, et al. "Distortion of trichome morphology by the hairless mutation of tomato affects leaf surface chemistry" Journal of Experimental Botany, Mar. 2010, 61(4):1053-1064.

Schmidt, "Leaf structures affect predatory mites (*Acari: Phytoseiidae*) and biological control: a review" Experimental and Applied Acarology, Aug. 2013, 62(1):1-17.

Spyropoulou, et al. "RNA sequencing on Solanum lycopersicum trichomes identities transcription factors that activate terpene synthase promoters" BMC Genomics, May 2014, 15(1):402.

Zhao, et al. "A Single Amino Acid Substitution in IIIf Subfamily of Basic Helix-Loop-Helix Transcription Factor AtMYC1 Leads to Trichome and Root Hair Patterning Defects by Abolishing Its Interaction With Partner Proteins in *Arabidopsis*" The Journal of Biological Chemistry, Apr. 2012, 287(17):14109-14121.

Jiesen Xu, et al., SlMYC1 Regulates Type VI Glandular Trichome Formation and Terpene Biosynthesis in Tomato Glandular Cells, The Plant Cell (Dec. 2018) vol. 30:2988-3005.

\* cited by examiner

FIG. 1A

SEQ ID No. 1:

>SlMYC2_genomic_SNP
attcaataattaattgtaattgtctggcattgttatggtggttcacatgtcaagttgcttttatattatttgttattaaaataaaaatagaaaaatcaatgttat
tttcacgttcagcatccaccaaaacgtgctattaataatttaatgtctaaaacatatctacaaattatattatattagtataatatactttatgatatcttgaac
aaagacaattacaagtaggaccaatcaaaatgattccacaacgtgacgccaacgcgtacaaataaggattttccttttattataacttttataataattaact
caccgtaattaatttgtatgattataatgaaatgactgaaacttttttcgctcttaacaagaaatctcgatcgaactttagccatgaaataaaaataattgtgt
tgagagtagaatttccaaaaatagattttatagtgtgtaaaattatatttattaattttaatatgattatcaaaataccgaatcgaagaaagtaagtaaatt
ttaaggaatgtaatatgtatgtggtctcacccttacatgcattgaatatgtaaagagtgttttcgaaggacaaggatttttttgtttttactattaatgtattt
aaaaacttaagcaaaattatttactcaaaatttacatgcgatattgtactaaaacgatttacaattattgtaggtaccttaattactctgatagtgcatggc
ctttaattacaagggataccaataacaaaaaagtccatatttgtgatgaatatgtcttatcacaaaaattgagaggaatattatgatagatttaatgaaaa
attttaatatggacaaaagaatattatgatagatttaaagaaaaaatttaatatggacaaaatttgtgatggactaataaatttacttttttcattacgaatt
tttggagcctcacgttgaagatccaatgacttgttttcaaattagtttcaaagaatggctgagaatagtctttctaaaaaagcatcttcaatcgatggcttg
aatttaattattaaaagaattattatatttgataatgtattgattagatgcacgttatgaatttaaaatttcattttagacatgaacctaatatttaaatagac
accaacacaagtatatgacgcgaacaagtgatatttaagttatgagttcaaaatttatgaatcattagtcataactaaaaatgtgatactttaggggataa
ggatagaagagcaaatttaaattttacgtgaaccttttttatttaaatagaaaataatagagcgataaattcattatttatcgagtttcaaatcattaaaaat
acaatatataatatacgaattagatgtatatacacatttgaattcaatggtggactatataatttgatatttaagtaagcaaaagtagataaggagttcaa
gtttaaatttgtaaacatagaatttcctattttagagtttaaggtaaatttatgtatatttcgtttggaatctcattttacgatgctacgctaaatattaga
aattgctaaaaataattgttgttattgtaatataatatcaaaatcaacatgatttcattttattttctttccatatatgaattatttccataaagcctacatgtag
gagatatgctaatttaatatttcctggaaatagttaacttagttgaaacattgaagtattagatattttattaatataagcactttaacaaatatggttataa
aaaaaaatcttcttcttttcaattccttttaacattcattgaaaatcttcttatttaacaatattttttccaattagttcaataactcgtcttcaatcatcgaagatat
ttaatgttactttttttgaagtaatgaaatttacttctaataatcttgtctttttttttaaattggaaatgggaatagaaaatgataagacgaaattaaatcctc
acctacaagataaaagtttagataagttttgatagttaattaaatgaatttcaaattttttaatacttaaatacttctcattaataattgtaaagatatctactt
ttttcattcacttttttacttcaaaaataaatcaaattatgtcacactttcactgtaataaattatatatatataataaaaaaaaagaaaaatcttctacctatat
aagtacgactctctaatggtgttaagtaaaaagaaaaatttagtataaagtcctaggtagttaaaaagtaaaaagtagaactaatgccggctttcctttat
cctacgtataattttcccataaatcgcccaccttaatttttttttttctgattttcatttggcatcgaagcttatattagaatttaaacttacgttaaaattttttat
aatggcactaaaattttttactaacataaataattatcccatcctaataaaaatttaaataaaaaaatatttgattaaaaatacttaccgttttctcggaaccct
cttctcttgtccactcactttcctcactcattttattttgagctcacaatatttttattatatatatatatatatatccacaaaatctctactctcatttctcacctaa
caaacaaaatctctcattttctgtttttgtaaaattcttcaatttaattgaatgacggactatagattatggagtaataccaatactactaatacatgtgatg
atactatgatgatggattctttttatcttccgatccatcctcttttttggcctgcttccactcccaatcgtccgactccggtgaacggagtcggagaaacgat
gccgttttcaatcaagagtcactacagcaaaggcttcaggcttaattgacggtgctcgtgaatcatgggcatatgctattttctggcaatcgtcagttgt
tgattttgcgagccaaactgtattgggttggggagatgggtattataaaggagaagaagataagaataaacggagagggtcgtcagttcagcagct
aattttgttgctgagcaagagcatagaaagaaggtgcttcgggagctgaattcattaatatccggtgtacaagcttccgccggaaacggaactgatgat
gcagtggatgaggaagtgacggatactgaatggttttttctgatttcaatgacccaatcgtttgttaacggtaacgggcttccgggcttggcgatgtaca
gttcaagcccaatttgggttactggaacagagaaattagctgcttctcaatgtgaacgggccaggcaagcccaaggtttcgggcttcagacgattgtgt
gtattccttcagctaacggtgtagtggagcttggttcgactgagctgatattccaaagctcggatttgatgaacaaggttaagtatttgtttaacttcaata
ttgatatggggtctgttacaggctcaggttcgggctcaggtcttgtgctgtgcatcctgagcccgatccttcggcccttggcttacggatccatcttcctc
ggttgtggaacctaaggattcgttaattcatagtagtagtagggatgttcaacttgtgtatggaaatgagaattctgaaaatcagcagcagcattgtcaa
ggatttttcacaaaggagttgaattttcgggttatggatttgatggaagtagtaataggaataaaactggaatttcttgtaagccggagtccagggaga
tattgaattttggtgatagtagtaagagattttcaggcaatcacagttgggtcctgggcctgggctcatggaggagaacaagaacaagaacaagaac
aagaaaaggtcacttggatcaaggggaaacaatgaagaaggaatgctttcgtttgtttcgggtgtgatcttgccaacttcaacaatggggaagtccgg
ggattctgatcactcagatctcgaagcctcagtggtgaaggaggccgttgtagaacctgaaaagaagccgaggaagcgagggaggaaaccagccaa
tggaagggaggagccattgaatcacgtggaagcggagagacagaggagggagaaattgaatcaaagattctacgcgctcagagccgtagtcccaa
atgtgtctaaaatggataaggcatcacttcttagagatgcaattgcatacatcaatgagttgaaatcaaaagttcaaaattcagatttagataaagagga
gttgaggagccaaattgaatgtttaaggaaggaattaaccaacaagggatcatcaaactattccgcctcccctccattgaatcaagatgtcaagattgtc
gatatggacattgacgttaaggtgattggatgggatgctatgattcgtatacaatgtagtaaaagaaccatccagctgccaggctaatggcagccctc
aaggacttggacctagacgtgcaccacgctagtgtttccgtggtgaatgatttgatgatccaacaagccacagtcaaaatggggagccggctttatgct
caagaacagcttaggatagcattgacatcaaaaattgctgaatcgcgatgaaattatgtccctagtgagctatgtataatgttatcttctaatgagcgag
aattttcttctctgtatataaatgtgatgaaaccaatactagagatctcgagttgaggcttttagttcatgtaagattagatatatatatatgatgcagcttc
atccttttgtattcttcatccaggaaataaatgagaaaccaataattggtggctgatgatcaacttcatgttattactaattctcgttccctcttcttttgggat
acaacacttgtcatttttacattaggcaaattagaagaaaatactaagcatttttttaattgaacgtaacatgtcatgtgtgaactagagtcacaagttcaatt
catgtaacaaacaatcaccctttgcatttttagtggagaaggatgcattgagtttcaacttgtacactaactagtcataagagattactttgttataaaaaaa
aaacaattttttgaccttgttgtgtatataatatatgattcgagtttggacgaaagttttttatttaattatgatggatatattagttatggagtacacaattgcc tttactataaaacttattacttttttaataataaatattttttttaatgtaaatatataaatataatcaaaacttaatataaatggatgtattactaatcagttgctt
gttttagtctagaagaaagcaccaaacaaaggggtagggctgcattttcatttatagagaattcattgaatttggtcaaatcatagctgtattcattggac
taggaaatatttaaaaagtatatatattattgtttataataatataatgtcatgagtatcatttgagtttgaagtgacacaagccctttaaatgcagttgattt
aggcacaaactttgttattattcccgccgtccaaatagttgttacatttggcttcctaaaaattaatttaactaattttttaaatttaattttatattttgaaaaat
taaagtttataaatacaaaaattattttaatttcttacatataattaaaaaatatatataaaatttatataatttagcgctggaaaattattttgaaaacagag
gaagtattattattattttggtcttatgaattgtgtgataaacagtttatatctgttaatcaaatagacagagattgatagatgtgacaaagattcgtttttttg
tttgaggttttataaaaggaaaattgtataaaatagcaaactaataacttaaattaaatggaatagctagggtttgatttaattgtgctccatagcaaacg
ttggcaaaaatttaccagaagtctcgctcgccactctcccattctcgcctctctcgctttatacatagaagtgtataatttatgtttctgttttgtataaagcg
agagaaaattgtatatacacatgcaaaaatgtatatctttgtgttatacacttaattatataatttacaaacattttacttcaaatattgcagcgaaaaaggc
caaagaattatacaatcgtgaattatataattgcagtgaaatacaattttttctagctttatacaacagaagtgtatatattgtatttctgtttttgtataaag
cgagaaaaacatatatcttcttgctatacacttataattatgcaatatacatacattttaattcgattaaactgtatacaaaactaattatacaattgcagcg
aaatggcgaattatacaatttaggccagcgaattatacacttttatatgtatagcgaattatacagttttatatttgctatggagcgcatatattatacaaa
tatgattttttttgtttgctatatgtgaaagttgccctttttataaaagctttatgtatagtttgatttgttttttttaaaaaataaaatatgacaacttagtatcaa
aatagattaaatttatatacaataaatagttatattttacagccagccatttatctttcttttttttcaagccacaaaatcaccttgtagaaagttattttgttcg
atattttattgctaatatataaaaatattattataaaaagcatgtaatatatatataaaaatttgatttcaaagaatactttgatcattataatgatatgttaat
ataaataataattattatagattaatctgatcgtatattttcagtatacattaatatatacatctaaaatatgactgtattaaatatgaacaaaatcatttcat
caccctatataatattttaattaaaaagatgtataaagaagaataaaaaaacgctgaagtttaaagcgaatgttattgaccagatcaaattgacttgaaga
ccaaaattgaattgttgaatacaattaattaatttaaaaatgaccatgttttacatgtgaaattcatttatatatatatatatatcatatatattattatagtatt
cacattttgttgtttacactgatggttccgttaagtgttcacatttctttgtttaacactaaactttggagggaaggatgtgaaaataaaaaatttgggtaga
aaattaatcgataatttaatattgtctaatttatcttatgtatattatgatcattactcccttattatctttgtattttttttaatcttgattatcatattatttagtatt
tttttatccttaattttgatatgttttacttgagtcaaaaatctatagaaaataatttttctattttttacaagataagggtaaagatgtgcgaacacaactttttt
gaagccccacttatgaaattacactgaacatattgttgtagtaactgtacgaactcttttttctttctatataaacaaatgtataactaaagtatttagtaaaa
taaaaatataattctatttagttcatgaatgagaccacaatatgaatgtatagagctgggggatatttttttgttttttgtgtagatggatattaatcgaagatgt
attggttcttaatagtaagaataacaatagccattaccctaaagattgattcacctttattttagggtataaccaaaaaagaatggacattattaacacga
gacctttagcatttccaaaaaaaatgggagaattttgttatttatttaaaaagaaaaaaaaaagaacacacccttaacctcaatatcctcaaaaattcaa
ccatcaatatcattattttattttcatatcctatgcatttttttattagcttgtaaacttttaattttcttcctattcttttatacaacaatgactctcaattgtttaacc
tgccaagctctaaaagaacagattcacatgaggaactaagggaaacactgaatcatgttaatgataagtcgaattttcgtcttttttcagtgggaatgg
agaggaactggtcagggaacttggttgaaagacggaaatatgaaaaaacgaggggtcgaaccataatgggaaaagaaaataat

SEQ ID No. 2:

>SlMYC2_CDS_SNP
atgacggactatagattatggagtaataccaatactactaatacatgtgatgatactatgatgatggattcttttttatcttccgatccatcctcttttttggcc
tgcttccactcccaatcgtccgactccggtgaacggagtcggagaaacgatgccgttttttcaatcaagagtcactacagcaaaggcttcaggctttaatt
gacggtgctcgtgaatcatgggcatatgctattttctggcaatcgtcagttgttgattttgcgagccaaactgtattgggttggggagatgggtattataa
aggagaagaagataagaataaacggagagggtcgtctagttcagcagctaattttgttgctgagcaagagcatagaaagaaggtgcttcgggagctg
aattcattaatatccggtgtacaagcttccgccggaaacggaactgatgatgcagtggatgaggaagtgacggatactgaatggttttttctgatttcaa
tgacccaatcgtttgttaacggtaacgggcttccgggcttggcgatgtacagttcaagcccaatttgggttactggaacagagaaattagctgcttctca
atgtgaacgggccaggcaagcccaaggtttcgggcttcagacgattgtgtgtattccttcagctaacggtgtagtggagcttggttcgactgagctgat
attccaaagctcggatttgatgaacaaggttaagtatttgtttaacttcaatattgatatggggtctgttacaggctcaggttcgggctcaggctcttgtgc
tgtgcatcctgagcccgatccttcggccctttggcttacggatccatcttcctcggttgtggaacctaaggattcgttaattcatagtagtagtagggatgt
tcaacttgtgtatggaaatgagaattctgaaaatcagcagcagcattgtcaaggatttttcacaaaggagttgaattttcgggttatggatttgatggaa
gtagtaataggaataaaactggaatttcttgtaagccggagtccagggagatattgaattttggtgatagtagtaagagattttcagggcaatcacagtt
gggtcctgggcctgggctcatggaggagaacaagaacaagaacaagaacaagaaaaggtcacttggatcaaggggaaacaatgaagaaggaatg
ctttcgtttgtttcgggtgtgatcttgccaacttcaacaatggggaagtccgggattctgatcactcagatctcgaagcctcagtggtgaaggaggccg
ttgtagaacctgaaaagaagccgaggaagcgagggaggaaaccagccaatggaagggaggagccattgaatcacgtggaagcggagagacaga
ggagggagaaattgaatcaaagattctacgcgctcagagccgtagtcccaaatgtgtctaaaatggataaggcatcacttcttagagatgcaattgcat
acatcaatgagttgaaatcaaaagttcaaaattcagatttagataaagaggagttgaggagccaaattgaatgtttaaggaaggaattaaccaacaag
ggatcatcaaactattccgcctcccctccattgaatcaagatgtcaagattgtcgatatggacattgacgttaaggtgattggatgggatgctatgattcg
tatacaatgtagtaaaaagaaccatccagctgccaggctaatggcagccctcaaggacttggacctagacgtgcaccacgctagtgtttccgtggtgaa
tgatttgatgatccaacaagccacagtcaaaatgggggagccggctttatgctcaagaacagcttaggatagcattgacatcaaaaattgctgaatcgcg
atga

SEQ ID No. 3:

>SlMYC2_AA_STOP
MTDYRLWSNTNTTNTCDDTMMMDSFLSSDPSSFWPASTPNRPTPVNGVGETMPFFNQESLQQRLQALIDGARE
SWAYAIFWQSSVVDFASQTVLGWGDGYYKGEEDKNKRRGSSSSAANFVAEQEHRKKVLRELNSLISGVQASAGN
GTDDAVDEEVTDTEWFFLISMTQSFVNGNGLPGLAMYSSSPIWVTGTEKLAASQCERARQAQGFGLQTIVCIPSA
NGVVELGSTELIFQSSDLMNKVKYLFNFNIDMGSVTGSGSGSGSCAVHPEPDPSALWLTDPSSSVVEPKDSLIHSS
SRDVQLVYGNENSENQQQHCQGFFTKELNFSGYGFDGSSNRNKTGISCKPESREILNFGDSSKRFSGQSQLGPGP
GLMEENKNKNKNKKRSLGSRGNNEEGMLSFVSGVILPTSTMGKSGDSDHSDLEASVVKEAVVEPEKKPRKRGRKP
ANGREEPLNHVEAERQRREKLNQRFYALRAVVPNVSKMDKASLL*DAIAYINELKSKVQNSDLDKEELRSQIECLR
KELTNKGSSNYSASPPLNQDVKIVDMDIDVKVIGWDAMIRIQCSKKNHPAARLMAALKDLDLDVHHASVSVVNDL
MIQQATVKMGSRLYAQEQLRIALTSKIAESR

SEQ ID No. 4:

>SL06992
ggaagcggagagacagaggagggagaaattgaatcaaagattctacgcgctcagagccgtagtcccaaatgtgtctaaaatggataa
ggcatcacttctttgagatgcaattgcatacatcaatgagttgaaatcaaaagttcaaaattcagatttagataaagaggagttgaggag
ccaaattgaatgtttaaggaagga

FIG. 1C

SEQ ID No. 5:

>SlMYC2_genomic_WT
attcaataattaattgtaattgtctggcattgttatggtggttcacatgtcaagttgcttttatattatttgttattaaaataaaaatagaaaaatcaatgttat
tttcacgttcagcatccaccaaaacgtgctattaataatttaatgtctaaaacatatctacaaattatattatattagtataatatactttatgatatcttgaac
aaagacaattacaagtaggaccaatcaaaatgattccacaacgtgacgccaacgcgtacaaataaggattttcctttattataactttataataattaact
caccgtaattaatttgtatgattataatgaaatgactgaaactttttcgctcttaacaagaaatctcgatcgaactttagccatgaaataaaaataattgtgt
tgagagtagaatttccaaaaatagattttatagtgtgtaaaattatatttattaatttttaatatgattatcaaaataccgaatcgaagaaagtaagtaaatt
ttaaggaatgtaatatgtatgtggtctcacccttacatgcattgaatatgtaaagagtgttttcgaaggacaaggattttttgtttttactattaatgtattt
aaaaacttaagacaaaattatttactcaaaatttacatgcgatattgtactaaaacgatttacaattattgtaggtaccttaattactctgatagtgcatggc
ctttaattacaagggataccaataacaaaaaagtccatatttgtgatgaatatgtcttatcacaaaaattgagaggaatattatgatagatttaatgaaaa
attttaatatggacaaaagaatattatgatagatttaaagaaaaaatttaatatggacaaaatttgtgatggactaataaatttacttttttcattacgaatt
tttggagcctcacgttgaagatccaatgacttgttttcaaattagtttcaaagaatggctgagaatagtctttctaaaaaagcatcttcaatcgatggcttg
aatttaattattaaaagaattattatatttgataatgtattgattagatgcacgttatgaatttaaaatttcatttagacatgaacctaatatttaaatagac
accaacacaagtatatgacgcgaacaagtgatatttaagttatgagttcaaaatttatgaatcattagtcataactaaaaatgtgatactttaggggataa
ggatagaagagcaaatttaaatttacgtgaacctttttatttaaatagaaaataatagagcgataaattcattatttatcgagtttcaaatcattaaaaat
acaatatataatatacgaattagatgtatatacacatttgaattcaatggtggactatataatttgatatttaagtaagcaaaagtagataaggagttcaa
gtttaaatttgtaaacatagaatttcctattttagagtttaaggtaaatttatgtatattttatcgtttggaatctcattttacgatgctacgctaaatattaga
aattgctaaaaataattgttgttattgtaatataatatcaaaatcaacatgatttcatttattttctttccatatatgaattatttccataaagcctacatgtag
gagatatgctaatttaatatttcctggaaatagttaacttagttgaaacattgaagtattagatattttattaatataagcactttaacaaatatggttataa
aaaaaaatcttcttcttttcaattccttaacattcattgaaaatcttcttatttaacaatatttttccaattagttcaataactcgtcttcaatcatcgaagatat
ttaatgttacttttttgaagtaatgaaatttacttctaataatcttgtctttttttaaattggaaatgggaatagaaaatgataagacgaaattaaatcctc
acctacaagataaaagtttagataagttttgatagttaattaaatgaatttcaaatttttaatacttaaatacttctcattaataattgtaaagatatctactt
ttttcattcactttttacttcaaaaataaatcaaattatgtcacactttcactgtaataaattatatatatataataaaaaaaagaaaaatcttctacctatat
aagtacgactctctaatggtgttaagtaaaaagaaaaatttagtataaagtcctaggtagttaaaaagtaaaaagtagaactaatgccggctttccttat
cctacgtataattttcccataaatcgcccaccttaattttttttttctgattttcatttggcatcgaagcttatattagaatttaaacttacgttaaaatttttat
aatggcactaaaattttactaacataaataattatcccatcctaataaaaatttaaataaaaaatatttgattaaaaatacttaccgtttttctcggaacct
cttctctttgtccactcactttcctcactcatttatttttgagctcacaatatttttattatatatatatatatatccacaaaaatctctactctcatttctcacctaa
caaacaaaatctctcattttctgtttttgtaaaattcttcaatttaattgaatgacggactatagattatggagtaataccaatactactaatacatgtgatg
atactatgatgatggattctttttatcttccgatccatcctcttttttggcctgcttccactcccaatcgtccgactccggtgaacggagtcggagaaacgat
gccgttttcaatcaagagtcactacagcaaaggcttcaggctttaattgacggtgctcgtgaatcatgggcatatgctattctggcaatcgtcagttgt
tgattttgcgagccaaactgtattgggttggggagatgggtattataaggagaagaagataagaataaacggagagggtcgtctagttcagcagct
aatttgttgctgagcaagagcatagaaagaaggtgcttcgggagctgaattcattaatatccggtgtacaagcttccgccggaaacggaactgatgat
gcagtggatgaggaagtgacggatactgaatggttttttctgatttcaatgacccaatcgtttgttaacggtaacgggcttccgggcttggcgatgtaca
gttcaagcccaatttgggttactggaacagagaaattagctgcttctcaatgtgaacgggccaggcaagcccaaggtttcgggcttcagacgattgtgt
gtattccttcagctaacggtgtagtggagcttggttcgactgagctgatattccaaagctcggatttgatgaacaaggttaagtatttgtttaacttcaata
ttgatatggggtctgttacaggctcaggttcgggctcaggctcttgtgctgtgcatcctgagcccgatccttcggccctttggcttacggatccatcttcctc
ggttgtggaacctaaggattcgttaattcatagtagtagtagggatgttcaacttgtgtatggaaatgagaattctgaaaatcagcagcagcattgtcaa
ggatttttcacaaaggagttgaattttttcgggttatggatttgatggaagtagtaataggaataaaactggaatttcttgtaagccggagtccagggaga
tattgaattttggtgatagtagtaagagattttcagggcaatcacagtttgggtcctgggcctgggctcatggaggagaacaagaacaagaacaagaac
aagaaaaggtcacttggatcaaggggaaacaatgaagaaggaatgctttcgtttgtttcgggtgtgatcttgccaacttcaacaatggggaagtccgg
ggattctgatcactcagatctcgaagcctcagtggtgaaggaggccgttgtagaacctgaaaagaagccgaggaagcgagggaggaaaccagccaa
tggaagggaggagccattgaatcacgtggaagcggagagacagaggagggagaaattgaatcaaagattctacgcgctcagagccgtagtcccaa
atgtgtctaaaatggataaggcatcacttcttggagatgcaattgcatacatcaatgagttgaaatcaaaagttcaaaattcagatttagataaagagga
gttgaggagccaaattgaatgtttaaggaaggaattaaccaacaagggatcatcaaactattccgcctccctccattgaatcaagatgtcaagattgtc
gatatggacattgacgttaaggtgattggatgggatgctatgattcgtatacaatgtagtaaaaagaaccatccagctgccaggctaatggcagccctc
aaggacttggacctagacgtgcaccacgctagtgtttccgtggtgaatgatttgatgatccaacaagccacagtcaaaatggggagccggctttatgct
caagaacagcttaggatagcattgacatcaaaaattgctgaatcgcgatgaaattatgtcccctagtgagctatgtataatgttatctttctaatgagcgag
aattttcttctctgtatataaatgtgatgaaaccaatactagagatctcgagttgaggcttttagttcatgtaagattagatatatatatatgatgcagcttc
atcctttgtattcttcatccaggaaataaatgagaaaccaataattggtggctgatgatcaacttcatgttattactaattctcgttccctcttctttgggat
acaacacttgtcattttacattaggcaaattagaagaaaatactaagcattttttaattgaacgtaacatgtcatgtgtgaactagagtcacaagttcaatt
catgtaacaaacaatcaccctttgcattttagtggagaaggatgcattgagtttcaacttgtacactaactagtcataagagattactttgttataaaaaaa

FIG. 2A aaacaattttttgaccttgttgtgtatataatatatgattcgagtttggacgaaagtttttatttaattatgatggatatattagttatggagtacacaattgcc
tttactataaaacttattacttttttaataataaatattttttttaatgtaaatatataaatataatcaaaacttaatatataaatggatgtattactaatcagttgctt
gttttagtctagaagaaagcaccaaacaaaggggtagggctgcattttcatttatagagaattcattgaatttggtcaaatcatagctgtattcattggac
taggaaatatttaaaaagtatatatattattgtttataataatataatgtcatgagtatcatttgagtttgaagtgacacaagcccctttaaatgcagttgattt
aggcacaaactttgttattattcccgccgtccaaatagttgttacatttggcttcctaaaaattaatttaactaatttttaaatttaattttatattttgaaaaat
taaagtttataaatacaaaaattattttaatttcttacatataattaaaaaatatatataaaatttatataatttagcgctggaaaattattttgaaaacagag
gaagtattattattattttggtcttatgaattgtgtgataaacagtttatatctgttaatcaaatagacagagattgatagatgtgacaaagattcgttttttg
tttgaggttttataaaaggaaaattgtataaaatagcaaactaataacttaaattaaatggaatagctagggtttgatttaattgtgctccatagcaaacg
ttggcaaaaatttaccagaagtctcgctcgccactctcccattctcgcctctctcgctttatacatagaagtgtataattttatgtttctgttttgtataaagcg
agagaaaattgtatatacacatgcaaaaatgtatatctttgtgttatacacttaattatataatttacaaacattttacttcaaatattgcagcgaaaaaggc
caaagaattatacaatcgtgaattatataattgcagtgaaatacaattttttctagctttatacaacagaagtgtatatattgtatttctgttttgtataaag
cgagaaaaacatatatcttcttgctatacacttataattatgcaatatacatacattttaattcgattaaactgtatacaaaactaattatacaattgcagcg
aaatggcgaattatacaatttaggccagcgaattatacactttatatgtatagcgaattatacagttttatatttgctatggagcgcatatattatacaaa
tatgattttttttgtttgctatatgtgaaagttgccctttttataaaagctttatgtatagtttgatttgttttttaaaaaataaaatatgacaactttagtatcaa
aatagattaaatttatatacaataaatagttatattttacagccagccatttatctttctttttttttcaagccacaaaatcaccttgtagaaagttattttgttcg
atattttattgctaatatataaaaatattattataaaaagcatgtaatatatatataaaaatttgatttcaaagaatactttgatcattataatgatatgttaat
ataaataataattattatagattaatctgatcgtatattttcagtatacattaatatatacatctaaaatatgactgtattaaatatgaacaaaatcatttacat
caccctatataatattttaattaaaaagatgtataaagaagaataaaaaacgctgaagtttaaagcgaatgttattgaccagatcaaattgacttgaaga
ccaaaattgaattgttgaatacaattaattaatttaaaaatgaccatgttttacatgtgaaattcatttatatatatatatatatatcatatattattatagtatt
cacattttgttgtttacactgatggttccgttaagtgttcacatttctttgtttaacactaaactttggagggaaggatgtgaaaataaaaaatttgggtaga
aaattaatcgataatttaatattgtctaatttatcttatgtatattatgatcattactcccttattatctttgtattttttaatcttgattatcatattatttagtatt
ttttatccttaattttgatatgtttacttgagtcaaaaatctatagaaaataattttttctattttacaagataagggtaaagatgtgcgaacacaacttttt
gaagccccacttatgaaattacactgaacatattgttgtagtaactgtacgaactctttttctttctatataaacaaatgtataactaaagtatttagtaaaa
taaaaatataattctatttagttcatgaatgagaccacaatgaatgtatagagctggggatatttttgtttttgtgtagatggatattaatcgaagatgt
attggttcttaatagtaagaataacaatagccattaccctaaagattgattccctttattttagggtataaaccaaaaaagaatggacattattaacacga
gacctttagcatttccaaaaaaatgggagaattttgttatttatttaaaaagaaaaaaaaaagaacacaccccttaacctcaatatcctcaaaaattcaa
ccatcaatatcattattttattttcatatcctatgcatttttttattagcttgtaaacttttaattttcttcctattcttttatacaacaatgactctcaattgtttaacc
tgccaagctctaaaaagaacagattcacatgaggaactaagggaaacactgaatcatgttaatgataagtcgaattttcgtctttttcagtgggaatgg
agaggaactggtcagggaacttggttgaaagacggaaatatgaaaaaacgaggggtcgaaccataatgggaaaagaaaataat SEQ ID No. 6:

>SlMYC2_CDS_WT
atgacggactatagattatggagtaataccaatactactaatacatgtgatgatactatgatgatggattcttttttatcttccgatccatcctcttttttggcc
tgcttccactcccaatcgtccgactccggtgaacggagtcggagaaacgatgccgttttcaatcaagagtcactacagcaaaggcttcaggctttaatt
gacggtgctcgtgaatcatgggcatatgctattttctggcaatcgtcagttgttgattttgcgagccaaactgtattgggttggggagatgggtattataa
aggagaagaagataagaataaacggagagggtcgtctagttcagcagctaattttgttgctgagcaagagcatagaaagaaggtgcttcgggagctg
aattcattaatatccggtgtacaagcttccgccggaaacggaactgatgatgcagtggatgaggaagtgacggatactgaatggttttttctgatttcaa
tgacccaatcgtttgttaacggtaacgggcttccgggcttggcgatgtacagttcaagcccaatttgggttactggaacagagaaattagctgcttctca
atgtgaacgggccaggcaagcccaaggtttcggcttcagacgattgtgtgtattccttcagctaacggtgtagtggagcttggttcgactgagctgat
attccaaagctcggatttgatgaacaaggttaagtatttgtttaacttcaatattgatatggggtctgttacaggctcaggttcgggctcaggctcttgtgc
tgtgcatcctgagcccgatccttcggccctttggcttacggatccatcttcctcggttgtggaacctaaggattcgttaattcatagtagtagtagggatgt
tcaacttgtgtatggaaatgagaattctgaaaatcagcagcagcattgtcaaggattttcacaaaggagttgaattttcgggttatggatttgatggaa
gtagtaataggaataaaactggaatttcttgtaagccggagtccagggagatattgaattttggtgatagtagtaagagattttcagggcaatcacagtt
gggtcctgggcctgggctcatggaggagaacaagaacaagaacaagaacaagaaaaggtcacttggatcaaggggaaacaatgaagaaggaatg
ctttcgtttgtttcgggtgtgatcttgccaacttcaacaatggggaagtccgggattctgatcactcagatctcgaagcctcagtggtgaaggaggccg
ttgtagaacctgaaaagaagccgaggaagcgagggaggaaaccagccaatggaagggaggagccattgaatcacgtggaagcggagagacaga
ggagggagaaattgaatcaaagattctacgcgctcagagcctagtcccaaatgtgtctaaaatggataaggcatcacttcttggagatgcaattgcat
acatcaatgagttgaaatcaaaagttcaaaattcagatttagataaagaggagttgaggagccaaattgaatgtttaaggaaggaattaaccaacaag
ggatcatcaaactattccgcctcccctccattgaatcaagatgtcaagattgtcgatatggacattgacgttaaggtgattggatgggatgctatgattcg
tatacaatgtagtaaaagaaccatccagctgccaggctaatggcagccctcaaggacttggacctagacgtgcaccacgctagtgtttccgtggtgaa
tgatttgatgatccaacaagccacagtcaaaatggggagccggctttatgctcaagaacagcttaggatagcattgacatcaaaaattgctgaatcgcg
atga

FIG. 2B

SEQ ID No. 7:

>SlMYC2_AA_WT
MTDYRLWSNTNTTNTCDDTMMMDSFLSSDPSSFWPASTPNRPTPVNGVGETMPFFNQESLQQRLQALIDGARE
SWAYAIFWQSSVVDFASQTVLGWGDGYYKGEEDKNKRRGSSSSAANFVAEQEHRKKVLRELNSLISGVQASAGN
GTDDAVDEEVTDTEWFFLISMTQSFVNGNGLPGLAMYSSSPIWVTGTEKLAASQCERARQAQGFGLQTIVCIPSA
NGVVELGSTELIFQSSDLMNKVKYLFNFNIDMGSVTGSGSGSGSCAVHPEPDPSALWLTDPSSSVVEPKDSLIHSS
SRDVQLVYGNENSENQQQHCQGFFTKELNFSGYGFDGSSNRNKTGISCKPESREILNFGDSSKRFSGQSQLGPGP
GLMEENKNKNKNKKRSLGSRGNNEEGMLSFVSGVILPTSTMGKSGDSDHSDLEASVVKEAVVEPEKKPRKRGRKP
ANGREEPLNHVEAERQRREKLNQRFYALRAVVPNVSKMDKASLLGDAIAYINELKSKVQNSDLDKEELRSQIECLR
KELTNKGSSNYSASPPLNQDVKIVDMDIDVKVIGWDAMIRIQCSKKNHPAARLMAALKDLDLDVHHASVSVVNDL
MIQQATVKMGSRLYAQEQLRIALTSKIAESR

SEQ ID No. 8:

>SL06992
ggaagcggagagacagaggagggagaaattgaatcaaagattctacgcgctcagagccgtagtcccaaatgtgtctaaaatggataaggcatcactt
cttggagatgcaattgcatacatcaatgagttgaaatcaaaagttcaaaattcagatttagataaagaggagttgaggagccaaattgaatgtttaagg
aagga

| Sample ID | cis-3-hexenal | α-pinene | verbenene | myrcene | carene | α-phellandrene | p-cymene | limonene | β-phellandrene[†] | δ-elemene[†] | β-caryophyllene | α-humulene[‡] |
|---|---|---|---|---|---|---|---|---|---|---|---|---|
| Mo14/001 | 46 | <0.1 | <0.1 | <0.1 | <0.1 | <0.1 | <0.1 | <0.1 | <0.1 | <0.1 | <0.1 | <0.1 |
| Mo14/002 | 52 | <0.1 | <0.1 | <0.1 | <0.1 | <0.1 | <0.1 | <0.1 | <0.1 | <0.1 | <0.1 | <0.1 |
| Mo14/003 | 45 | <0.1 | <0.1 | <0.1 | <0.1 | <0.1 | <0.1 | <0.1 | <0.1 | <0.1 | <0.1 | <0.1 |
| Mo14/004 | 39 | <0.1 | <0.1 | <0.1 | <0.1 | <0.1 | <0.1 | <0.1 | <0.1 | <0.1 | <0.1 | <0.1 |
| Mo14/005 | 46 | <0.1 | <0.1 | <0.1 | <0.1 | <0.1 | <0.1 | <0.1 | <0.1 | <0.1 | <0.1 | <0.1 |
| Mo14/006 | 36 | <0.1 | <0.1 | <0.1 | <0.1 | <0.1 | <0.1 | <0.1 | <0.1 | <0.1 | <0.1 | <0.1 |
| Mo14/007 | 29 | 27 | 6 | 8 | 94 | 11 | 4 | 34 | 410 | 8 | 48 | 26 |
| Mo14/008 | 29 | 42 | 12 | 13 | 204 | 15 | 8 | 69 | 954 | 7 | 47 | 25 |
| Mo14/009 | 41 | 17 | 6 | 9 | 70 | 5 | 5 | 24 | 285 | 7 | 80 | 40 |
| Mo14/010 | 63 | 33 | 6 | 22 | 120 | 11 | 6 | 47 | 533 | 8 | 62 | 32 |
| Mo14/011 | 54 | 10 | <0.1 | 13 | 35 | <0.1 | <0.1 | 13 | 137 | 9 | 80 | 40 |
| Mo14/012 | 77 | 7 | <0.1 | 8 | 19 | <0.1 | <0.1 | 8 | 91 | 7 | 58 | 32 |
| Mo14/013 | 15 | 63 | 35 | 13 | 186 | 32 | 9 | 95 | 1227 | 10 | 28 | 16 |
| Mo14/014 | 19 | 47 | 21 | 12 | 123 | 12 | 8 | 66 | 823 | 10 | 27 | 14 |
| Mo14/015 | 27 | 70 | 33 | 19 | 206 | 30 | 12 | 103 | 1413 | 15 | 49 | 26 |
| Mo14/016 | 35 | 63 | 17 | 16 | 290 | 40 | 9 | 114 | 1492 | 11 | 18 | 11 |
| Mo14/017 | 34 | 62 | 21 | 23 | 254 | 29 | 10 | 92 | 1328 | 21 | 51 | 28 |
| Mo14/018 | 35 | 54 | 15 | 21 | 208 | 25 | 9 | 79 | 1073 | 15 | 45 | 23 |

FIG. 4B

| | cis-3-hexenal | α-pinene | verbenene | myrcene | carene | α-phellandrene | p-cymene | limonene | β-phellandrene* | δ-elemene† | β-caryophyllene | α-humulene† |
|---|---|---|---|---|---|---|---|---|---|---|---|---|
| Average Mo14/007-012 | 48,8 | 22,8 | 7,5 | 12,1 | 90,3 | 10,4 | 5,8 | 32,5 | 401,6 | 7,7 | 62,5 | 32,5 |
| SD | 19,3 | 13,6 | 3,2 | 5,5 | 66,9 | 4,3 | 1,9 | 22,8 | 317,2 | 0,7 | 14,8 | 6,4 |
| Average Mo14/013-018 | 27,5 | 59,8 | 23,7 | 17,5 | 211,1 | 28,1 | 9,5 | 91,4 | 1226,0 | 13,7 | 36,2 | 19,6 |
| SD | 8,5 | 8,0 | 8,3 | 4,5 | 57,4 | 9,3 | 1,3 | 17,2 | 245,5 | 4,3 | 13,6 | 7,1 |
| P-value | 0,03 | 0,00 | 0,01 | 0,09 | 0,01 | 0,01 | 0,01 | 0,00 | 0,00 | 0,01 | 0,01 | 0,01 |

SEQ ID No. 9:

>c_annuum_gDNA
ctctaaatatgtaaaatgaattaggaataaatgcacatattttccttcgcagaaagagatagcaacatggacctcaaacagcctcttggcatattatttact
taactatcaaaatggttaaatgtgtattttataataactaaaagcttaaacaataaagtaataaatcttattagtatattttatttctatctgtatcatcgactc
cttcatatgtctataattaatactttttgctaaacataacattatttcttttataagttgaaacactgaattatcacactttcatattatataaactcgtaactg
aaaatgtttcaaaaatagttatagataatatcttttcaattcctaaattcaactcctcaacccaaggaaagaatggaaatggattcatatacgttgatttctc
attctttttctatcatttcatttaccttcctattgagagggaaatggaatcaagaaaatgatcaaccacattattagatactcacttcgttagtgttatttgtta
aatattgacttgatacactgcacctttgggtgtggttgagttggtttgagggtgactttcaaagcgaaggtcgcggtatcaattccctctaatgcttttc
aatctagctcgtcacactaggtttacctagtgcggtttacatctcctgtgtggtttacgagtgattatacagtgaggggtttacccaatacacacaaagtgc
tcacccgaagggcagaggctagtggctgggtaaacccgaagggcagaggctagtggctgcggggtttacccagtgcgcacaaagtgctcacccgac
tttcctgaagtttcaaaaaatatatatatatatatattgacttgatacatttcttaaagagcaaaataaattaaaaattaaataataactcaactctacatt
ttcttaattgaacagaaaaataagtaactatgttttggtacagtgaataaatagaagtggtcgaaaaagtattttctccattctagaagtacaccaagctt
ctaataagagtcaacacacctaagtttaaacgtaattcaaacatcaatttcttagttttaaaactaaattatggatattaaaaaattataagaaaaacaaa
tgatactccttacaatttatttggttatcagattacaactgattcgacttgtcaaataataatgattgaaatatatgataggatatgtcgcagtaagagatt
gaatcataataggtgaggataaacgctattgcaaaaaaagttttaattttcaccaaatatgggaaactacttcaaatatactccatcaatttacatttaa
agaataaataattaatattaaggataaaagatttttttttttaatcttatttttgatatatcaaaatgataagtataaataaaaattcaattaaagaaataatg
taacgtaaaagtgaacagagggaatcctttttagtagacatttatatttagttgaagtttaaaaatcccaaataattcaaattaaagttgactttcataaac
acttattaaaaaaatcagccaaagataatacatttataaaaatgtaattttcaaatgaattaactagacgtaaattttttttttttcaaaagtaatttttaata
agttattttaataaaaaagcttctcaaaataagaaatttttatagccacttgaccaaacaagtctcccaaacatgaatttgaattaattttaaaaaaatttc
gcaagtaaaactaaaaagacttcttaaaatgtgttttcaaaatttaaattctattcaagtttgatattatcctaaaattattgaccatattagaaatgtttg
attgaaattatttcttgaaaattagaaaaaaaatgaggttctttgatatttttttgaagcagtggtatggccatataagaatacactcattatatgttattga
ttggttgctgattaaagaagttcgtctttttaatttttttattcgatatttatattgaaactttgattaccttactgtaagatgtgacatttctaacaaaattatatt
tatattaaaaattttaaaattaaaacatttaattaagggtgagccagatccactaccgcaccgtagccgcgacccatatggtacaagaggagtagtagtg
atgttggcgattaattggcgggtccttcgtggaacccgccagtctctttcctcattctcccaaattcagctcaaattcacctcaaataaaacccaaactcaa
attccactcttattaaccaaaccaatatttctctctcattttctccgccacacccctctatcctcattctctctctctctacacaccattttcacctgttttctgct
gtgtgttttatggaatgactgattacagcttgccaccatgaatctctggaataacagtactactgatgacaacgtttctatgatggaggcttttatgtcttc
cgatctttcttttggggtggtactactacttctagtgctactgctactgctgctgtcttgctaatcccaattatacttcaactgtttaccctcctcctggcgct
tcttgtgcatcttccgtaacggctacagctgctgctgtgactgttgatgcgtcaaaaaccatgccatttttcaaccaggagacgctacagcagcgtcttca
gaccctaatagacggtgctcgtgagacgtggacgtatgctatcttctggcagtcgtctgatttagatttctcgagtccgtctgtgttgggttggggtgatg
gttattacaaaggggaggaggataaaaacaagaggaaattatctgtttcttctccggcttatattgctgagcaggaacatcggaagaaggttcttagag
agctgaattcgttgatttcagggacacaaactggtacagacgatgctgttgatgaagaagttaccgataccgaatggttctttcttatctccatgactcaa
tcttttgtcaacgggaacgggcttccgggccaggctatgtgcagttccagcccgatttgggttgccggagtagaaattggctgcttctcactgtgaac
gggctcggcaggcccaagggttcgggcttcagacgatggtgtgtatcccttcagctaacggtgttgttgaattgggttcgacggagttgattatccaga
gttctgatctgatgaataaggttagagtactgttcaatttcaataatgatttggggtcaggttcatgggctgtgcagccggagagcgatccgtcagcgct
ttggttgacggagccatcttcctcaggtatggaagttagagagtctttaaatacagttcaaacaagttcaattccatcaagtaatagtaataagcaaattg
cgtatggaaatgagaacaatgatcatccatctggaaatgggaatggtcatagttcttataatcagcagcatcctcatcaacaaacacaaggattttcac
gaaggagttaaactttcggactttgggttcgatggaagtagtaataggaacgggaattcatcgctctcttgcaagcctgagtctggggaaatcttgaat
tttggtgatagtacgaagaaaagtgcttgtagtgcaaatgggaacttgttttcgggccattcccaatttggggcaggtgaggagaacaagaacaagac
caagaaaaggtcagctacttccaggggaagcaatgaagaaggaatgctttcatttgtttcgggtacagttttgccttcttccggtatgaagtcaggcgga
ggcgaagactctgaccattcagatcttgaagcttcggtggtgaaagaagctgatagtagtagagttgtagaaccggaaaagaagccaaggaagcga
ggaaggaagcctgctaatggaagggaggaacctttgaatcatgttgaggcagagaggcaaaggagggagaaattgaaccaaagattctacgcgctt
agagctgttgtaccgaatgtgtctaagatggacaaggcatcacttcttggagatgcaatttcatacataaatgagttgaaatcgaagcttcacaatacag
agtcagataaagaagacttgaagagccaaatagaggatttgaagaaagaattagctagtaaagaatcaaggcgccctggtcaaccaccaccaaacca
agatctcaagatgtctagccacaccggaaccaagattgtagacgcggagatagacattaagataatgggatgggatgttatgattcgtgtacaatctaa
taaaaagaatcatccagccgcaaggtttatggcggccctcatggaactagacctagatgtgaaccatgccagtgtttcattggtgaacgagttgatgatc
cagcaagccacagtgaaaatgagtagccgtcattacactgaagagcagcttaggatagcattgatgtcaagaattgctgaaacgcgctaaaaaagacc

FIG. 6A ctagaaagtagatagaactcaaagaaagcatgtgggctttgatggcgctctggttgctgcagctctatgtaatgttttgttatgaattagagatttcatc
aggctatcttcgtgttatttttcgaacttgtaccttaggtggttgtcgaaatattcttgtacataaatgttattacccgaaaactcaacataatcgggctttag
ctcatgtaattaaacatatattccaactccgtcttgtctgttagattgcatctatcattatgtattctttgtccatgcataaatgaagaaatttgatggcaggt
gaatttgattttgaagcaaatgtgatttactgtcgtgctgcttattcttatacccaatttttgagctgcattaggattgtgtgaagtactttaagctattcattc
atgagaaaaatgtgaaagagatcatcatttcagaaatatgcactatttctccaattcaaacttcatgttcaaattgtattaaataattgtattggaggtcatt
gcttacgacctttatgcatcacatttgactaaaaacaataacggattatttcatgagaatatttggatttacatatacacctcagaaaaactatcatctttc
atttgagttttaatgtcatactccatccgactcaatttaatttgcgccgaagaatgccaaaaaagtttcacatttatggtcaatagatgagtaatctcctta
taaggcttggattatcctctttcctaatgctcaaaaggtgtaagtttagccatgacctaattttatatatactttttttttgacatttctttaatcttaattttcat
acgacatatttaagattataaaattaaataatatttaatacattctatcttgtgtcaagttaaatgagacaaacaaattataacaaaggaagcatcaaata
aaataggaaagaaggaaaaagggatttcgtaaaagagcgataagataaggtgatagtttgatagactagattggactagatgcaacagcaaaatag
aacaggaaactacaaggaactagtccatttattcatttggctgcttgctcgtttatattgtgaattgtatatctccacatatttattctaataaagatatcag
gaagaaggcatgtgtcttattattttccttaggagaatacactgaacttggttcttcttttggtccctattgtctactatagaccaatgtatattttccataat
agtattggcataacatgctaaagtattttccataatagtattggcaagaaacgccatgaatatcatgtaggttgaaactgacagcaacgtttcaaattcac
ttcatttgaactttcacttcacccaagtacagtctccccgtccgaagcaggattttcatcaaagagatgcaacatttaccataaataaattttctcccccca
tccctctctctctatatattagtaactttggatccagatgaacccttttccgcctcacaagtttcacccaagttccaagtatatgttactctagaagttttaact
ttcttttagtaattctttgttaatatgttgtccctatactagtatctggacatgccactactgaaaaattcaaaatttaccttcattctttaaggtaatttacaa
ttcaatctttaaggttttatattgaccttattatattttaaagttatgaatttatatttattattattactttctatatttttaaataagtgacatttagtcttttca
ttttatttctaaataacttggtgttttagataattaagaagatattaatgatgttattataagtttaccacttttttaaataaagaaagttttacatgacttaagg
agtactaagaattacatcatttccaaagaaatattaagaataagttggtaaaaatactatttatttaaaaataaaaaaaaataattttaacaaactaataca
tataaatttatatttcctattgaaaatacaattcatactaatctcaacgccgctcggtaaaattagatccgcttcactttaactgctaattattgaataaagtg
tagggacaaatttgatgtaaataaaatcatctactccactaatatattaatttgttttaatttaatatatatttttcatacactagacaacaaagaattgtga
cgtgacgcaaatttggtggaagtggacatgcagacaaaaaagatcatgtgttac SEQ ID No. 10:

>c_annuum_CDS
atgactgattacagcttgcccaccatgaatctctggaataacagtactactgatgacaacgtttctatgatggaggcttttatgtcttccgatctttcttttg
gggtggtactactacttctagtgctactgctactgctgctgctcttgctaatcccaattatacttcaactgtttaccctcctcctggcgcttcttgtgcatcttc
cgtaacggctacagctgctgctgtgactgttgatgcgtcaaaaaccatgccattttcaaccaggagacgctacagcagcgtcttcagaccctaatagac
ggtgctcgtgagacgtggacgtatgctatcttctggcagtcgtctgatttagatttctcgagtccgtctgtgttgggttggggtgatggttattacaaagg
ggaggaggataaaaacaagaggaaattatctgtttcttctccggcttatattgctgagcaggaacatcggaagaaggttcttagagagctgaattcgtt
gatttcagggacacaaactggtacagacgatgctgttgatgaagaagttaccgataccgaatggttctttcttatctccatgactcaatcttttgtcaacgg
gaacgggcttccgggccaggctatgtgcagttccagcccgatttgggttgccggagtagagaaattggctgcttctcactgtgaacgggctcggcagg
cccaaggggttcgggcttcagacgatggtgtgtatcccttcagctaacggtgttgttgaattgggttcgacggagttgattatccagagttctgatctgatg
aataaggttagagtactgttcaatttcaataatgatttggggtcaggttcatgggctgtgcagccggagagcgatccgtcagcgctttggttgacggag
ccatcttcctcaggtatggaagttagagagtctttaaatacagttcaaacaagttcaattccatcaagtaatagtaataagcaaattgcgtatggaaatga
gaacaatgatcatccatctggaaatgggaatggtcatagttcttataatcagcagcatcctcatcaacaaacacaaggattttcacgaaggagttaaac
ttttcggactttgggttcgatggaagtagtaataggaacgggaattcatcgctctcttgcaagcctgagtctggggaaatcttgaattttggtgatagtac
gaagaaaagtgcttgtagtgcaaatgggaacttgttttcgggccattcccaatttggggcaggtgaggagaacaagaacaagaccaagaaaaggtca
gctacttccaggggaagcaatgaagaaggaatgctttcatttgtttcgggtacagttttgccttcttccggtatgaagtcaggcggaggcgaagactctg
accattcagatcttgaagcttcggtggtgaaagaagctgatagtagtagagttgtagaaccggaaaagaagccaaggaagcgaggaaggaagcctg
ctaatggaagggaggaaccttttgaatcatgttgaggcagagaggcaaggagggagaaattgaaccaaagattctacgcgcttagagctgttgtacc
gaatgtgtctaagatggacaaggcatcacttcttggagatgcaatttcatacataaatgagttgaaatcgaagcttcacaatacagagtcagataaaga
agacttgaagagccaaatagaggatttgaagaaagaattagctagtaaagaatcaaggcgccctggtcaaccaccaccaaaccaagatctcaagatg
tctagccacaccggaaccaagattgtagacgcggagatagacattaagataatgggatgggatgttatgattcgtgtacaatctaataaaaagaatcat
ccagccgcaaggtttatggcggcctcatggaactagacctagatgtgaaccatgccagtgtttcattggtgaacgagttgatgatccagcaagccaca
gtgaaaatgagtagccgtcattacactgaagagcagcttaggatagcattgatgtcaagaattgctgaaacgcgctaa SEQ ID No. 11:

>c_annuum_AA
MTDYSLPTMNLWNNSTTDDNVSMMEAFMSSDLSFWGGTTTSSATATAAALANPNYTSTVYPPPGASCASSVTA
TAAAVTVDASKTMPFFNQETLQQRLQTLIDGARETWTYAIFWQSSDLDFSSPSVLGWGDGYYKGEEDKNKRKLS
VSSPAYIAEQEHRKKVLRELNSLISGTQTGTDDAVDEEVTDTEWFFLISMTQSFVNGNGLPGQAMCSSSPIWVAGV
EKLAASHCERARQAQGFGLQTMVCIPSANGVVELGSTELIIQSSDLMNKVRVLFNFNNDLGSGSWAVQPESDPSA
LWLTEPSSSGMEVRESLNTVQTSSIPSSNSNKQIAYGNENNDHPSGNGNGHSSYNQQHPHQQTQGFFTKELNFS
DFGFDGSSNRNGNSSLSCKPESGEILNFGDSTKKSACSANGNLFSGHSQFGAGEENKNKTKKRSATSRGSNEEGM
LSFVSGTVLPSSGMKSGGGEDSDHSDLEASVVKEADSSRVVEPEKKPRKRGRKPANGREEPLNHVEAERQRREKL
NQRFYALRAVVPNVSKMDKASLLGDAISYINELKSKLHNTESDKEDLKSQIEDLKKELASKESRRPGQPPPNQDLK
MSSHTGTKIVDAEIDIKIMGWDVMIRVQSNKKNHPAARFMAALMELDLDVNHASVSLVNELMIQQATVKMSSRH
YTEEQLRIALMSRIAETR SEQ ID No. 12:

> c_sativus _gDNA
ttttaaatttgaggcgtcataaagttagtttatatgtgagaggtatcttgttgaattttttaagtttttaaaattttttattcaataaagttctaaaatttgctct
attttttttctgtttggcatccaactgtagacatactttttcaaaattttaacactcggtttggtatttgaatttaattaaataaagctatactcaacaaaaaaa
tatattgttttttaaagtagttaattaagttggttaataccataaagtaagcacaaagcaatatgtgacaaataagtgataaataagtaatttgtcttacgg
gtatttgtgacaaataagtttataaggataactcaaccatcttagacaacctatcaacatcaacttgcctaaggtgaatgttaatattgattgttaggggtg
agtgtcacttgccattgaagttgattatcaaaggtgattttcattgcagtttatcatataagcagtagttggagtctgaaattgaaggtggttatcgaagtt
gataatcaaaaagtgattttctcaaagtttgtagtcatagcttggaattcatcgtgtaaacgtggtcatcaaagttggctttttttggagtttcctattggag
atagttaccatagcccaaaattagttgttggaggtggtcacataaaggtatctagtcgttaggtcagtttgtcatcgaaggtggttgccagaccttgaaat
cgatcatcaaagttggttatctgagtgtggtaatggtaattgatcgttaatctattagaaaaactggagagagcttcatcaacctataaagttagtgga
ccaaagagaactcaaactcaacttatattttgatgtgttaactccccctaaaataaaacaaacgaaacaaaaaaaaaaaatcataaagacaaaaatgaaa
aaatggagtaccatcattgtactaaaaaaatatattttaacaaaagaaaaaatcaatgactacaaataaatttttaaaacactagatttaaaaaaaaaaat
caaagaacaaaaatagaagatatttatatatatatatatttaaaaaagaaaattaatagatattataatgaggcttagtattttcaaaatcctgttttaggg
caaaaaaaagagggaaaaataaaacaacttccgtctttgattcacaaacaagagacgtgtcatgttctcattagctaaaaccggaaaaaaagcgatg
agtaaaaaagtcataaaaacggttaaccctcaacgcctctcaagggttcttcacgtgccagtcacgtggaaggaagggaagcgaaccgggtctaaga
aaaccgcactatctggggtaagtactattagtataattgtactataagcgcggagttgagaaagacgccggcttttgaacgatttaatcggcgatctaa
agaagaagcctcttggttccttcttctcctcttcgcttctctgttaaatgttcatcacaaataaatcccataccaatcgcccgacatttctctcactccacaatc
ggagaccaaagattattcctttttttcccatttctatttcttccaatctcaatcgcatgacggattatcgtttgtcgacgatgaatctctggactgacgagaac
gcgtcggttatggacgctttcatgaattccgatctgtcttcctactgggctccgtcagccgcctcctctcactctcttcaccacccaccgccacctcagtcctc
cgcctccacatccactcccccgccggacgcacctaagtccctccccgttttcaatcaggagactctgcagcagcggctccaggcgctgatcgacggtgct
agggagagttggacttatgcgattttctggcagtcgtcttatgattattctggtgggtctgttttggggtgggtgatgggtattacaaaggagaggaa
gataaaggaaagggaaaagcgaaaatggtgtcgtcagcggcggagcaggctcaccggaagaaggttttacgggagcttaactctttgatttctggct
ctgccgccggacctgacgatgcggtggatgaggaggttacggatacggagtggttctttttggtttcgatgactcagtcgtttgttaatggtgttgggtt
accgagtcaagcgttttaccactcgacgccgatttgggtctctggtgccgatcggctgtcggcgtctgcctgtgaacgagctagacaggggagggtttt
gggttacagacgatggtctgtattccatcgcctaacggtgttgtggaaatgggttcgacggaattgattcatcgaacgtcggatttgatgaataaggtca
agattctgttcaatttcaacaatctcgaaacgagttcttggatttcgggaactaccgccgccgcatccgctgccgacgaaggggaaaacgacccgtcgtc
gatgtggatcagtgagccatcgagtacaatcgagatgaaggattcaatcaccaccactgttccttccagcaacgttccggcaaagccaatccgttcgga
aaatcccagtacaagtagcttaacggaaaatatgagcacgattcaacaatcccatcataaacagagccaaagcttcttaaatttctccgattacggcttc
gaatcaaatcccacaaagaacaccaccgctaccgccaccgcaaccaccagcaccacccccatcattcaagccggaatccggcgggatgctgaatttcgg
caacgggagcctcttctccggccattcacagtacgtaacaaacgaacagaacgagaaaaagagatcccctgcttctcgaagtagcaacgacgaaggg
atcctctcttttcacctccggcgtgatcttaccctcttccggtaaggtaaaatccggtgattcagaccattcagatctcgaagcatcagcgatcagagaagt ggatagctgtacaaaatcattagaacccgaaaaacgtccaagaaaaagaggtagaaaaccagcaaacggaagagaagagccattgaatcacgtaga
agcagagagacaacggcgagagaaattaaaccagaaattctacgctctccgagctgtagttccaaacgtatctaagatggacaaagcctcactactag
gtgacgcggtttcgtacataaacgagctcaaatcgaagctccaaatggcagaatcggagaaaacagatatgggaaaacatctagaattgctgaagaa
ggagatgggaggaaaagatttaggatgttactcaaacccaaatgatgaagatctgaaaacagggaaaagaaaggtaatggatatggagattgaagt
taaaatcatgggttgggatgcgatgataaggattcaaagcaacaagaagaatcatccggcggcgaggttgatgacggcgtttaaggatttggatttag
aaatgcttcacgcgagtgtttctgtagtgaatgatttgatgattcaacaagcaacagtgaagatggggagcagattttacacacaagagcagcttaaaa
tggctcttgtcgcccgagtcggcggtggtggaagtggaggcggcggtggaatcatgtaaatgggggttaggggacattttgaagctcccaattagtag
agtttagttgagggaatctgatttagtattgtgtaatataaatgttggtaaattattttttgataattctcttgttgttcatcttttgttgttagagtaatttggga
gttcttctatatgtagttttttgtttattaaatatgaaatctaatagaagtaaagatcaaagaccttcaaactttgtgtttgatcatttcaattctccttctttcctt
tttttttttttttttgttttttgtttttgttttttagggttttgtttgaactagtaggtctagtttagggaaaatctaggtttgatcggaaattaaggactaaccttta
acctttcttggtacaaacttagttaaacctacatgtcaatagacttaaaagatttagtattaaggtccaaactttcccacggttgagatcgaaagcccctg
atataagaacaactcataaaatttgacatttgattaggttattaagtggatttcaatgggggatcgagacctactctcttaggtcaacattttttcataaatata
taagttggttagtctagatttgtaaattttaattgggtttagttgtttatgtatggagataggtaattgaacttctcatattgagttatatactcctacaagta
aagggagaaactcccaatagatattggttgtgttggaaaggttatgaatcgattaataagtcaattaccattatcttgattttgaacgccaatgcatcaca
tgcatatatatatatatatattgtcggctagtacacgaccaattaatgtttggataaagttctttccagaatcatcctatttttcaagactcactaaaatccttc
agatatatggttccacaattggtcctatgtacaacagtgtattgaactacttcaacacgatgttcgtacaacaatacccacaactcatttttgcactccatag
caaaaaataatatattatgttaaggacaaccccttaggtaaattgctttgaatgagttaatcaatcatttatccttgtggatcaacattaatcctctcatacc
tactaattggtatgcttgagatgcattttctcgagcacctatagaagacgttatatatagactggattaaaagggacactcatcctaaaattaggattcatt
tcttgtagcaaatattcacttgtagcatacgatatctaaagggactggcgtaagttttctactgcgggtacgtttccataatgatggtgtcttttcaatatca
aactttactgttcaccatcttgaactagccatcctttagagagtattgttaaaagatatcaattcctaatgaaatggatgtcgcagtggcccactaaaagtc
tttaattgatattacaatctttatgctagttgagctatgctcgatttatcattttgtatacaataagctctaacaagttagttaggttccatcctttatatatagt
ttgtacacattattattttagatgcatgccacatgcctaaaccttcaaatgattggttactatattggagagtttaagctacctctcatacatagaaatgtta
agtagattcaatgaagtttagaaattttaattttgaaaat

SEQ ID No. 13:

> c_sativus _CDS
atgacggattatcgtttgtcgacgatgaatctctggactgacgagaacgcgtcggttatggacgctttcatgaattccgatctgtcttcctactgggctcc
gtcagccgcctcctctcactctcttcaccacccaccgccacctcagtcctccgcctccacatccactcccccgccggacgcacctaagtccctccccgttttc
aatcaggagactctgcagcagcggctccaggcgctgatcgacggtgctagggagagttggacttatgcgattttctggcagtcgtcttatgattattctg
gtgggtctgttttggggtggggtgatgggtattacaaaggagaggaagataaaggaaagggaaaagcgaaatggtgtcgtcagcggcggagcag
gctcaccggaagaaggttttacgggagcttaactctttgatttctggctctgccgccggacctgacgatgcggtggatgaggaggttacggatacgga
gtggttcttttttggtttcgatgactcagtcgtttgttaatggtgttgggttaccgagtcaagcgttttaccactcgacgccgatttgggtctctggtgccgat
cggctgtcggcgtctgcctgtgaacgagctagacaggggagggttttgggttacagacgatggtctgtattccatcgcctaacggtgttgtggaaatg
ggttcgacggaattgattcatcgaacgtcggatttgatgaataaggtcaagattctgttcaatttcaacaatctcgaaacgagttcttggatttcgggaac
taccgccgccgcatccgctgccgacgaaggggaaaacgacccgtcgtcgatgtggatcagtgagccatcgagtacaatcgagatgaaggattcaatc
accaccactgttccttccagcaacgttccggcaaagccaatccgttcggaaaatcccagtacaagtagcttaacggaaaatatgagcacgattcaacaat
cccatcataaacagagccaaagcttcttaaatttctccgattacggcttcgaatcaaatcccacaaagaacaccaccgctaccgccaccgcaaccaccag
caccaccccatcattcaagccggaatccggcgggatgctgaatttcggcaacgggagcctcttctccggccattcacagtacgtaacaaacgaacagaa
cgagaaaaagagatcccctgcttctcgaagtagcaacgacgaagggatcctctcttttcacctccggcgtgatcttaccctcttccggtaaggtaaaatcc
ggtgattcagaccattcagatctcgaagcatcagcgatcagagaagtggatagctgtacaaaatcattagaacccgaaaaacgtccaagaaaaagag
gtagaaaaccagcaaacggaagagaagagccattgaatcacgtagaagcagagagacaacggcgagagaaattaaaccagaaattctacgctctcc
gagctgtagttccaaacgtatctaagatggacaaagcctcactactaggtgacgcggtttcgtacataaacgagctcaaatcgaagctccaaatggcag
aatcggagaaaacagatatgggaaaacatctagaattgctgaagaaggagatgggaggaaaagatttaggatgttactcaaacccaaatgatgaag
atctgaaaacagggaaaagaaaggtaatggatatggagattgaagttaaaatcatgggttgggatgcgatgataaggattcaaagcaacaagaaga
atcatccggcggcgaggttgatgacggcgtttaaggatttggatttagaaatgcttcacgcgagtgtttctgtagtgaatgatttgatgattcaacaagc aacagtgaagatgggagcagattttacacacaagagcagcttaaaatggctcttgtcgcccgagtcggcggtggtggaagtggaggcggcggtgg
aatcatgtaa

SEQ ID No. 14:

>c_sativus_AA
MTDYRLSTMNLWTDENASVMDAFMNSDLSSYWAPSAASSHSLHHPPPPQSSASTSTPPPDAPKSLPVFNQETL
QQRLQALIDGARESWTYAIFWQSSYDYSGGSVLGWGDGYYKGEEDKGKGKAKMVSSAAEQAHRKKVLRELNSLI
SGSAAGPDDAVDEEVTDTEWFFLVSMTQSFVNGVGLPSQAFYHSTPIWVSGADRLSASACERARQGRVFGLQTM
VCIPSPNGVVEMGSTELIHRTSDLMNKVKILFNFNNLETSSWISGTTAAASAADEGENDPSSMWISEPSSTIEMKDSI
TTTVPSSNVPAKPIRSENPSTSSLTENMSTIQQSHHKQSQSFLNFSDYGFESNPTKNTTATATATTSTTPSFKPESG
GMLNFGNGSLFSGHSQYVTNEQNEKKRSPASRSSNDEGILSFTSGVILPSSGKVKSGDSDHSDLEASAIREVDSCT
KSLEPEKRPRKRGRKPANGREEPLNHVEAERQRREKLNQKFYALRAVVPNVSKMDKASLLGDAVSYINELKSKLQ
MAESEKTDMGKHLELLKKEMGGKDLGCYSNPNDEDLKTGKRKVMDMEIEVKIMGWDAMIRIQSNKKNHPAARL
MTAFKDLDLEMLHASVSVVNDLMIQQATVKMGSRFYTQEQLKMALVARVGGGGSGGGGGIM

SEQ ID No. 15:

>c_melo_gDNA
ttcctgtcctaaggttgcagtaattttagattttactttgagataaaaattgtaaaaattaaatgggtttagtattacaataatcgatttaactataaaattctt
aaataataaattaatatattttaattatattatgtaagttaggctttgtaagttatttattctcttacattaattatagtatgtgttttttatatgatttgaatttc
aattcattttattgtatttaaattatctgataaaagtttaggattttttaataaaattaaatcaattactatagaagattaaaaatattttaatttaaaaatgag
ttattttgaaaaagaaataaaggatatatatatatacatattgaaataagtgagagtattactttatttttgagtaaagtgggaaaataaatttttgcgtag
aaaatttgctaacttttcaaaaaagcatttgtcgtctttttctctttttcttcattttttgtaatttttgttgttttttttccctctcattccttaatcattttattgcaatgttt
ttcccttaaaaagaagcatagctcaattttttaaatattttgataatgtgtagaattgaataatcaaatctctaatattcatgctaaccatttaactatttttg
atagggttgaaagtatgttaggttttatgagtatttactatatattaacaattgggctcaattttataaatttgtaatttgatggtttgagttttaaaagga
aagaaatggttggaatgttaataatcaatatggtttagattaaagtaatcgatttcacaaaagttggagttgagctagggatatgacatgcattcaaccc
acctaggcttgaggggagacgagagtttggaccaaatgtccaaatatgaaccgatcaattttaccttggtcgagacatacccacatttgattaaata
ggcatgttaaacgtgtaggacaacatattgagtttgagaaaaagcctaatctaactccaaaacccaatttaaatgtcttaggtcataagtaagttaacta
tatcatccaaactcttgcgagttgcgacaacttaaagagtttaattagttacaatcattattgtaatttttttaaatttgaggcatcatatgttgttactcgatg
aggctgtttagggcgttgagttgatgtagggtgttgttaagaagcaaagtaatatgtcttatggatacttgtgacaaataagtttataaggatgatccaa
ccaatcttagacaacttctcaacatcaaattgccttaggtgaatgttagtatatattgattgttagaggtagttgtcactatttgtcattgaagttgattatca
aaggtgattctcgttgaagtttatcatagaggtgggttgttggagcccaaagttaaaggtggttttcgaagttgataatcaaaggcgattttcgctaaag
tttgtagtcatagcttggaattcatcgcatggacgtagtcatcaaagttggctttcgttggatttgttatcagagatgattacaggctcgaaattagtggtt
ggaggtggtcgtgcaaaggtaatctagttgtcatagttttttcatcgaaggtggttgtaggaccctgaaatcgattgtcaaagttggaggtgtgaaagtg
gctgttgtcggagtcggatcctagagtttggtaatgggtaattgtcataatggtaatcgatcgtcgaatccattgaaaacattggaaagaactccaccaa
catgtaaagttggtaggccaaacgaaactcaaacccatcttatattgatgtgcaaaacatctctaggataaaacaaaccaaactaataaatcataaagac
aaaaatgaaaaatgagagtaccaaaaaaaaaaaaaagagcaataacttcaaataagttttaaaacactagatttaaaaaaaaaatcaaagaacaa
aaatagaagatattttaatctctacaaaaaaaaaaaaaagaaaaaaagaaaattatagatattaataattgtaatgaggcttagtattttcaaaatcctc
atttagaggaaaaaaaagggagaaaataaactaacttccgtctttgtttcacaaacaagacacgcgtcatattctcattagctaaaaccgcaaaaaaa
gcaatcagtcaaaagtcttaaaaacggttaacactctaaacgcctctcaagaattcttcacgtgtcagtcacatggaaaagaaaccggccgaaccggg
tcgaagtaaaccgcgttatctggcgaagtacaaagtataatagtactataaccgcggagttgaaaaagacgccggcttttgaacgattaaatcggcga
tctaaagaagaaggctcttggttccttcttcctctgtgttcgctccttttcttaaatgttcatcacaaataaatcccaatccaatcgcccgacatttctctcactc
cacaatcggagacagaagattattccttttttccgatttctgtttcttccaatctcaatcgcatgacggattatcgtttgtcgacgatgaatctctggactgac
gagaacgcgtcggtgatggacgctttcatgaattccgatctctcttcctactgggctccatcagccgcctcctctcactctcttcaccatccaccaccacctc
agtcctccgcctcaacgtccactccccgccggacccacctaagtcctcccgttttcaatcaggagactctgcagcagcggctccaggcgctgattga
cggtgctagggagagttggacttatgcgattttctggcagtcatcttatgattattccggtgggtctgttttggggtggggtgatgggtattacaaagga
gaggaagataaaggaaaggggaaagcgaaaatggtgtcgtcagcggcagagcaggctcaccggaagaaggttttacgggagcttaactctttgatt tctggctctgccgctggaccggacgatgcggtggatgaggaggttacggatacagagtggttcttttggtttcgatgactcagtcgtttgttaatggtgt
tgggttaccgagtcaggcgttttaccactcgacgccgatttgggtctctggtgccgatcggctgtcggcgtctgcctgtgaacgagctagacaggggag
ggttttttgggttacagacgatggtctgtattccatcgcctaacggtgttgtggaaatgggttcgacggaattgattcatcgaacatcggatttgatgaata
aggtcaaaattctgttcaatttcaacaatctcgagacgagttcttggatttcgggaactaccgccgccgcatccgctgcagacgaaggggaaaacgacc
cgtcgtcgatgtggatcagtgagccatcagtacaatcgagatgaaggattcaattaccaccaccgtcccttccagcaacgttccggcaaagccaatccg
atccgaaaatcccagttcaagtagcttaacgaaaatatgagcacgattcaacaatcccatcataaacagagccaaagcttcttaaatttctccgattacg
gcttcgagtcaaatccctcaaagaacaccaccgccaccgccaccgtaaccaccagcaccactccatcattcaagccggaatccggcgggatgctgaatt
ttggaaacggaagcctcttctccggccattcacagtacgtaacaaacgaacagaacgaagaaaagagatcccctgcttctcgaagtagcaacgacgaa
gggatcctctctttcacctccggcgtgatcttaccctcttccggtaaggtaaaatcaggcgattcggaccactcagatctcgaagcatcagtgatcagaga
agtagatagctgtacaaaatcattagaacccgaaaaacgtccaagaaaaagaggtagaaaaccagcaaacggaagagaagagccattgaatcacgt
agaagcagagagacaacggcgagagaaattaaaccagaaattctacgctctacgagctgtagttccaaacgtatctaaaatggacaaagcctcactac
tcggtgacgccgtttcgtacataaacgagctgaaatcgaagctccaaatggcagaatcggagaaaacagatatgggaaaacatctagaattgctgaa
gaaggagatggggaggaaagatgtaggatgttacacaaacccaaatgatgaagatctgaaaatagggaaaagaaaggtaatggatatggagattg
aagttaaaatcatggggttgggatgcgatgatcagaattcaaagcaacaagaagaatcatccggcggcgaggttgatgacggcgtttaaggatttggat
ttagaaatgcttcacgccagtgtttctgtagtgaatgatttgatgattcaacaagcaacagtgaagatggggagcagattttacacacaagagcagctta
aaatggctcttgtggcccgagtcggtggtggtggtggaggcggaagcggcggtggaatgatgtaaatgggggttaggggacattttgaagctcccaa
gtagtagagattagttgagggaatataaatctgatttagtattgtgtaatattaatgttggtaaattattttttgataattttgttgttcatctttttgttgttaga
gtaatttgggagttcttcttctatatatatgtagttttgttgattaaatatcaaatctaatagaagtgaagatcaaagaccttcaaactttgtgtttgatgat
ttcagttctctttcctttgttttaggtttgtttgaagtaaaaatctaggtttgattggaaatttaggactaaccttaacctcccagctcagtacaaaccta
gttaaacctaaatgtcaatggacctaagatttggtattgggtccacatttcgtgtggttgagatagaaaaccccaactttcatataagaacaacccatata
aaattcgtcatttgattaggttattcgataagtggatttcaaaagggatcgggagaataactagtctcttaagtcaacattttttcatatatacataagttgg
tcgatctagattttctaaattttaagttggtttagttgtttttgtacaatagggaacgtgcgtgtgcgtgtgcgcgtgcgtgtgtgtgtggttgtgtgtgtgt
gtgtgtcgctagttgtgtgtgtgtgtggttcgctaatacannnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnntcaatggactgacgtatttatttactaggtcataatgatggtgttttccaaaatcaaac
tttgctgttcaatatcttagactagccatcctttagaggagattgttaaaaaatcatcaattactaataaaaaaaagactattgcagtggcccactggaagt
ctttagttgatactacaatctttatgctagttaagctacgctcaatttgtccgtttgtatacaatgaactctagcaaattagcttacatcatttatacatactt
aaatgattggttactgtctatcggggagagtttaacctagctcttatacatagaaattttaagcaggtttaacgaaagttgaagtttagaaaatttaatttt
gaaaataatcatataaacatgcatgtcacacatgtttattgatatgctaagtcaatgagctatagagagttaggttcatagccacataaataaaacctata
actcttagttttatgttttcgaaatttatggccgtttcttactatttaaactttttcaaaagaaaaaatttgaactcattaaattctaacaacaaaaacatgtttt
tgaaaacgaaataaaaatagataataaaacacaaaaaacttatagatgaaaatagtgtttataaggttacttaaaaaaaaaccaaacaatcatcaaata
cgaagtttttgaaatttgatttagatttattcgatgtgtggtaataattgggatgtagaaagataagctatggatgatagtgaagaattgaaggtgacct
tacacttcatatatggacataaaaaaggaccattttcatagaatcttcaagaagatattgatggagataattttctctcttttttgtgaccccttcttcatataa
agtaattccattgttgaagttaaatggtaaaaagaaaaaaaaaaagaacttttttattattgtataaaacaatgatttagattttgaattttatttgtgaca
atttggtcattttgaatatctaaactacgttggttatttttatcgtcac SEQ ID No. 16:

>c_melo_CDS
atgacggattatcgtttgtcgacgatgaatctctggactgacgagaacgcgtcggtgatggacgctttcatgaattccgatctctcttcctactgggctcc
atcagccgcctcctctcactctcttcaccatccaccaccacctcagtcctccgcctcaacgtccactcccccgccggacccacctaagtcctcccgttttc
aatcaggagactctgcagcagcggctccaggcgctgattgacggtgctagggagagttggacttatgcgattttctggcagtcatcttatgattattccg
gtgggtctgttttggggtggggtgatgggtattacaaaggagaggaagataaaggaaggggaaagcgaaatggtgtcgtcagcggcagagcag
gctcaccggaagaaggttttacgggagcttaactctttgatttctggctctgccgctggaccggacgatgcggtggatgaggaggttacggatacaga
gtggttcttttggtttcgatgactcagtcgtttgttaatggtgttgggttaccgagtcaggcgttttaccactcgacgccgatttgggtctctggtgccgat

FIG. 6F cggctgtcggcgtctgcctgtgaacgagctagacaggggagggttttttgggttacagacgatggtctgtattccatcgcctaacggtgttgtggaaatg
ggttcgacggaattgattcatcgaacatcggatttgatgaataaggtcaaaattctgttcaatttcaacaatctcgagacgagttcttggatttcgggaac
taccgccgccgcatccgctgcagacgaaggggaaaacgacccgtcgtcgatgtggatcagtgagccatctagtacaatcgagatgaaggattcaatta
ccaccaccgtcccttccagcaacgttccggcaaagccaatccgatccgaaaatcccagttcaagtagcttaacggaaaatatgagcacgattcaacaat
cccatcataaacagagccaaagcttcttaaatttctccgattacggcttcgagtcaaatccctcaaagaacaccaccgccaccgccaccgtaaccaccag
caccactccatcattcaagccggaatccggcgggatgctgaattttggaaacggaagcctcttctccggccattcacagtacgtaacaaacgaacagaa
cgaagaaaagagatcccctgcttctcgaagtagcaacgacgaagggatcctctctttcacctccggcgtgatcttaccctcttccggtaaggtaaaatca
ggcgattcggaccactcagatctcgaagcatcagtgatcagagaagtagatagctgtacaaaatcattagaacccgaaaaacgtccaagaaaaagag
gtagaaaaccagcaaacggaagagaagagccattgaatcacgtagaagcagagagacaacggcgagagaaattaaaccagaaattctacgctctac
gagctgtagttccaaacgtatctaaaatggacaaagcctcactactcggtgacgccgtttcgtacataaacgagctgaaatcgaagctccaaatggcag
aatcggagaaaacagatatgggaaaacatctagaattgctgaagaaggagatgggagggaaagatgtaggatgttacacaaacccaaatgatgaa
gatctgaaaatagggaaaagaaaggtaatggatatggagattgaagttaaaatcatgggttgggatgcgatgatcagaattcaaagcaacaagaag
aatcatccggcggcgaggttgatgacggcgtttaaggatttggatttagaaatgcttcacgccagtgtttctgtagtgaatgatttgatgattcaacaag
caacagtgaagatggggagcagattttacacacaagagcagcttaaaatggctcttgtggcccgagtcggtggtggtggtggaggcggaagcggcg
gtggaatgatgtaa

SEQ ID No. 17:

>c_melo_AA
MTDYRLSTMNLWTDENASVMDAFMNSDLSSYWAPSAASSHSLHHPPPPQSSASTSTPPPDPPKSLPVFNQETL
QQRLQALIDGARESWTYAIFWQSSYDYSGGSVLGWGDGYYKGEEDKGKGKAKMVSSAAEQAHRKKVLRELNSLI
SGSAAGPDDAVDEEVTDTEWFFLVSMTQSFVNGVGLPSQAFYHSTPIWVSGADRLSASACERARQGRVFGLQTM
VCIPSPNGVVEMGSTELIHRTSDLMNKVKILFNFNNLETSSWISGTTAAASAADEGENDPSSMWISEPSSTIEMKDSI
TTTVPSSNVPAKPIRSENPSSSSLTENMSTIQQSHHKQSQSFLNFSDYGFESNPSKNTTATATVTTSTTPSFKPESG
GMLNFGNGSLFSGHSQYVTNEQNEEKRSPASRSSNDEGILSFTSGVILPSSGKVKSGDSDHSDLEASVIREVDSCTK
SLEPEKRPRKRGRKPANGREEPLNHVEAERQRREKLNQKFYALRAVVPNVSKMDKASLLGDAVSYINELKSKLQM
AESEKTDMGKHLELLKKEMGGKDVGCYTNPNDEDLKIGKRKVMDMEIEVKIMGWDAMIRIQSNKKNHPAARLMT
AFKDLDLEMLHASVSVVNDLMIQQATVKMGSRFYTQEQLKMALVARVGGGGGGSGGGMM

SEQ ID No. 18:

>c_lanatus_gDNA
ttttatataaatactaaattgttataaattaaactacgttattactttgttttttatttcatctgcaaacattcaaaattgaaatccttctagtcacaagttaaaaa
aattgggagactataccaggtgtacagtgaaaggaaaattacaaggagtaaaaaaattaatattgaattttataaactatcttaacattttatttttatttt
ttattttgccaactacaacaaataagagaaattatgttaaattgcaaaactgctaaaaatatttaaaatcaatagcaaaatacaccgtctacatgcgaatg
tgggatcaaatctcccctgtttgaagtgaaaaaagttaaaggagcatttgactaaattaacaaagaaattttgttttcaaccaaaacaaatgttactctgt
tactttgttttgagtgaattgtgaaagtaagctaatgtgtagaaaatgtgataactttcaaaaaagcattcgtcgccttttatatttctacaatattgttcgt
ttcatttttatttattttttcatcccctccttccttaatataactattgcaaatttcttaaatgagtttaacaaccttcaatgcaagttttttctttttttttttttt
tacaatctgtgaagttgaaaaaattgatactatcaccttatattggcagtattaaccttatgccatatgagttatatttattttgataaatacttacaatatgtt
aatgattaagttcaattttatgtagtgtaaattaaattttaaatttaatttaatgaatattctgcttcctgaaacaacatgttggtcccacgggtggtatca
ggtggaggttgtctttggattgacaagcattggaagatttaaaagctcttcgttttccattcgggattgtcattctgtcacttttggtggaatctgattatgtt
gaagtgatcacgtcccttgcaagattgatagtgatctttcgaatattacatttgtttttgttgtgttttaaagctagatgaagaatttgggaacatccattt
tgctaagtgttcgaggtttagtaattatttggctgcacactcgctagctagattggttgtgtctccttttttgaattctttttttaggctcgaatttgacttcctcc
tccttggaaaggttttaattttagttcatgggggttctaatgtccctaagttgttagttgctgttattggtgaggttgattgtcagttgggggaaaaaaattttt
aatagtttagacctagttttacacctcatttggtaactatttggttttttttgaatgattttgctggttgagagagataagtgaaatttttatatatttgtaaata
gtttgatatttttttcatttataataatttctcttcaaaattcaatcaaattttttaaagtataaattaaaagaaagggatcataacaaatcactcatttga
aatacaaaaataaattttgcactatatatatataaactcaacatctcttataagataaagcaaaataactaaataaaataaattgttttcaaatataagaaa
atgaacaaaaacatttataactacaatcaaattttactgtctatttgcgatagatctcgatctattgtagatagattgtaatattttgttatttttttaaatatat tctgcaactttatcatttaaaataattttttcaaataaaaatttagaaacaaaattgttgattgcaagtaagtacatagactaaaaatatttgttaacaaaaa
aaaaaaaaaaaaacaatcaaagactttaaataattttttaaaataaaaattgcagagagattagaaaaaaaatcaaagaacagaaatggtagatatttt
agctttttttaaaaaaagaaaaataatagatattttaatatggcgtagtattttcaaaagcgatttatttggagcaaaaaaaggaaagaataaaaccactt
cagtctttgattaacaaatcagacacgtgtcaacctctcattagtggaaaatgcaaacaaaccgatcagtcaaaagtcttaaaaacggttaccccccaaa
gctcacaaacgaaacgcccccgatgatccttcacgtgcccgtcacgtggaaagaaacgaaccgaaccgggtctaaatgagccgcactctctggcagga
gtactagtatagtactacaagcgcggagttgaaaacgacgccggcttttgaacgattaaatcggcgatccaaagaagaagcctcttggttccttcttcc
cctgttcgctcctctgtaaatgttcatcacaaataaatcccaatcaatcgcccgacatttctctcactccacaattggagacccagaattattctctttttccc
attctgtttcttctcgaatcccaatcgcatgacggattatcgtttgtcgacgatgaatctctggactgacgaaaacgcgtcggtgatggacgctttcatgaa
ctccgatctgtcctcttactgggctccatctgccgcctcctctcactctcttcaccacccaccgccgcctcagtcctccgcctccacctccactcccccaccgg
acccgcccaagtccctgcctgttttcaatcaggagactctgcagcagcggctccaggcgctgatcgatggcgctagggagagttggacttacgcgattt
tctggcagtcgtcctatgattattccggtgcgtcggttttagggtggggagatgggtattacaaagggggaggaggataaagggaagggaaaagcga
aaatggtgtcgtcggcggcagagcaggctcatcggaagaaggttttacgggagcttaactctttaatttctggctccgctgccggaccggacgatgcg
gtggatgaggaggttacggatacggagtggttcttttggtttcgatgactcagtcttttgataatggagtttggttaccgagtcaggcgttttacaactc
gacgccgatttgggtttctggcgccgatcggctgtcggcgtctgcctgtgaacgggccagacaggggagggttttgggttacagacgatggtctgtat
tccatcgccaaacggagttgtggaaatgggttcgacggaattgattcatcgaacgtcggatttgatgaacaaggtcaagattctgttcaatttcaacaat
ctcgaaacgagttcttggatatcgggaaccaccgccgccgatgaaggggaaaacgacccgtcgtcgatgtggatcagtgagccgtcgagtactatcg
agatgaaggattccattaccaccaccgtcccttccggcaacgtcccggcaaagccaatccattcggaaaatcccagttccagcagcttaacggaaaata
tcagcgcgatccaacaaccatcccatcaaaaacaaagccaaagcttcttaaatttctccgattacggcttcgaatcaaatccctcaaagaacaccaccgc
ggccgcaacaaccaccaccgccaccccatcattcaagccggaatccggcgggatgctgaatttcggcaacggaaacctcttctctagccattcacagta
tgtaacaaacgaacagaacgagaaaaagagatccctgcttctcggagtagcaacgacgaagggatcctctctttcacctctggcgtgatcttaccctcc
tccggtaaggtaaaatccggggactcagaccactcagatctcgaagcatcggtgatcagagaagtggatagctgtacaaaatcattagaacccgaaaa
acgtccaagaaaagaggtagaaaaccagcaaacggaagagaagagccattgaatcatgtagaagcagagagacaacggcgagagaagttgaac
cagaaattctacgctctccgagctgtagttccaaacgtatctaaaatggacaaggcctcactactgggagacgcggtttcttacatcaacgagctcaaat
caaagctccaaatagcggaaacggagaaaacagagatgggaaaacatttagaattgctgaagaaggagatgggagggaaagatttcgggaattac
ccgaacccaaatgatgaagatctgaaaataggggaaaagaaaggtaatggatatggagatcgaagttaaaatcatgggttgggatgcgatgataagg
attcaaagcagcaagaaaaatcatccggcggcaaggctgatggcggcgtttaaggatttagatttagaaatgcttcatgcgagtgtttctgtagtgaat
gatttgatgattcaacaggcaacggtgaagatggggagcagattttacacacaggagcagcttaaaatggctctcgtcgcccgagtcgggggcggcg
gcggcagcagccatggaatgatgtaaatgggttgtgtaattacaagtgggaggggacatttttgagggctcccaagtagagattagctgagggaatct
gattagtatgtgtaagataaaatgttggtaaattattttgatcattttgttgttgtttcatctttttttggttgttagagtaatttgggaagttctttgtgtagttt
ttgttaaatatcaaatctaatagaacagaagatgaaagaccttcaaactttgtgatgggttgctgtcttcaaaaatacccattgcgtttctctcttttttggta
gaagtttagtcggtaggtacttcttccactaaaccttaacctcacatagtatccacacgagttaagtctagagttctcaatagccatgagttgggcccaaa
ggccgagaagcccaactttcgtatctcaaatcagattaggtttaagacttaagtcatcctcaatttgtctgtttgtataataatatctatctattatgcttatt
aatgagctattataaggtaaggtaggttacatcatttatatttatagttagataatcactcaaagttaattttagatgcatgccgcacgtctaaacttgcaa
atgattggttaccatatttgggaggagttcataaaaatgttaaagtgaaaatatcatatacaacatgttgatgccacatgtttgtttcatatgctaattcagt
gtgagctatggtcagtttggttgagagttacactttataaaaactatttttttaaggcagtgtcttataacaaatttcattttaattttatgattttcaaattt
ttgaaatttatttccttctaattctaattttttctattatggtgttcacatgtctacatgaaactcttgaattccttgtcaaattctaataacaaaaacatgttttg
gaaactacatattttagtttttttctttaacaaaacatggaaacttaggatgaaagtagtgtttataaggttattttcaaaaacaaaatatcaaatgattat
caaatgagacccttaattcttaaaatttggctacgattttgaaatattattaaaaagtatataacaaaacaaaaacaaagaatgtcacgagtaaattttgttt
ctataaatttaaattaaaaaaaatttaaaaatagagatcaaataatcataaaaaagagcctatgtgtgattggcatgtaaaaagataaggttttgagcc
attgatgatagtggaagcttgtgaagaattaaagatgaccttacacttcatgtatggacataaaatgtcatcttcatagaatattcaagaagattttgata
aatataattttcactctttgtgacttctataaagtagttcaattgttgaagtaaaatggcaaaaaatggttttatgaactttcataaaattgataatcctcac
cccaattccatttgtttgtttttagtttttttaaaattaaacctatttttctatttcttgtaatgatttacatctttcttaggtgtaatcgttgaattcgtagtcaaat
tctaaaatgaaaaactaattttttttagttttcaaatttggcttgacttttaaaccattggtaaaaaattagataacaaaggcaaaatttggaattggaa
gtagtctctataaacttaattttcaaaaacaaaaaaagaccaaaaaccaaatggttaccaaacgggatagtaattttgaattgatttgtacaatttagtt
cttcttttgtaataattaagtgtgtcaattcttaatacgtaataactaacttaatatttgtagctaataaaataatatttttgtctttaattagtttataagatgt gactgtaagaaattctattaaatgtttttttttcaccatagaagttaaattgttaaataattgaaagtttatggattaaactttacataattgtttaaaaattaa
attattacaaaactagaaaatttagaggttaaaagtgtttttttttttttttttttttaacttaaaaggttttatttgga

SEQ ID No. 19:

>c_lanatus_CDS
atgacggattatcgtttgtcgacgatgaatctctggactgacgaaaacgcgtcggtgatggacgctttcatgaactccgatctgtcctcttactgggctcc
atctgccgcctcctctcactctcttcaccacccaccgccgcctcagtcctccgcctccacctccactcccccaccggacccgcccaagtccctgcctgttttc
aatcaggagactctgcagcagcggctccaggcgctgatcgatggcgctagggagagttggacttacgcgattttctggcagtcgtcctatgattattcc
ggtgcgtcggttttagggtggggagatgggtattacaaaggggaggaggataaagggaagggaaaagcgaaaatggtgtcgtcggcggcagagc
aggctcatcggaagaaggttttacgggagcttaactcttttaatttctggctccgctgccggaccggacgatgcggtggatgaggaggttacggatacg
gagtggttcttttggtttcgatgactcagtcttttgataatggagtttggttaccgagtcaggcgttttacaactcgacgccgatttgggtttctggcgccg
atcggctgtcggcgtctgcctgtgaacgggccagacaggggagggttttggggttacagacgatggtctgtattccatcgccaaacggagttgtggaa
atgggttcgacggaattgattcatcgaacgtcggatttgatgaacaaggtcaagattctgttcaatttcaacaatctcgaaacgagttcttggatatcggg
aaccaccgccgccgatgaaggggaaaacgacccgtcgtcgatgtggatcagtgagccgtcgagtactatcgagatgaaggattccattaccaccacc
gtcccttccggcaacgtcccggcaaagccaatccattcggaaaatcccagttccagcagcttaacggaaaatatcagcgcgatccaacaaccatcccat
caaaaacaaagccaaagcttcttaaatttctccgattacggcttcgaatcaaatccctcaaagaacaccaccgcggccgcaacaaccaccaccgccacc
ccatcattcaagccggaatccggcgggatgctgaatttcggcaacggaaacctcttctctagccattcacagtatgtaacaaacgaacagaacgagaaa
aagagatcccctgcttctcggagtagcaacgacgaagggatcctctcttcacctctggcgtgatcttaccctcctccggtaaggtaaaatccggggact
cagaccactcagatctcgaagcatcggtgatcagagaagtggatagctgtacaaaatcattagaacccgaaaaacgtccaagaaaaagaggtagaaa
accagcaaacggaagagaagagccattgaatcatgtagaagcagagagacaacggcgagagaagttgaaccagaaattctacgctctccgagctgt
agttccaaacgtatctaaaatggacaaggcctcactactgggagacgcggtttcttacatcaacgagctcaaatcaaagctccaaatagcggaaacgg
agaaaacagagatgggaaaacatttagaattgctgaagaaggagatgggagggaaagatttcgggaattacccgaacccaaatgatgaagatctga
aaatagggaaaagaaaggtaatggatatggagatcgaagttaaaatcatgggttgggatgcgatgataaggattcaaagcagcaagaaaaatcatc
cggcggcaaggctgatggcggcgtttaaggatttagatttagaaatgcttcatgcgagtgtttctgtagtgaatgatttgatgattcaacaggcaacggt
gaagatggggagcagattttacacacaggagcagcttaaaatggctctcgtcgcccgagtcgggggcggcggcggcagcagccatggaatgatgta
a

SEQ ID No. 20:

>c_lanatus_AA
MTDYRLSTMNLWTDENASVMDAFMNSDLSSYWAPSAASSHSLHHPPPPQSSASTSTPPPDPPKSLPVFNQETL
QQRLQALIDGARESWTYAIFWQSSYDYSGASVLGWGDGYYKGEEDKGKGKAKMVSSAAEQAHRKKVLRELNSLI
SGSAAGPDDAVDEEVTDTEWFFLVSMTQSFDNGVWLPSQAFYNSTPIWVSGADRLSASACERARQGRVFGLQT
MVCIPSPNGVVEMGSTELIHRTSDLMNKVKILFNFNNLETSSWISGTTAADEGENDPSSMWISEPSSTIEMKDSITTT
VPSGNVPAKPIHSENPSSSSLTENISAIQQPSHQKQSQSFLNFSDYGFESNPSKNTTAAATTTTATPSFKPESGGML
NFGNGNLFSSHSQYVTNEQNEKKRSPASRSSNDEGILSFTSGVILPSSGKVKSGDSDHSDLEASVIREVDSCTKSLE
PEKRPRKRGRKPANGREEPLNHVEAERQRREKLNQKFYALRAVVPNVSKMDKASLLGDAVSYINELKSKLQIAETE
KTEMGKHLELLKKEMGGKDFGNYPNPNDEDLKIGKRKVMDMEIEVKIMGWDAMIRIQSSKKNHPAARLMAAFKD
LDLEMLHASVSVVNDLMIQQATVKMGSRFYTQEQLKMALVARVGGGGGSSHGMM

FIG. 6I

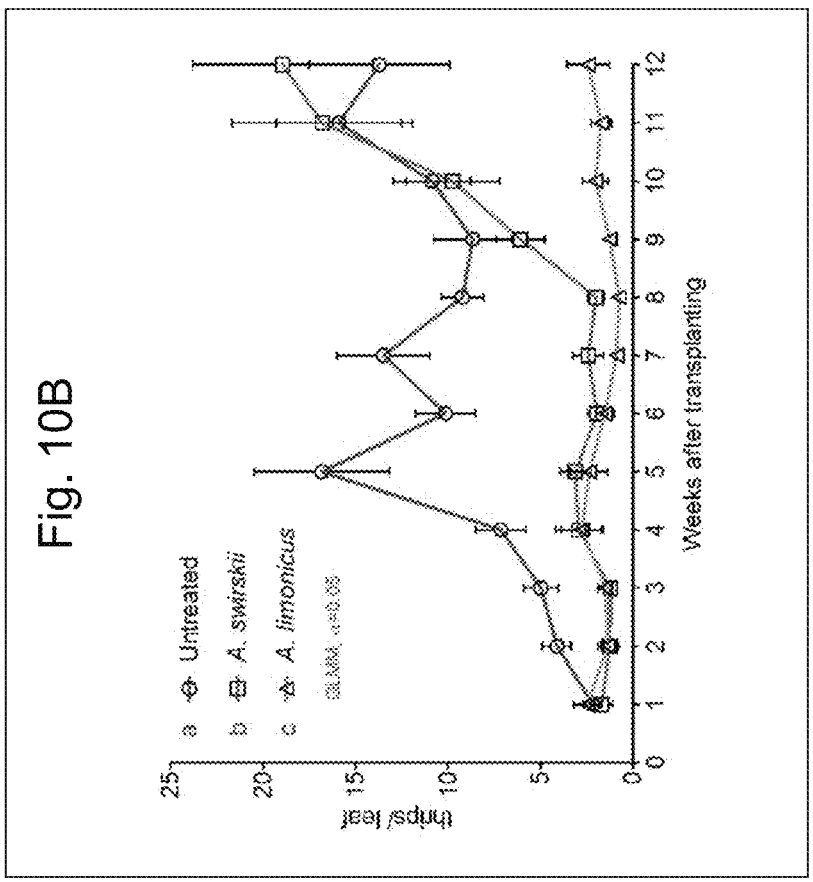
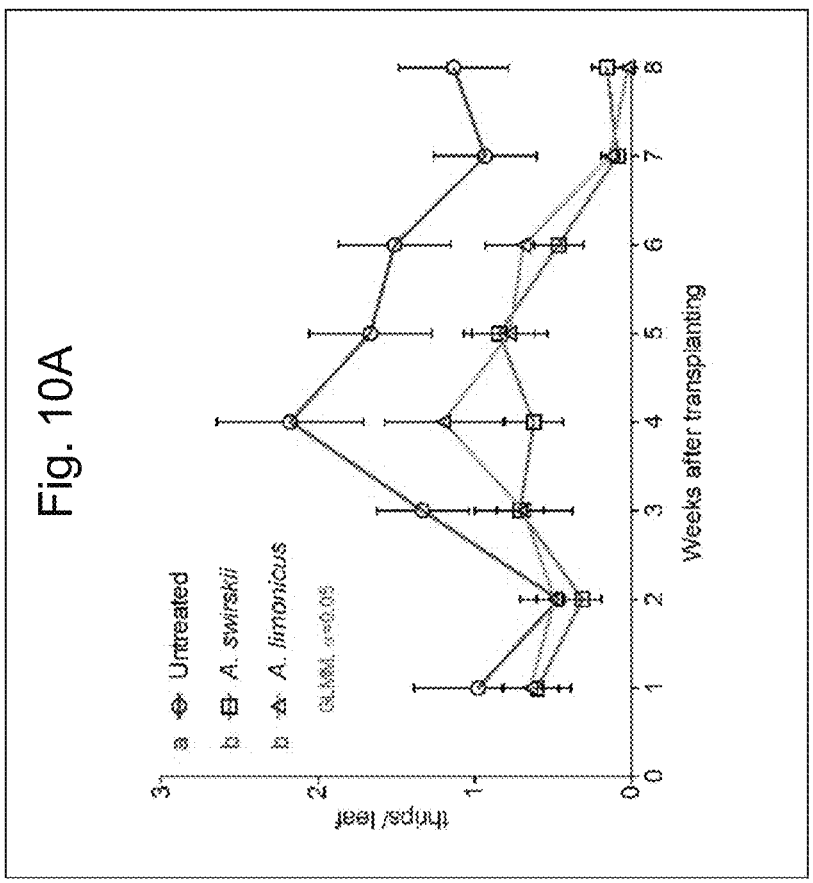

TOMATO PLANTS ALLOWING THE ESTABLISHMENT OF MITES

RELATED APPLICATIONS AND INCORPORATION BY REFERENCE

This application is a continuation-in-part application of international patent application Serial No. PCT/EP2015/068860 filed Aug. 17, 2015, which published as PCT Publication No. WO 2016/026816 on Feb. 25, 2016, which claims benefit of European patent application Serial No. EP 14181306.3 filed Aug. 18, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Jan. 23, 2017, is named 43104_00_2294_SL.txt and is 104,939 bytes in size.

FIELD OF THE INVENTION

The present invention relates to a *Solanum lycopersicum* plant that has an aberrant glandular hair phenotype. The invention also relates to the seeds and progeny of such plants and to propagation material for obtaining such plants. Furthermore, the invention relates to the use of the plants, seeds and propagation material for conferring the aberrant glandular hair phenotype to tomato plants. The invention also relates to sequences and the use of sequences for identifying the aberrant glandular hair phenotype.

BACKGROUND OF THE INVENTION

Plants of the species *Solanum lycopersicum* (tomato) belong to the nightshade family, also known as Solanaceae. Within this family it is nowadays grouped in the genus *Solanum*, which does not only harbor tomato, but also the important food crops potato and eggplant. It is a perennial, herbaceous, flowering plant species which is native to South America.

Other species that are related to tomato within the *Solanum* genus are for example *Solanum pimpinellifolium, Solanum chilense, Solanum peruvianum* and *Solanum habrochaites*. Although it is known that crossing can be considerably difficult, these species are used to obtain traits that are valuable in growing tomato plants. In the recent history, advancement in tomato breeding has led to tomato varieties having, for example higher yield, higher disease resistance and increased shelf life.

Commercial vegetable production, including the production of tomato, is affected by many conditions. The choice of the grower for a certain variety is a determining factor, and forms the genetic basis for the result that can be achieved. In addition, there are many external factors that influence the outcome. Growing conditions like climate, soil, and the use of inputs like fertilizer play a major role. There are various ways of cultivating tomatoes and other crops, among which, the most common are: open field, greenhouse and shade house production. Although the species can be grown under a wide range of climatic conditions, it performs most successfully under dry and warm conditions. In addition to this, the presence of pests and diseases also affects the total yield that can be reached.

Pest and disease management in the production of tomato and other crops can, depending on the way the plants are grown, be done in several ways. On the one hand, breeding focuses on the addition of resistances to pests and diseases to the trait portfolio of plants. Wild relatives of certain species often form a useful source of such resistant germplasm. Alternatively, the growing conditions can be modified in such a way that temperature, humidity levels or light intensity are selected to create less favourable settings for the development of diseases and pests. Often the temperatures that are favourable for the successful production of plants and/or fruits, are also favourable for important pest such as whiteflies. Thirdly, herbicides or pesticides can be used to eradicate weeds and pests, respectively. However, the use of such chemical compounds is under discussion as it might leave residues on plants and fruits that could be compromising to the health of consumers when said plants and/or fruits are consumed.

When vegetables are grown in greenhouses, a fourth pest management alternative is available to growers, which is known as biological pest control. By releasing living organisms that exert their predacious, parasitical and/or herbivorous capacity together with an active human management role, natural enemies can be used to control certain pests. There are various insects known in the art that are commercially reared for use in greenhouses. One of the important insect families in this respect is formed by the Phytoseiidae that is widely used in the biological control of whiteflies, spider mites and thrips.

In addition, WO06/057552 describes a method for biological pest control by making use of the phytoseiid predatory mite *Amblyseius swirskii*. However, these mites are not able to establish themselves on tomato plants, meaning that they are not able to live and reproduce. This makes them unsuitable for use as an efficient biological pest control. Tomato growers can be blocked by the absence of such biological pest controls, because good resistances aimed at insects especially for whitefly, are not yet present in tomato varieties. If a greenhouse is infested by whiteflies, a complete batch of plants might become useless for high yield and high quality vegetable production as the plants might be severely affected. The same applies to the phytoseiid predatory mite *Amblydromalus limonicus*, that is also not capable to establish on tomato plants.

For the predatory mite *Phytoseiulus persimilis*, it is known that it can be used to combat *Tetranychus urticae* (red spider mite) on tomato plants, but this predator exclusively feeds on *Tetranychus* species and thus cannot be deployed to combat infestations of other species. For another predatory mite, *Neoseiulus californicus*, a very low performance on tomato plants has been shown in the control of a *Tetranychus* species infestation.

Citation or identification of any document in this application is not an admission that such document is available as prior art to the present invention.

SUMMARY OF THE INVENTION

Thus, there exists a need for tomato plants that allow for application of biological pest control by the proper establishment of mites, in particular the predatory mites *Amblyseius swirskii* and/or *Amblydromalus limonicus*. Upon successful establishment, the mites can perform their desired role: function as a biological pest control in fighting infestation by whitefly as well as thrips.

In the research that led to the present invention, novel tomato plants were developed, which may comprise a modified Slmyc2 gene that is capable of conferring an aberrant glandular hair phenotype, allowing for the establishment of mites, in particular the predatory mites *Amblyseius swirskii* and/or *Amblydromalus limonicus*. More in detail, it was determined that the predatory mites are hampered by the presence and/or appearance of a specific type of trichomes or glandular hairs that are present on the stems and leaves of tomato plants and/or by volatiles that are produced in the glandular hair cells.

The present invention relates to a modified Slmyc2 gene, which may comprise at least one modification as compared to the wild type sequence of SEQ ID No. 5, which modification leads to the reduction or absence of SlMYC2 protein activity, wherein the modified Slmyc2 gene is capable of conferring an aberrant glandular hair phenotype to a *Solanum lycopersicum* plant. The modification may be suitably selected from a modification that decreases the mRNA level of the Slmyc2 gene, a modification that decreases the level of the SlMYC2 protein and/or a modification that decreases the activity of the SlMYC2 protein, as compared to the wild type Slmyc2 gene of SEQ ID No. 5.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Representative seeds of *Solanum lycopersicum* with the modified Slmyc2 gene of the invention, capable of conferring an aberrant glandular hair phenotype, that allows for the establishment of mites, in particular the predatory mites *Amblyseius swirskii* and/or *Amblydromalus limonicus*, were deposited under accession number NCIMB 42222 on Feb. 24, 2014 with NCIMB Ltd. (Ferguson Building, Craibstone Estate, Bucksburn, Aberdeen, AB21 9YA). All seeds of the deposit comprise the modified Slmyc2 gene homozygously. Plants grown from these seeds thus allow the establishment of mites, in particular the predatory mites *Amblyseius swirskii* and/or *Amblydromalus limonicus*.

The deposited seeds do not meet the DUS criteria which are required for obtaining plant variety protection, and can therefore not be considered to be a plant variety.

The Deposits with NCIMB Ltd. (Ferguson Building, Craibstone Estate, Bucksburn, Aberdeen, AB21 9YA), under deposit accession number NCIMB 42222 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIGS. 1A-C: Sequences of the modified Slmyc2 gene of the invention. SEQ ID No. 1 depicts the genomic DNA sequence. In SEQ ID No. 1, the first base pair (bp) of the start codon is located at position 2648. The last bp of the stop codon is located at position 4540 of SEQ ID No. 1. SEQ ID No. 2 reflects the coding sequence (CDS). SEQ ID No. 3 depicts the protein sequence. SEQ ID No. 4 depicts the mutant sequence of the in-gene marker SL06992.

FIGS. 2A-C: Sequences of the wild type Slmyc2 gene. SEQ ID No. 5 depicts the genomic DNA sequence. In SEQ ID No. 5, the first base pair (bp) of the start codon is located at position 2648. The last bp of the stop codon is located at position 4540 of SEQ ID No. 5. SEQ ID No. 6 reflects the coding sequence (CDS). SEQ ID No. 7 depicts the protein sequence. SEQ ID No. 8 depicts the wild type sequence of the in-gene marker SL06992.

FIG. 4A: Table showing the level of selected volatiles in arbitrary units (A.U.) for plants comprising the mutation homozygously (Mo14/001-006), plants comprising the mutation heterozygously (Mo14/007-012) and for wild type plants (Mo14/013-018).

Aldehyde: cis-3-hexenal

Monos: α-pinene, mycrene, carene, α- and β-phellandrene, p-cymene, limonene. Sesquiterpenes: δ-elemene, β-caryophyllene, α-humulene. Monoterpenoid: verbenene †: corrected for limonene ‡: also known as α-caryophyllene FIG. 4B: Table showing the average levels of selected volatiles as measured in arbitrary units (A.U.) for plants comprising the mutation heterozygously (Mo14/007-012) and for wild type plants (Mo14/013-018)); the P-values were calculated with a Student's t-test and indicate whether the difference between the heterozygous and wild type plants is significant (P<0.05).

Figure 5A:
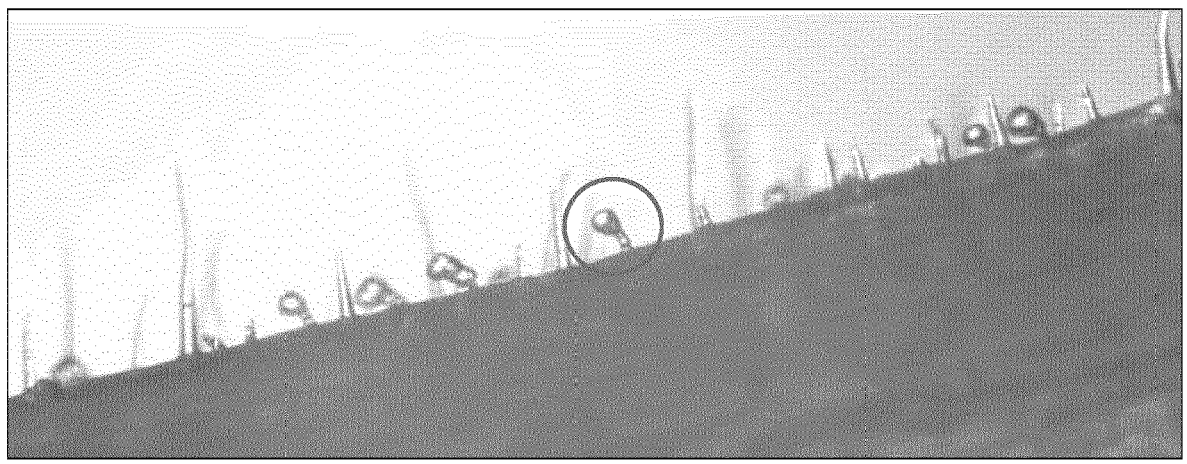
Figure 5B:
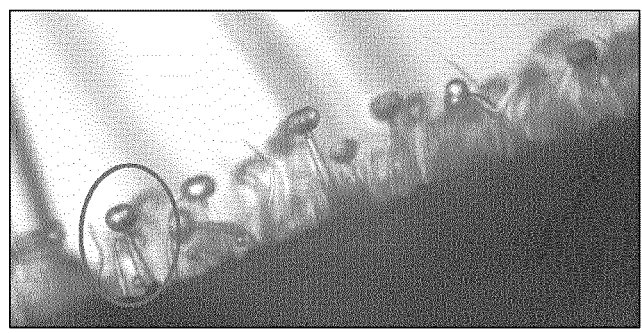

FIGS. 5A-B: Pictures of glandular hair phenotypes. In FIG. 5A, a type VI trichome as found on tomato plants of the invention, is indicated with the circle. In FIG. 5B, a type VI trichome as found on non-mutant background tomato plants, is indicated with the circle.

FIGS. 6A-I: MYC2 amino acid sequences of other plant species. SEQ ID No. 9 to 11 respectively depict the genomic DNA sequence, the coding DNA sequence and the amino acid sequence of *Capsicum annuum*. In SEQ ID No. 9, the first basepair (bp) of the start codon is located at position 2387. The last bp of the stop codon is located at position 4459 of SEQ ID No. 9. SEQ ID No. 12 to 14 respectively depict the genomic DNA sequence, the coding DNA sequence and the amino acid sequence of *Cucumis sativus*. In SEQ ID No. 12, the first basepair (bp) of the start codon is located at position 1578. The last bp of the stop codon is located at position 3563 of SEQ ID No. 12. SEQ ID No. 15 to 17 respectively depict the genomic DNA sequence, the coding DNA sequence and the amino acid sequence of *Cucumis melo*. In SEQ ID No. 15, the first basepair (bp) of the start codon is located at position 2515. The last bp of the stop codon is located at position 4503 of SEQ ID No. 15. SEQ ID No. 18 to 20 respectively depict the genomic DNA sequence, the coding DNA sequence and the amino acid sequence of *Citrillus lanatus*. In SEQ ID No. 18, the first basepair (bp) of the start codon is located at position 2408. The last by of the stop codon is located at position 4378 of SEQ ID No. 18

Figure 7:
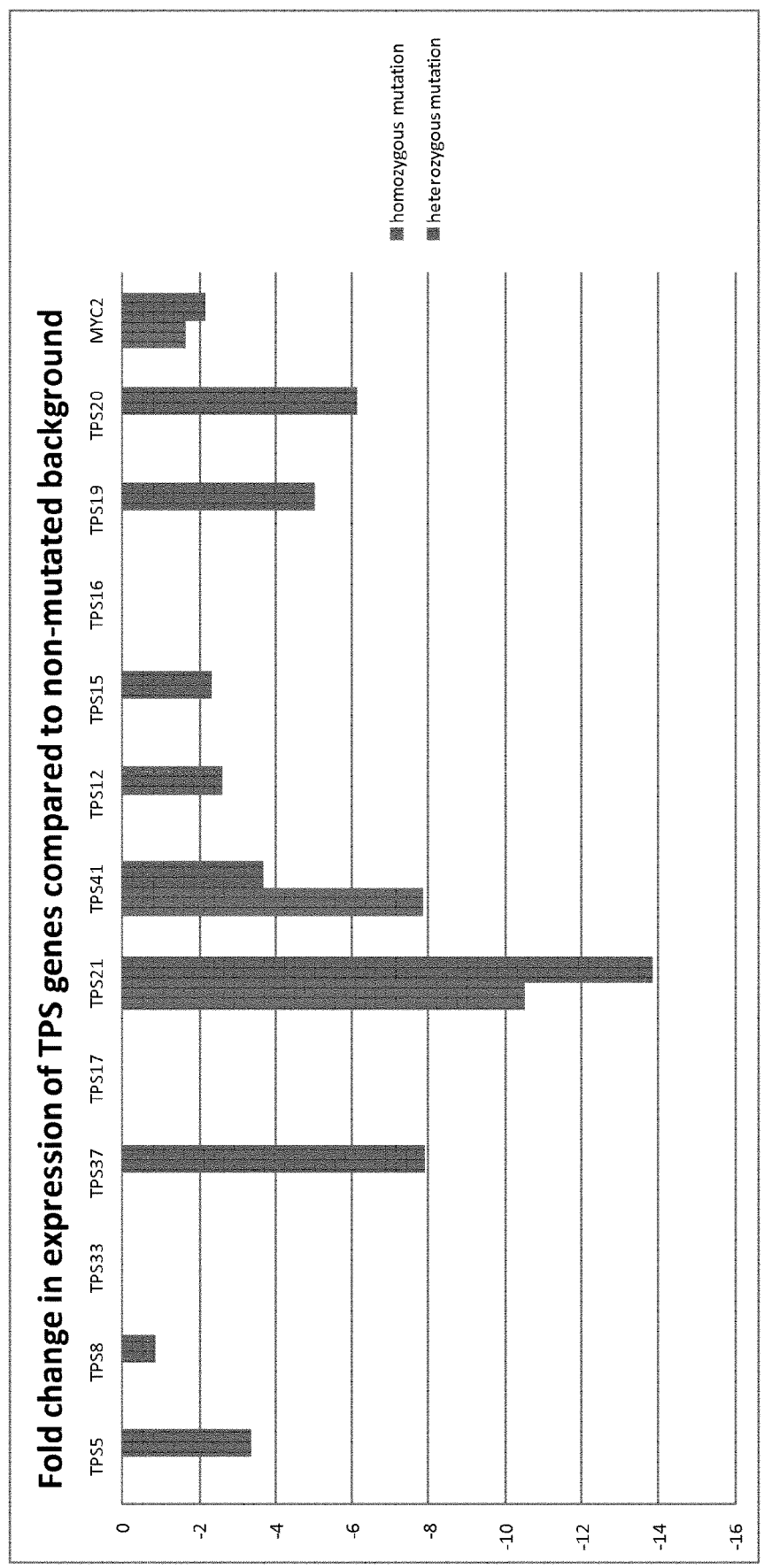

FIG. 7: Expression of terpene synthase genes in the homo- and heterozygous plants of the invention and the non-mutant background plants.

Figure 8:
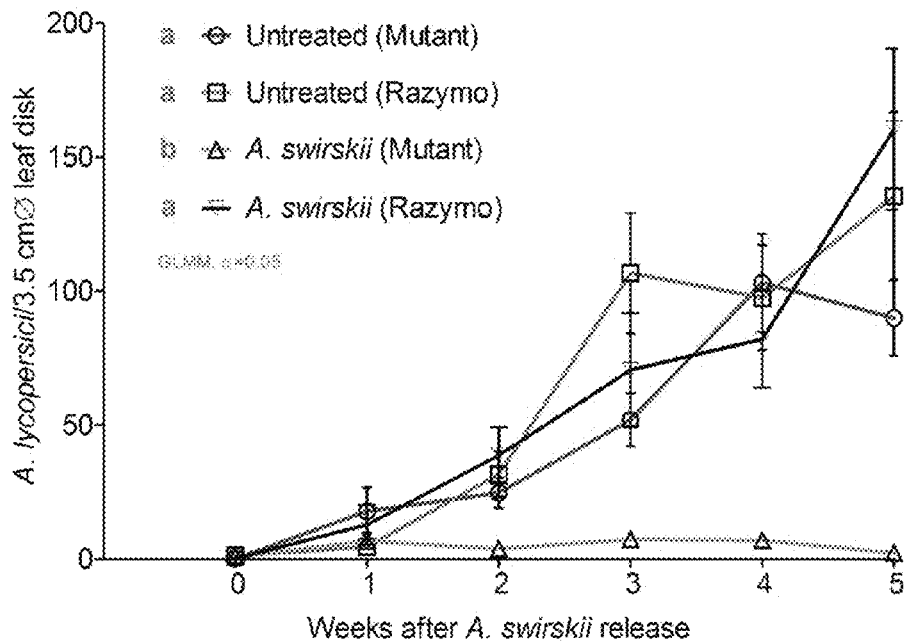

FIG. 8: Average density (number±SE) of *Aculops lycopersici* per 3.5 cm Ø leaflet per week on plants comprising the modified Slmyc2 gene (Mutant) and Razymo, respectively. Evaluations started just before the *A. swirskii* release (week 0), which was released four weeks after *A. lycopersici*. Legends with the same letter are not significantly different (GLMM, P>0.05)

Figure 9:
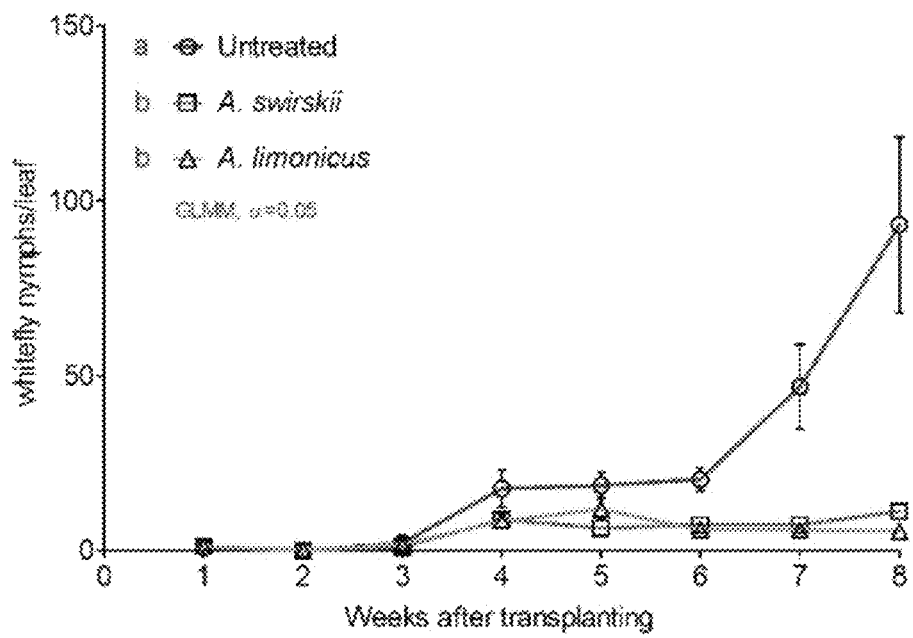

FIG. 9: Average density (number±SE) of *Bemisia tabaci* nymphs per leaf of plants comprising the modified Slmyc2 gene during the experiment. Legends with the same letter are not significantly different (GLMM, P>0.05)

FIG. 10A: Average density (number±SE) of *Frankliniella occidentalis* per leaf of plants comprising the modified Slmyc2 during the summer experiment. Legends with the same letter are not significantly different (GLMM, P>0.05).

FIG. 10B: Average density (number±SE) of *Frankliniella occidentalis* per leaf of plants comprising the modified Slmyc2 during the winter experiment. Legends with the same letter are not significantly different (GLMM, P>0.05).

DETAILED DESCRIPTION OF THE INVENTION

The surface of the various plant parts of tomato and other crops is covered with trichomes, both non-glandular and glandular. Non-glandular trichomes are usually regarded as 'hairs' and do not produce, store, or secrete specific biochemical compounds.

A glandular trichome typically consists of a stalk, made up of one or more cells, and one or more glandular cells at the tip of the stalk that form the glandular head. Four different types of glandular trichomes are identified in tomato and related *Solanum* species, namely types I, IV, VI, and VII. These types differ in size and length of the stalks, and in number of secretory cells that form the glandular head. A variety of biochemical compounds in tomato are produced in glandular trichomes. (McDowell et al., Plant Physiology Vol. 155, 524-539 (2011)).

Biochemical compounds that are produced by the various glandular trichomes in tomato may comprise terpenes, terpenoids, flavonoids, fatty acids, alkaloids, and acyl sugars such as acyl glucoses and acyl sucroses. These compounds are known to play important roles in attracting and repelling various insects and in determining susceptibility to certain diseases. However, many aspects of the roles of these metabolites are still unclear, and extensive research is ongoing to determine more precisely the functionality of glandular trichomes and the substances they excrete.

The invention thus relates to a modified Slmyc2 gene, which may comprise at least one modification as compared to the wild type genomic sequence of SEQ ID No. 5, which modification leads to reduction or absence of Slmyc2 protein activity, wherein the modified Slmyc2 gene is capable of conferring an aberrant glandular hair phenotype to a *Solanum lycopersicum* plant.

The modified slmyc2 gene is also referred to herein as "the gene of the invention", or "the modified slmyc2 gene of the invention". These terms are used interchangeably herein.

In an embodiment, the modification leading to the modified Slmyc2 gene, is selected from a modification that decreases the mRNA level of the Slmyc2 gene; a modification that decreases the level of the Slmyc2 protein; and/or a modification that decreases the activity of the Slmyc2 protein, as compared to the wild type Slmyc2 gene.

In a further embodiment, the modification leading to the modified Slmyc2 gene, results in the presence of a premature stop codon within the coding sequence.

In a preferred embodiment, the modification leading to the modified Slmyc2 gene, results in the presence of a premature stop codon within the coding sequence, in particular the modification which may comprise a single nucleotide polymorphism (SNP) on position 1477 of SEQ ID No. 2, being the coding sequence (CDS). The CDS is that portion of a gene, composed of exons, that codes for protein. SEQ ID No.2 may comprise the presence of a SNP from nucleotide G (wild type) to T. This SNP is the same as the SNP on position 4124 of SEQ ID No. 1, which is the corresponding genomic sequence. This SNP results in a stop codon at amino acid position 493 of SEQ ID No. 3, whereas the wild type amino acid sequence (SEQ ID No. 7) may comprise a Glycine residue at this position. This SNP, resulting in a modified Slmyc2 gene can be found in plants grown from seed of which a representative sample was deposited with the NCIMB under accession number NCIMB 42222.

In another embodiment, the modified Slmyc2 gene of the invention relates to any SNP occurring in SEQ ID No. 6, which is the wild type CDS, that results in the presence of a premature stop codon within that coding sequence. Such a SNP is referred to as a nonsense mutation. Any such a SNP will thus result in a premature stop codon in SEQ ID No. 6. Preferably, the modified Slmyc2 gene of the invention relates to any SNP occurring before position 1477 of SEQ ID No. 6 that results in the presence of a premature stop codon within that coding sequence. Any such SNP will thus result in a premature stop codon before amino acid position 493 of SEQ ID No. 7.

A SNP might also be a mutation in the coding sequence that codes for a different amino acid, instead of a stop codon. Such a SNP is referred to as a missense mutation. The invention also relates to missense mutations resulting in a modified Slmyc2 gene of in the invention.

Modifications in the coding sequence other than SNP's that might result in the modified Slmyc2 gene of the invention include insertions and/or deletions. Insertion of one or more nucleotides might affect proper mRNA splicing or result in a shift in the reading frame. These events can result in a decreased level of SlMYC2 protein and/or in a decreased level of SlMYC2 protein activity. Deletion of one or more nucleotides might, like insertions, result in a shift in the reading frame. This event can result in a decreased level of SlMYC2 protein and/or in a decreased level of SlMYC2 protein activity.

The invention also relates to modifications in the non-coding genomic sequence of Slmyc2, represented by SEQ ID No. 5. Modifications in the non-coding sequence include mutations in the intron sequence, the upstream and/or downstream sequence. The upstream sequence, the sequence before the start codon of the gene of the invention, may comprise the promoter and the 5'-untranslated region (5'-UTR), also called the leader sequence. Since these regions are involved in the regulation of the gene transcription to mRNA and the subsequent translation, and therefore in gene expression, suitable modification can lead to a decrease of the expression through a decrease of the Slmyc2 mRNA level and/or a decrease in the level of the SlMYC2 protein.

The aberrant glandular hair phenotype caused by the gene of the invention was intensively studied. It was determined that the aberrant glandular hair phenotype is particularly observed for type VI trichomes, but might also extend to other types of glandular hairs. Remarkably, the aberrant glandular hair phenotype for type VI glandular hairs on plants of the invention is characterized by the reduction and preferably absence of both mono- and sesquiterpenes, in particular α-pinene, myrcene, carene, α-phellandrene, β-phellandrene, p-cymene, limonene, δ-elemene, β-caryophyllene and/or α-humulene, and/or is characterized by deformed glandular hairs. The aberrant glandular hair phenotype of the invention is further characterized by the reduction and preferable absence of monoterpenoid compounds, in particular verbenene. Other volatiles, such as an aldehyde, were found to be present in aberrant type VI glandular hairs on plants of the invention as well as in the non-mutant background plants (see Example 5).

Of type VI glandular hairs found on plants of the invention, both the stalk cell as well as the head consisting of four glandular cells appear shrunken, less developed and/or dried when compared to the same cells of non-mutated type VI glandular hairs. These deformed type VI glandular hairs also appear to be smaller than non-mutated type VI glandular hairs. This reduction in size might be the direct result from the shrunken, less-developed and/or dried character (see FIGS. 5A-B).

The aberrant glandular hair phenotype does not attract the predatory mites, but it enables and facilitates the mites to roam freely on the plants. 'Predatory mites' or 'mites' as referred to herein, belong to the Phytoseiidae family. The invention relates to this complete family, which may comprise the species *Amblyseius swirskii*, *Amblydromalus limonicus*, *Phytoseiulus persimilis* and *Neoseiulus californicus*.

Thus, the invention relates to a modified Slmyc2 gene, which may comprise at least one modification as compared to the wild type genomic sequence of SEQ ID No. 5, which modification leads to reduction or absence of Slmyc2 protein activity, wherein the modified Slmyc2 gene is capable of conferring an aberrant glandular hair phenotype to a *Solanum lycopersicum* plant, wherein the aberrant glandular hair phenotype is further characterized by the reduction and preferably absence of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs. The aberrant glandular hair phenotype, or the trait of the invention, allows for the establishment of predatory mites, in particular *Amblyseius swirskii* and/or *Amblydromalus limonicus*, on a *Solanum lycopersicum* plant. The aberrant glandular hair phenotype, or the aberrant glandular hair phenotype which allows for the establishment of predatory mites, in particular *Amblyseius swirskii* and/or *Amblydromalus limonicus*, is also referred to herein as "the trait" or "the trait of the invention". These terms are used interchangeably herein.

The said aberrant glandular hair phenotype of the invention is conferred by a modified Slmyc2 gene, the inheritance of which is consistent with that of a monogenic trait. Preferably, said inheritance is consistent with that of a monogenic intermediate trait. In this context, the term "intermediate" is to mean that the aberrant glandular hair phenotype is observable in plants which may comprise the modified Slmyc2 gene in homozygous as well as in heterozygous state.

An example of the modified Slmyc2 gene can be found in plants grown from seed of which a representative sample was deposited with the NCIMB under accession number NCIMB 42222.

In an embodiment, the invention relates to a *Solanum lycopersicum* plant which may comprise the modified Slmyc2 gene of the invention.

The invention relates to a *Solanum lycopersicum* plant that may comprise a modified Slmyc2 gene, wherein said modified Slmyc2 gene results in an aberrant glandular hair phenotype that allows for the establishment of predatory mites, in particular *Amblyseius swirskii* and/or *Amblydromalus limonicus*, on said tomato plant. This plant is also referred to herein as a plant of the invention.

In a preferred embodiment, a plant of the invention may comprise the modified Slmyc2 gene in homozygous state. When a plant comprises the modified Slmyc2 gene in homozygous state, the trait of the invention is characterized by the reduction and preferably absence of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs.

In an embodiment, a plant of the invention may comprise the modified Slmyc2 gene in heterozygous state. When a plant comprises the modified Slmyc2 gene in heterozygous state, the trait of the invention is characterized by the reduction of terpenes, in particular α-pinene, myrcene, carene, α-phellandrene, β-phellandrene, p-cymene, limonene and/or δ-elemene, and/or is characterized by deformed glandular hairs. In this context, the term "reduction of terpenes" is to mean that the level of terpenes is reduced but not completely absent when compared to plants which may comprise the wild type Slmyc2 gene homozygously. The level of terpenes is, in increasing order of preference, 10%, 20%, 30%, 40%, 50%, 60%, 70%, 80%, 90% reduced when compared with the level of terpenes in a plant which may comprise the wild type Slmyc2 gene homozygously.

The present invention also relates to a *Solanum lycopersicum* plant, wherein the modified Slmyc2 gene of the invention is the same as or equivalent to the modified Slmyc2 gene that is found in or obtainable from the genome of *Solanum lycopersicum* plants grown from seeds of which a representative sample was deposited with the NCIMB under accession number NCIMB 42222. With the same or equivalent, it is meant that no segregation for the trait of the invention is observed in the F2 resulting from a cross that is part of an allelism test as described herein. With the same or equivalent, reference is also made to a myc2 gene that is obtained from a wild relative of *Solanum lycopersicum* and modified to confer the same aberrant glandular hair phenotype. In this respect, wild relatives of of *Solanum lycopersicum* include: *S. arcanum, S. chmielewskii, S. neorickii, S. cheesmaniae, S. galapagense, S. pimpinellifolium, S. chilense, S. corneliomulleri, S. habrochaites, S. huaylasense, S. sisymbriifolium, S. peruvianum*, and *S. pennellii*.

The invention further relates to a *Solanum lycopersicum* plant which may comprise the modified Slmyc2 gene homozygously or heterozygously, and which is causative of an aberrant glandular hair phenotype, that allows for the establishment of mites, in particular the predatory mites *Amblyseius swirskii* and/or *Amblydromalus limonicus* on said tomato plant, when compared to a *Solanum lycopersicum* plant not carrying said modified Slmyc2 gene.

In one embodiment, the invention provides a *Solanum lycopersicum* plant exhibiting the trait of the invention, conferred by a modified Slmyc2 gene, which *Solanum lycopersicum* plant is obtainable by crossing a *Solanum lycopersicum* plant which may comprise said modified Slmyc2 gene of which a representative sample of seed was deposited under NCIMB accession number NCIMB 42222 with another *Solanum lycopersicum* plant to produce an F1, subsequently selfing said F1 to obtain an F2, and selecting a *Solanum lycopersicum* plant of the invention.

Furthermore, it was found during the research leading to the present invention that the modified Slmyc2 gene of the invention is located on chromosome 8 of *Solanum lycopersicum*.

More in particular, in the deposit NCIMB 42222 the modified Slmyc2 gene of the invention, the genomic sequence of which is represented by SEQ ID No. 1, is located on chromosome 8 of *Solanum lycopersicum*.

The invention also relates to a *Solanum lycopersicum* plant, which may comprise the modified Slmyc2 gene of the invention, wherein said modified Slmyc2 gene is obtainable by introgression from a *Solanum lycopersicum* plant grown from seeds of which a representative sample was deposited under NCIMB accession number NCIMB 42222, and wherein said modified Slmyc2 gene, the genomic sequence of which is represented by SEQ ID No. 1, in the seeds of the seed deposit number NCIMB 42222 is positioned on chromosome 8 of *Solanum lycopersicum*.

A *Solanum lycopersicum* plant of the invention can be suitably identified amongst descendants from a cross between a *Solanum lycopersicum* plant not allowing the establishment of predatory mites, in particular *Amblyseius swirskii* and/or *Amblydromalus limonicus*, and a plant that carries the modified Slmyc2 gene, preferably in the homozygous state, by growing F2 plants from seeds that are the result of the initial cross and a selfing step, and selecting plants expressing the aberrant glandular hair phenotype. Plants can be selected on the basis of determining the phenotype through a bioassay as described in Example 2, or through the identification of the modified Slmyc2 gene, for example by comparison with SEQ ID No. 5 or SEQ ID No. 6 or using markers that are disclosed herein.

In order to determine equivalence of genetic determinants that cause a particular phenotypic trait the well-known allelism test, more specifically designated as complementation test, can be used. To determine whether a plant shows the same aberrant glandular hair phenotype as plants of the invention, an allelism test can be performed in which a tester plant which is homozygous for the modified Slmyc2 gene of the invention is crossed with material to be tested that is also homozygous for its genetic determinant. When no segregation for aberrant glandular hair phenotype is present in the F2 of the cross, the genetic determinants have been proven to be equivalent or the same and the plant is thus a plant of the invention.

The tester plant is suitably a plant of deposit NCIMB 42222, or a progeny plant of the deposit showing an aberrant glandular hair phenotype that allows for the establishment of mites, in particular the predatory mites *Amblyseius swirskii* and/or *Amblydromalus limonicus* on said *Solanum lycopersicum* plant.

The *Solanum lycopersicum* plant of the invention can be any one of the types of cultivated tomato from the following group: cherry, plum, cocktail, truss, beefsteak, round, grape, etc.

In another embodiment, the invention relates to a *Solanum lycopersicum* seed which may comprise the modified Slmyc2 gene of the invention.

This seed is also referred to herein as a seed of the invention.

In a further embodiment, the plant grown from seed of the invention allows for the establishment of mites, in particular the predatory mites *Amblyseius swirskii* and/or *Amblydromalus limonicus*, when the modified Slmyc2 gene is present in heterozygous, preferably in the homozygous state.

The invention further relates to a *Solanum lycopersicum* seed which may comprise said modified Slmyc2 gene, which seed is capable of growing into a plant that exhibits the trait of the invention.

The invention also relates to progeny of the *Solanum lycopersicum* plants, cells, tissues, and seeds of the invention, wherein the progeny plants, cells, tissues, and seeds may comprise the modified Slmyc2 gene. Such progeny can in itself be plants, cells, tissues, or seeds.

The term "progeny" as used herein is intended to mean the first and all subsequent descendants from a cross with a plant of the invention that may comprise the said modified Slmyc2 gene. "Progeny" also encompasses plants that carry the modified Slmyc2 gene of the invention in homozygous or heterozygous state and are obtained from other plants or progeny of plants of the invention by vegetative propagation or multiplication.

The invention relates to a progeny plant of a *Solanum lycopersicum* plant which may comprise the modified Slmyc2 gene of the invention in homozygous or heterozygous state.

The invention also relates to a progeny plant of *Solanum lycopersicum* plant of the invention that exhibits the aberrant glandular hair phenotype, allowing for the establishment of mites, in particular the predatory mites *Amblyseius swirskii* and/or *Amblydromalus limonicus*, on said progeny plant. This progeny plant thus may comprise the modified Slmyc2 gene in the heterozygous, preferably homozygous state.

According to a further aspect thereof, the invention relates to propagation material capable of developing into and/or being derived from a *Solanum lycopersicum* plant which may comprise the modified Slmyc2 gene of the invention in homozygous or heterozygous state.

This propagation material is also referred to herein as propagation material of the invention.

In one embodiment, such propagation material is formed by a seed of the *Solanum lycopersicum* plant of the invention, wherein the seed is capable of developing into a plant that may comprise the modified Slmyc2 gene of the invention in homozygous or heterozygous state.

In a further embodiment, the propagation material of the invention is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts and cells.

In an additional embodiment, the invention relates to tissue culture of propagation material of the invention.

In another embodiment, the plant developed out of the propagation material may comprise a modified Slmyc2 gene as found in *Solanum lycopersicum* plants grown from seeds of which representative seed was deposited under NCIMB accession number NCIMB 42222.

The invention also relates to the harvested part of the *Solanum lycopersicum* plant which may comprise the modified Slmyc2 gene of the invention.

Moreover, the invention relates to a food product which may comprise one or more harvested parts of a *Solanum lycopersicum* plant which may comprise the modified Slmyc2 gene of the invention. The harvested part or food product can be, or may comprise the fruits of a *Solanum lycopersicum* plant. A preferred food product which may comprise a fruit—or parts thereof—of the *Solanum lycopersicum* plant of the invention is a salad, wherein the fruit may optionally be mixed with leaves of for example lettuce, spinach, endive, chicory, beet, Swiss chard, etc. The food product or harvested part may have undergone one or more processing steps. Such a processing step might comprise, but is not limited to any one of the following treatments or combinations thereof: cutting, washing, cooking, steaming, baking, frying, pasteurizing, freezing, grinding, extracting oil, pickling, or fermenting. The processed form that is obtained is also part of this invention.

Yet another aspect of the invention relates to the use of the modified Slmyc2 gene of the invention for the development of a *Solanum lycopersicum* plant on which predatory mites, in particular *Amblyseius swirskii* and/or *Amblydromalus limonicus* can establish.

In an embodiment, the invention relates to the use of the modified Slmyc2 gene of the invention for the development of a *Solanum lycopersicum* plant on which predatory mites, in particular *Amblyseius swirskii* and/or *Amblydromalus limonicus* can establish, wherein the establishment of said mites is allowed by an aberrant glandular hair phenotype.

In yet another embodiment, the invention relates to the use of the modified Slmyc2 gene of the invention for the development of a *Solanum lycopersicum* plant, wherein the modified Slmyc2 gene of the invention is capable of conferring an aberrant glandular hair phenotype to said *Solanum lycopersicum* plant, wherein the aberrant glandular hair phenotype is characterized by the absence of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs.

In another embodiment, the invention relates to the use of a plant of the invention in combination with the predatory mite *Amblyseius swirskii* for the control of a plant pest, in particular *Aculops lycopersici, Bemisia tabaci* and/or *Frankliniella occidentalis*.

In another embodiment, the invention relates to the use of a plant of the invention in combination with the predatory mite *Amblydromalus limonicus* for the control of a plant pest, in particular *Aculops lycopersici, Bemisia tabaci* and/or *Frankliniella occidentalis*.

In another embodiment, the invention relates to the use of a plant of the invention in combination with the predatory mites *Amblyseius swirskii* and *Amblyseius swirskii* for the control of a plant pest, in particular *Aculops lycopersici, Bemisia tabaci* and/or *Frankliniella occidentalis*.

In another embodiment, the invention relates to the use of a plant of the invention in combination with the predatory mite *Phytoseiulus persimilis* for the control of a plant pest, in particular *Tetranychus urticae*.

In another embodiment, the invention relates to the use of a plant of the invention in combination with the predatory mite *Neoseiulus californicus* for the control of a plant pest, in particular *Tetranychus urticae*.

In another embodiment, the invention relates to the use of a plant of the invention in combination with the predatory mite *Phytoseiulus persimilis* and *Neoseiulus californicus* for the control of a plant pest, in particular *Tetranychus urticae*.

The trait of the invention may be identified by, for instance, using suitable markers.

The skilled person knows how to develop new markers linked to a trait using already known genes, markers, QTLs, alleles or other DNA molecules that are associated with a certain trait, and sequences thereof.

The term "genetic determinant" as used herein encompasses one or more QTLs, genes, or alleles. These terms are used interchangeably. A genetic determinant can be identified by the position on a genetic map, or by indication of the location on a linkage group or chromosome. When a genetic determinant is no longer linked to a specific molecular marker, but its position on a chromosome as defined on a genetic map is unaltered, this genetic determinant is still the same as when it was linked to the molecular marker. The trait that it confers is therefore also still the same.

The invention further relates to a cell of a *Solanum lycopersicum* plant of the invention, which cell may comprise the modified Slmyc2 gene of the invention. The said cell thus may comprise the genetic information encoding the said aberrant glandular hair phenotype, in particular genetic information which is substantially identical, preferably completely identical to the genetic information encoding the said aberrant glandular hair phenotype, wherein the said genetic information is the modified Slmyc2 gene, which may comprise at least one modification as compared to the wild type sequence of SEQ ID No. 5. Preferably, the cell of the invention is part of a plant or plant part, but the cell may also be in isolated form.

The invention also relates to a cell of a *Solanum lycopersicum* plant, which cell may comprise the modified Slmyc2 gene of the invention, and which plant is obtained or obtainable by transferring the trait of the invention into an agronomically valuable *Solanum lycopersicum* plant. The trait of the invention is caused by the modified Slmyc2 gene of the invention which is as found in seeds of which a representative sample was deposited under NCIMB accession number NCIMB 42222.

The invention further relates to the use of seeds of a *Solanum lycopersicum* plant, which seed may comprise the modified Slmyc2 gene of the invention for transferring the modified Slmyc2 gene into another agronomically valuable *Solanum lycopersicum* plant.

The invention also relates to the use of seeds of which a representative sample was deposited under NCIMB accession number NCIMB 42222 for transferring the modified Slmyc2 gene of the invention into another agronomically valuable *Solanum lycopersicum* plant.

The invention also relates to the use of a *Solanum lycopersicum* plant of the invention for the cultivation and preservation of predatory mites or a colony therefrom, with the aim of controlling an insect pest.

The invention also relates to the use of a *Solanum lycopersicum* plant which may comprise the modified Slmyc2 gene of the invention, as a crop.

The invention also relates to the use of a *Solanum lycopersicum* plant which may comprise the modified Slmyc2 gene of the invention as a source of seed.

The invention also relates to the use of a *Solanum lycopersicum* plant which may comprise the modified Slmyc2 gene of the invention as a source of propagating material.

The invention also relates to the use of a *Solanum lycopersicum* plant which may comprise the modified Slmyc2 gene for consumption.

In plant species other than *Solanum lycopersicum*, the homolog of Slmyc2 might influence the glandular hair phenotype. Therefore, the invention also relates to a modified myc2 gene capable of conferring an aberrant glandular hair phenotype to a plant, which modification leads to reduction or absence of MYC2 protein activity, and wherein the modification may be selected from a modification that decreases the mRNA level of the myc2 gene; a modification that decreases the level of the MYC2 protein; and/or a modification that decreases the activity of the MYC2 protein, as compared to a non-modified wild type myc2 gene.

The invention also relates to a modified myc2 gene that leads to the reduction and/or absence of terpenes in a plant. The modified myc2 gene can be present in heterozygous or homozygous state. The myc2 gene can be modified in the same or equivalent way as the Slmyc2 gene, as described herein.

The aberrant glandular hair phenotype conferred by modified myc2 gene is characterized by the absence and/or reduction of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs. In this respect, absence of terpenes is a level of terpenes that is not detectable by currently available measurement techniques and/or is at least, in increasing order of preference, 95%, 96%, 97%, 98%, 99% or 100% lower than the level of terpenes in a plant which may comprise the wildtype myc2 gene homozygously. The term "reduction of terpenes" is to mean in this context that the level of terpenes is reduced but not completely absent when compared to plants which may comprise the wild type myc2 gene homozygously. The level of terpenes is, in increasing order of preference, 10%, 20%, 30%, 40%, 50%, 60%, 70%, 80%, 90% reduced when compared with the level of terpenes in a plant which may comprise the wild type myc2 gene homozygously.

In an embodiment, a plant of the invention which may comprise the modified myc2 gene exhibits the aberrant glandular hair phenotype of the invention, allowing for the establishment of predatory mites, in particular *Amblyseius swirskii* and/or *Amblydromalus limonicus* on said plant.

In a preferred embodiment, a plant of the invention may comprise the modified myc2 gene in homozygous state. When a plant comprises the modified myc2 gene in homozygous state, the aberrant glandular hair phenotype allowing for the establishment of predatory mites, in particular *Amblyseius swirskii* and/or *Amblydromalus limonicus* on said plant, is characterized by the absence and/or reduction of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs.

In an embodiment, a plant of the invention may comprise the modified myc2 gene in heterozygous state. When a plant comprises the modified myc2 gene in heterozygous state, the aberrant glandular hair phenotype allowing for the establishment of predatory mites, in particular *Amblyseius swirskii* and/or *Amblydromalus limonicus* on said plant, is characterized by the reduction of terpenes, in particular α-pinene, myrcene, carene, α-phellandrene, β-phellandrene, p-cymene, limonene, δ-elemene, β-caryophyllene and/or α-humulene. The term "reduction of terpenes" is defined above.

The invention further relates to the use of such a modified myc2 gene for the development of a plant that may comprise a reduced level of terpenes or a plant showing absence of terpenes.

The invention further relates to the use of such a modified myc2 gene for the development of a plant that exhibits an aberrant glandular hair phenotype, wherein said aberrant glandular phenotype is caused by the reduction or absence of MYC2 protein activity as compared to non-modified wild type MYC2 protein activity.

One way in which the modified myc2 gene can be used is by reducing its expression. The reduced expression can be achieved by a decrease in the mRNA level of the myc2 gene; a decrease in the level of MYC2 protein; and/or a decrease in the activity of the MYC2 protein, as compared to the mRNA level, protein level or protein activity of a non-modified wild type myc2 gene.

The modified myc2 gene of the invention can be used to confer an aberrant glandular phenotype to a plant, wherein the plant is selected from any of the species *Capsicum annuum, Cucumis melo, Cucumis sativus* and *Citrullus lanatus*. Also, the modified myc2 gene can be used for reducing or eliminating terpenes in those plant species. The wild type genomic sequence, the wild type CDS and the wild type amino acid sequence for myc2 of *Capsicum annuum* are depicted with SEQ ID No. 9, 10 and 11 respectively. The wild type genomic sequence, the wild type CDS and the wild type amino acid sequence for myc2 of *Cucumis sativus* are depicted with SEQ ID No. 12, 13 and 14 respectively. The wild type genomic sequence, the wild type CDS and the wild type amino acid sequence for myc2 of *Cucumis melo* are depicted with SEQ ID No. 15, 16 and 17 respectively. The wild type genomic sequence, the wild type CDS and the wild type amino acid sequence for myc2 of *Citrullus lanatus* are depicted with SEQ ID No. 18, 19 and 20 respectively.

Both the Slmyc2 as the myc2 genes can be modified by means of mutagenesis. Mutagenesis may comprise the random introduction of at least one modification by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements.

Mutagenesis also may comprise the more specific, targeted introduction of at least one modification by means of homologous recombination, oligonucleotide-based mutation induction, zinc-finger nucleases (ZFNs), transcription activator-like effector nucleases (TALENs) or Clustered Regularly Interspaced Short Palindromic Repeat (CRISPR) systems.

A modified Slmyc2 or myc2 gene of the invention can alternatively be introduced into a plant using genetic modification. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

In one embodiment the modified Slmyc2 or myc2 gene is an exogenous Slmyc2 or myc2 gene which can be introduced into a plant by a transgenic method or a cisgenic method.

The invention also relates to a modified recombinant Slmyc2 or myc2 gene, wherein the expression of said modified recombinant Slmyc2 or myc2 gene is driven by a strong promoter, which promoter is operably linked to a Slmyc2 or myc2 gene sequence, which gene sequence includes the 5'-UTR, the CDS, and/or the 3'-UTR. Many examples of strong constitutive promoters are known in the art; some of the most commonly used ones are e.g. the cauliflower mosaic virus 35S-promoter (pCaMV 35S) and modified versions thereof, ubiquitin promoters from various plant species, actin promoters from various plant species, and the promoter of Elongation Factor 1 alpha (EkF1α).

In one embodiment the invention relates to a gene construct, which gene construct may comprise a selectable marker, a promoter sequence, a Slmyc2 or myc2 gene sequence, and a terminator sequence.

In one aspect the invention relates to a method for producing a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus*, which may comprise
  a) crossing a plant which may comprise the modified Slmyc2 gene with another plant;
  b) selfing the resulting F1 plants to obtain F2 plants;
  c) selecting plants that exhibit the aberrant glandular hair phenotype and/or may comprise the modified Slmyc2 gene in the F2;
  d) optionally performing one or more additional rounds of selfing or crossing, and subsequently selecting a plant which may comprise the trait or modified gene of the invention.

The word "trait" in the context of this application refers to the phenotype of the plant. In particular, the word "trait" refers to the trait of the invention, more in particular to the aberrant glandular hair phenotype that allows for the establishment of mites, in particular the predatory mites *Amblyseius swirskii* and/or *Amblydromalus limonicus* as a result of the presence of a modified Slmyc2 gene. The term "genetic determinant" is used for the genetic information in the genome of the plant that confers the trait of the invention, the genetic information being the modified Slmyc2 gene. When a plant exhibits the trait of the invention, its genome may comprise the genetic determinant conferring the trait of the invention. The plant thus has the genetic determinant of the invention. According to the invention, the genetic determinant may comprise the modified Slmyc2 gene.

It is clear that the parent plant that provides the trait of the invention is not necessarily a plant grown directly from the deposited seeds. The parent plant can also be a progeny plant from seed that is identified to comprise the trait of the invention by other means.

In one aspect, the invention relates to a method for producing a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus*, which may comprise
  a) crossing a plant which may comprise the modified Slmyc2 gene with another plant;
  b) optionally backcrossing the resulting F1 plants with the preferred parent plant;
  c) selecting for plants that exhibit an aberrant glandular hair phenotype and/or may comprise the modified Slmyc2 gene in the F2;
  d) optionally performing one or more additional rounds of selfing or crossing, and subsequently selecting a plant exhibiting an aberrant glandular hair phenotype as a plant which may comprise the modified Slmyc2 gene.

The invention additionally provides a method of introducing another desired trait into a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus*, which may comprise:
  a) crossing a *Solanum lycopersicum* plant which may comprise a modified Slmyc2 gene, representative seed of which were deposited under deposit number NCIMB 4222, with a second *Solanum lycopersicum* plant that exhibits a desired trait to produce F1 progeny;
  b) selecting an F1 progeny that exhibits said aberrant glandular hair phenotype and/or may comprise the modified Slmyc2 gene and the desired trait;
  c) crossing the selected F1 progeny with either parent plant, to produce backcross progeny;
  d) selecting backcross progeny exhibiting the desired trait and an aberrant glandular hair phenotype and/or which may comprise the modified Slmyc2 gene; and
  e) optionally repeating steps c) and d) one or more times in succession to produce selected fourth or higher backcross progeny that exhibits the desired trait and the aberrant glandular hair phenotype. The invention includes a *Solanum lycopersicum* plant produced by this method.

In one embodiment selection for plants exhibiting the aberrant glandular hair phenotype of the invention is performed in the F1 or any further generation, preferably by using SEQ ID No. 1 or 2. In another aspect selection for the trait of the invention is started in the F2 of a cross or alternatively of a backcross. Selection of plants in the F2 can be performed phenotypically as well as by using the said sequences which directly or indirectly detect the genetic determinant underlying the trait.

In one embodiment selection for plants exhibiting the aberrant glandular hair phenotype is started in the F3 or a later generation.

In one embodiment the plant which may comprise the genetic determinant is a plant of an inbred line, a hybrid, a doubled haploid, or of a segregating population.

The invention further provides a method for the production of a *Solanum lycopersicum* plant which may comprise the modified Slmyc2 gene of the invention by using a doubled haploid generation technique to generate a doubled haploid line which may comprise the modified Slmyc2 gene.

The invention furthermore relates to hybrid seed that can be grown into a *Solanum lycopersicum* plant which may comprise the modified Slmyc2 gene of the invention, and to a method for producing such hybrid seed which may comprise crossing a first parent plant with a second parent plant and harvesting the resultant hybrid seed, wherein said first parent plant and/or said second parent plant is a plant of the invention.

In one embodiment, the invention relates to a method for producing a hybrid *Solanum lycopersicum* plant which may comprise the modified Slmyc2 gene of the invention, which may comprise crossing a first parent *Solanum lycopersicum* plant with a second parent *Solanum lycopersicum* plant and harvesting the resultant hybrid seed, of which the first parent plant and/or the second parent plant may comprise the modified Slmyc2 gene of the invention, and growing said hybrid seeds into hybrid plants.

The invention also relates to a method for the production of a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus* by using a seed that may comprise the modified Slmyc2 gene of the invention for growing the said *Solanum lycopersicum* plant. The seeds are suitably seeds of which a representative sample was deposited with the NCIMB under deposit number NCIMB 42222.

The invention also relates to a method for obtaining a *Solanum lycopersicum* plant which exhibits an aberrant glandular hair phenotype, that allows for the establishment of mites, in particular the predatory mites *Amblyseius swirskii* and/or *Amblydromalus limonicus*, which may comprise reducing the endogenous level of SlMYC2 protein in the plant by mutation of the Slmyc2 gene of the plant.

The invention also relates to a method for seed production which may comprise growing *Solanum lycopersicum* plants from seeds of which a representative sample was deposited with the NCIMB under deposit number NCIMB 42222, allowing the plants to produce seeds, and harvesting those seeds. Production of the seeds is suitably done by crossing or selfing.

In one embodiment, the invention relates to a method for producing a *Solanum lycopersicum* plant which may comprise the modified Slmyc2 gene of the invention by using tissue culture.

The invention furthermore relates to a method for producing of a *Solanum lycopersicum* plant which may comprise the modified Slmyc2 gene of the invention by using vegetative reproduction.

In one embodiment, the invention relates to a method for producing a *Solanum lycopersicum* plant which may comprise the modified Slmyc2 gene of the invention by using a method for genetic modification to introgress said modified Slmyc2 gene into the *Solanum lycopersicum* plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for developing *Solanum lycopersicum* plants which may comprise the modified Slmyc2 gene of the invention, wherein germplasm which may comprise said modified Slmyc2 gene of the invention is used. Representative seed of said plant which may comprise the modified Slmyc2 gene of the invention and being representative for the germplasm was deposited with the NCIMB under deposit number NCIMB 42222.

In a further embodiment the invention relates to a method for producing a *Solanum lycopersicum* plant which may comprise the modified Slmyc2 gene of the invention, wherein progeny or propagation material of a plant which may comprise the modified Slmyc2 gene conferring the trait of the invention is used as a source to introgress the said trait into another *Solanum lycopersicum* plant. Representative seed of a plant which may comprise the modified Slmyc2 gene of the invention was deposited with the NCIMB under deposit number NCIMB 42222.

The invention provides preferably a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus*, which plant is obtainable by any of the methods herein described and/or familiar to the skilled person.

The aberrant glandular hair phenotype conferred by the modified Slmyc2 gene of the invention enables the establishment on the plant of predatory mites that do normally not establish on tomato plants with a non-aberrant glandular hair phenotype and thus allows biological pest control by means of these mites.

The present invention will be elucidated in the following examples. These examples are for illustrative purposes only and are not to be construed as limiting the present invention in any way.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Creation of *Solanum lycopersicum* Plants of the Invention

Seeds of two *Solanum lycopersicum* breeding lines, TR306 and T029, were treated with ems (ethyl methane sulfonate) by submergence of approximately 10.000 seeds into an aerated solution of 0.5% (w/v) ems during 24 hours at room temperature.

The treated seeds were germinated and the resulting plants were grown in a greenhouse to produce M2 seeds.

After maturation, M2 seeds were harvested and bulked in one pool. The resulting pool of M2 seeds was used as starting material to identify individual M2 plants that showed an aberrant glandular hair phenotype.

The efficacy of the genetic modification procedure was assessed by determining the occurrence of bleached plants, which is indicative for chlorophyll loss due to modifications in genes directly or indirectly involved in the formation or accumulation of chlorophyll. The type VI trichome phenotype is depicted in FIGS. 5A-B.

Example 2

Identification of a *Solanum lycopersicum* Plant that Allows for the Establishment the Predatory Mite *Amblyseius swirskii*

Two breeding lines (TR306 and T029), a commercially available hybrid and three mutants resulting from the experiment as described in Example 1 were used in a bioassay to investigate whether the predatory mite *Amblyseius swirskii* is able to establish on these *Solanum lycopersicum* plants. As a positive control, *Capsicum annuum* variety Compas RZ was also included in this experiment.

In Table 1, an overview of the lines and varieties is given. The bioassay took place in a multi-tunnel greenhouse in Spain under Mediterranean growing conditions. This greenhouse was divided into 4 compartments and one of them was divided into 40 walk-in cages of 5×3.5×4 meter (l×w×h), of which five were used during the experiment. Treatments were compared in a complete randomized block design with five replicates of seven plant species: six tomato varieties (5 selected+1 commercial [negative control]) and 1 sweet pepper (positive control).

Each replicate consisted of two potted plants of each line or variety which were isolated using sticky bands on the pot and the overhead thread used to train the plants to avoid movement of predatory mites between adjacent replicates. One replicate of each plant species was allocated in each block (cage). Seeds of these plants were sown at the end of July 2012 and placed as duplicate of each tested line/variety into a total of 6 cages.

*A. swirskii* predatory mites were released onto 6 week old plants, by sprinkling the carrying material that comprised the mites over all plants at a rate of 100 predatory mites/plant. Quantity of mites per gram of carrying material was used to estimate the amount to release.

The predatory mites were initially fed by adding pollen ad libitum and additions started after predator release and continued weekly for three weeks thereafter. Plants were sampled biweekly for 6 weeks, beginning one week after the release of the predatory mites. In each sampling, five plants were randomly selected in each experimental cage and five leaves were sampled from each of these five randomly selected plants. Leaves were selected at random along the plant. On each leaf, immature stages (larvae, protonymphs, and deutonymphs) and adults of phytoseiid mites were counted.

Figure 3:
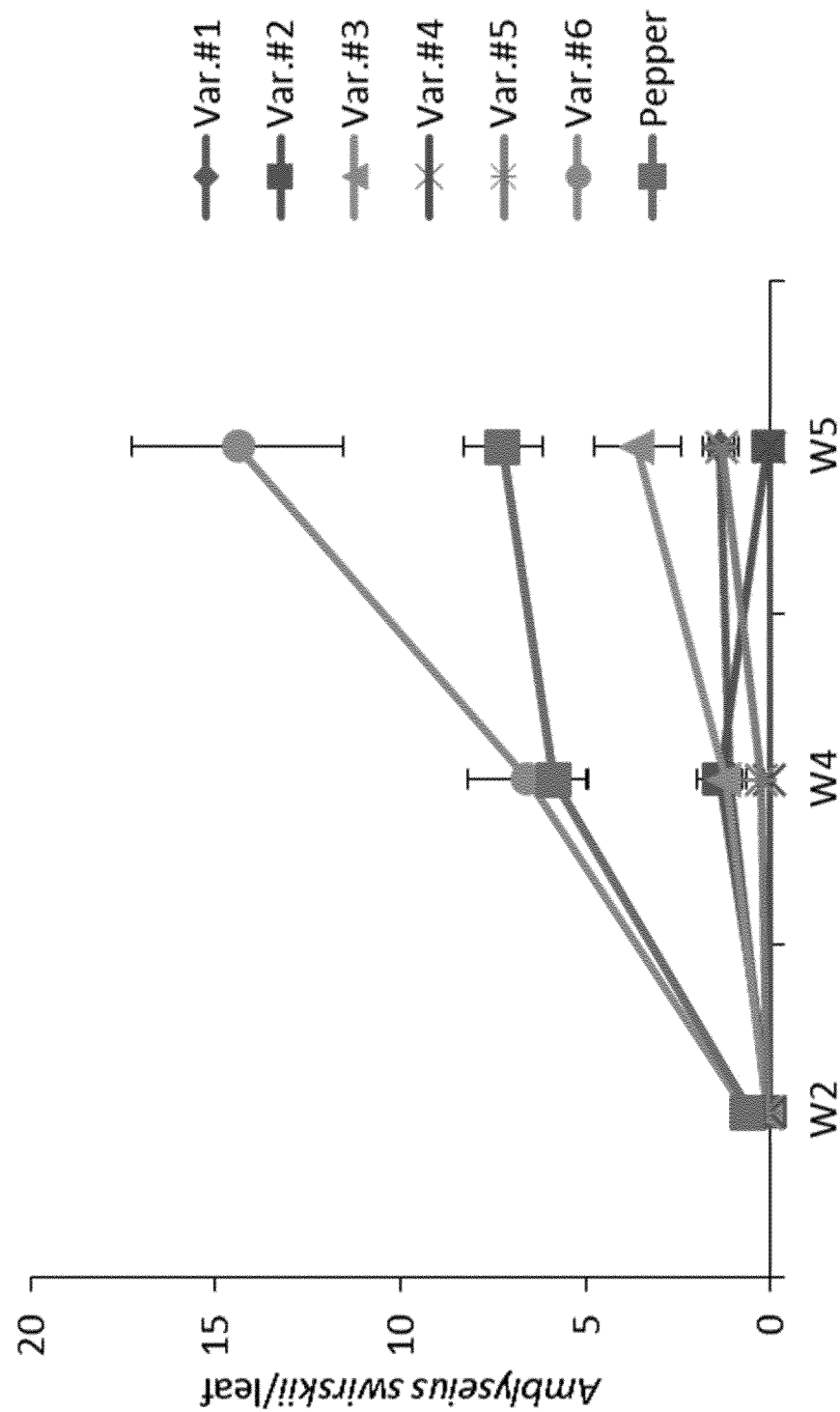
FIG. 3: Average density (number±SE) of *Amblyseius swirskii* per leaf per week for several tomato varieties and for the sweet pepper control.

The results are displayed in FIG. 3. It becomes clear that line #6, comprising the modified Slmyc2 gene of the invention, showed the establishment of the largest number of mites. It is significantly larger than the number found on leaves of the *Capsicum annuum* control plant.

TABLE 1

| Number | Description | Accession |
|---|---|---|
| Line #1 | Hybrid | Mecano |
| Line #2 | Breeding line | TR306 |

TABLE 1-continued

| Number | Description | Accession |
|---|---|---|
| Line #3 | EMS mutant | 302 |
| Line #4 | EMS mutant | 304 |
| Line #5 | Breeding line | T029 |
| Line #6 | EMS mutant | 305 |
| Pepper | Pepper | Compas RZ |

Example 3

QTL Mapping

The *Solanum lycopersicum* mutant comprising the modified Slmyc2 gene of the invention was crossed with parent line TR306. From this cross, a F2 mapping population was generated, which was used for population-specific genetic map construction and QTL-mapping.

In total, 940 markers were used to analyze the 86 offspring individuals. Of these, 241 were polymorphic, informative (enough segregation) and useful (not many U-scores).

The F2 individuals were scored in two classes: hl (having the trait of the invention), wt (wild type phenotype, including unclear phenotypes).

As the trait was being considered (monogenic) recessive, this should result in a 3:1 segregation of the trait. Indeed, the trait distribution in this translation is wt:hl 61:25, which is not significantly different from the expected 3:1 ratio (chi$^2$-test=0.38).

Linkage analysis was performed with MapQTL 6.0. First, interval mapping was performed to identify regions or markers linked to the trait. Second, co-factors were selected after which (as a third step) MQM-mapping was performed.

The coverage of chromosome 8 by polymorphic markers is rather low, as only five markers were identified. As the interval in which the trait is mapped is considerably large (at least 12 cM), analysis of the population with more markers was necessary for fine-mapping of the trait. However, given the fact that many markers appeared to be non-polymorphic on chromosome 8 in this cross, that might need additional initial effort in marker selection.

Example 4

Elucidation of Modified Slmyc2 Gene of the Invention

Besides the QTL that was mapped as described in Example 3, it was investigated whether the gene underlying the trait of the invention could be identified.

Whole genome sequencing (WGS) of the plant of the invention and of the non-mutant background was performed. As in example 3 it was shown that chromosome 8 comprised the modified Slmyc2 gene of the invention, all 25 homozygous SNP markers generated on this chromosome were taken into account. Of these 25 markers, 4 markers were found non-discriminatory, so no difference between the plant of the invention and the non-mutant background was observed.

A total of 227 plants from multiple F4 populations was phenotyped and 80 individuals showed the phenotype of the invention. Remarkably, one out the 21 markers, was 100% predictive for all 80 plants of the invention. For 21 of these plants, marker SL06992 gave an unique positive score. This SNP marker, designated SL06992 (SEQ ID No. 4) was blasted and found to localize on the same place on chromosome 8 as the AUGUSTUS predicted gene SL2_40ch08.g6 was annotated. In this annotation, the nucleotide at position 4124 of the genomic sequence is changed from G to T in plants of the invention. This corresponds with the same position in SEQ ID No. 8, representing the wild type sequence. Said nucleotide change results in a stop codon at position 493 of the amino acid, thereby creating a truncated version of the protein.

Example 5

Determining Terpene Levels in Plants of the Invention

In order to measure terpene levels in plants of the invention, i.e. plants that comprise the modified Slmyc2 gene, already topped *Solanum lycopersicum* plants were used. Samples were taken from the first, second and third leaf from the top of the plant. A total of five leaf discs of 0.71 cm$^2$ were collected. They were stored in a 10 ml vial and 1.0 ml of the solvent dichloromethane was added.

Subsequently, the leaf discs were mildly shaken. After 45-90 minutes, the solvent was transferred in another vial. Solvent extracts were stored at −20° C. until analysis.

In performing the analysis, 200 μl of the solvent comprising volatiles was mixed with 5 μl of the internal standard nonylacetate. Of this mixture, 1 μl was injected in the gas chromatography-mass spectrometry (GC-MS) instrument.

In order to show the ratio of volatile amounts for plants of the invention and heterozygous and wild type plants, the results are shown in arbitrary units. The values given in FIGS. 4A-B are normalized for the internal standard, nonylacetate.

From the results, it becomes clear that both the mono- and sesquiterpenes are absent in the plant of the invention, whereas in plants not comprising the modified Slmyc2 of the invention the presence of terpenes was shown to be significant ($P<0.05$).

Example 6

Determining Expression Levels of Terpene Synthase (TPS) Genes in Plant of the Invention In order to determine whether the absence of certain terpenes is related to expression of TPS genes, a qPCR experiment was designed. The three top leaves of plants of the invention were sampled, pooled and RNA was isolated using the RNeasy kit (Qiagen), using 100 mg of plant tissue. cDNA was synthesized using a Maxima cDNA synthesis kit (Thermo Scientific) starting from a total of 1000 ng RNA. Primer combinations to detect expression of TPS genes in tomato were derived from Falara et al. (Plant. Phys. 157, 770-789 (2011). A qPCR run was executed using the Rotor-Gene Q PCR cycler (Qiagen).

For 12 TPS genes the fold change regulation in plants of the invention containing the mutation homozygously or heterozygously and the non-mutant background was detected, which is shown in FIG. 7. Three types of expression patterns could be identified. For the genes TPS16, TPS17 and TPS33 expression was detected in the wild type plants whereas no expression was detected in both the homozygous as well as the heterozygous plants of the invention, as the fluorescence signal threshold level was not reached. The expression of TPS21 and TPS41 was detected and clearly down regulated in both homozygous as well as heterozygous mutant plants of the invention. For the other TPS genes no expression was detected for the homozygous mutant plants, as the fluorescence signal threshold level was not reached. For the heterozygous plants down regulation was observed when compared to the wild type expression pattern.

Example 7

Evaluation of the Effects of Plants that Comprise the Modified Slmyc2 Gene on the Establishment and Effectiveness of *Amblyseius swirskii* Against *Aculops lycopersici*, The experiment was carried out in a multi-tunnel greenhouse located in Vicar (Almeria, Andalusia, Spain). This experiment was performed in a greenhouse comprising a total of 16 walk-in (experimental) cages of 5×3.5×4 m (l×w×h).

Two factors were evaluated, plant variety and predator, in a split plot design with four replicates. There were four main plots (group of four cages) of both plant varieties (plants comprising the modified Slmyc2 gene and Razymo), each divided into two subplots (experimental cages), each designated at random for each of the following treatments: 0 or 75 *A. swirskii*/plant.

*Amblyseius swirskii* was obtained from Koppert Biological Systems in bottles containing 50,000 mites of different stages and eggs mixed with a prey mite and a carrying material (SWIRSKI-MITE™). *Aculops lycopersici* (tomato russet mite, TRM) to infest the plants was obtained from a rearing colony maintained on tomato for several months before the starting of the experiment and originally collected on tomato plants from different locations within the region of Murcia (Spain)

Seeds of tomato cv. Razymo and plants comprising the modified Slmyc2 gene were sown into peat moss root cubes. When seedlings reached the five-leaves stage, they were transplanted into 25 l coco peat fibre bags placed inside the designated walk-in cage, at 10 seedlings per cage. Each tomato plant was inoculated with ca. 250 mobile stages of TRM two weeks after transplanting. Mites were counted under a stereomicroscope to select pieces of leaflets containing ca. 50 mites and five of these pieces were deposed onto a different leaf of each plant. All mites to infest plants were collected simultaneously and from the same part of the plant to assure homogeneity in age and sex-ratio. Predators were released at once in the designated cages four weeks after the tomato russet mite release. *A. swirskii* was distributed by sprinkling the carrying material over all plants at a rate of 75 predatory mites/plant. Quantity of mites per gram of substrate was used to calculate the amount to release.

Evaluations started just before the predator release and continued weekly thereafter until the end of the experiment. To evaluate the density of TRM, in each sampling, four plants were randomly selected in each walk-in cage and 3 leaf-disks (3.5 cm Ø) were taken from 3 different leaves (one disk per leaf) of each selected plant. One leaf was selected at random from the upper, one from the middle, and one form the bottom third of the plants. Leaf-disc samples were brought to the laboratory into a refrigerated cold-box and then the number of TRM (mobile stages) were counted using a stereoscopic microscope. Predator populations were assessed in situ by counting the number of predatory mites (mobile forms) present in the same above-mentioned leaves, but before picking the leaf-disks to count the number of TRM.

The results from this experiment are visualized in FIG. 8. Numbers of TRM increased progressively over the entire experimental period and averaged at similar numbers in all plots with the exception of those containing the plants comprising the modified Slmyc2 gene and receiving *A. swirskii*, where TRM averaged always at values under 7.5 mites per 3.5 cm Ø leaflet, nearly 20 times lower than in the other treatments at the end of the experiment. Abundance of TRM was therefore lower in response to *A. swirskii* on plants comprising the modified Slmyc2 gene (F3, 45=17.640; P<0.001).

Example 8

Evaluation of the Effectiveness of *Ambleyseius swirskii* and *Amblydromalus limonicus* Against *Bemisia tabaci* (Whitefly) on Plants Comprising the Modified Slmyc2 Gene.

Experiments were carried out in a multi-tunnel greenhouse located in Vicar (Almeria, Andalusia, Spain). This experiment was performed in a greenhouse comprising a total of 16 walk-in (experimental) cages of 5×3.5×4 m (l×w×h).

During the summer and winter experiments, three treatments were compared in a complete randomized block design with 4 replicates in each experiment. The treatments were: 1) *B. tabaci*; 2) *B. tabaci*+*A. swirskii* and 3) *B. tabaci*+*A. limonicus*.

In both experiments, *B. tabaci* adults to infest the plants were collected from a mass-rearing colony maintained on tobacco plants. *A. swirskii* was provided by Koppert Biological Systems in bottles containing 50,000 predatory mites from different stages and eggs mixed with a prey mite and a carrying material (SWIRSKI-MITE™). *A. limonicus* was obtained from Koppert Biological Systems in bottles containing 10,000 mites of different stages and eggs mixed with a prey mite and a carrying material (LIMONICA™).

Seeds of tomato plants comprising the modified Slmyc2 gene were sown into peat moss root cubes. When seedlings reached the five-leaves stage, they were transplanted into 25 l coco peat fibre bags placed inside the designated walk-in cages, at 10 seedlings per cage. Adult pests were cooled briefly in a cold room at 8° C. for counting, then released into all cages at a rate of 10 adults/plant and 5 females/plant per week over three consecutive weeks for a total of 30 whitefly adults/plant. The first whitefly adults were released just after transplanting. This release schedule was used to simulate a gradual but heavy immigration of the pest into the greenhouse. For weekly infestations of all cages, adult whiteflies were simultaneously collected from the mass rearing and belonged to the same cohort to assure homogeneity in age and sex ratio. *A. swirskii* and *A. limonicus* were released one week after the first adult pests release by sprinkling the carrying material over all plants at a rate of 75 predatory mites/plant. Quantity of mites per gram of substrate was used to calculate the amount to release.

In the experiments, in each weekly sampling four plants were randomly selected in each experimental cage and three leaves were sampled from each of the four randomly selected plants. One leaf was selected at random from the upper, one from the middle, and one from the bottom third of the plant. On each leaf, whitefly nymphs and adults and the immature stages (larvae, protonymphs, and deutonymphs) and adults of phytoseiid mites were counted.

The results for the whitefly infestation experiments are shown in FIG. 9. The population of whitefly nymphs was similarly suppressed by *A. swirskii* and *A. limonicus*. Moreover, numbers of whitefly nymphs per leaf remained nearly constant and never exceeded 15 nymphs per leaf during the entire experiment in plots receiving the predators.

Example 9

Evaluation of the Effectiveness of *Ambleyseius swirskii* and *Amblydromalus limonicus* Against *Frankliniella occidenta-*

*lis* (Thrips) Under Summer and Winter Conditions on Plants Comprising the Modified Slmyc2 Gene.

Experiments were carried out in a multi-tunnel greenhouse located in Vicar (Almeria, Andalusia, Spain). This experiment was performed in a greenhouse comprising a total of 16 walk-in (experimental) cages of 5×3.5×4 m (l×w×h).

During the summer and winter experiments, three treatments were compared in a complete randomized block design with 4 replicates in each experiment. The treatments were: 1) *F. occidentalis*; 2) *F. occidentalis*+*A. swirskii* and 3) *F. occidentalis*+*A. limonicus*.

In both experiments, *F. occidentalis* adults to infest the plants were obtained from a rearing colony maintained at Koppert Biological Systems on green bean pods. *A. swirskii* was provided by Koppert Biological Systems in bottles containing 50,000 predatory mites from different stages and eggs mixed with a prey mite and a carrying material (SWIRSKI-MITE™). *A. limonicus* was obtained from Koppert Biological Systems in bottles containing 10,000 mites of different stages and eggs mixed with a prey mite and a carrying material (LIMONICA™).

Procedures were the same for both the Summer and Winter experiments. Seeds of tomato plants comprising the modified Slmyc2 gene were sown into peat moss root cubes (Summer: 1 Jul. 2014; Winter: 22 Sep. 2014). When seedlings reached the five-leaves stage, they were transplanted into 25 l coco peat fibre bags placed inside the designated walk-in cages, at 10 seedlings per cage (Summer: 5 Aug. 2014; Winter: 28 Oct. 2014). Adult pests were cooled briefly in a cold room at 8° C. for counting, then released into all cages at a rate of 10 adults/plant and 5 females/plant per week over three consecutive weeks for a total of 15 thrips females/plant. The first thrips adults were released just after transplanting. This release schedule was used to simulate a gradual but heavy immigration of both pests into the greenhouse. Newly emerged adult thrips were used for the experiment, which were collected prior to each weekly release from a single cohort, to assure the homogeneity in age. Thrips females were mixed with an unknown number of males. *A. swirskii* and *A. limonicus* were released one week after the first adult pests release (Summer: 12 Aug. 2014; Winter: 4 Nov. 2014) by sprinkling the carrying material over all plants at a rate of 75 predatory mites/plant. Quantity of mites per gram of substrate was used to calculate the amount to release.

In the Summer and Winter experiments, in each weekly sampling four plants were randomly selected in each experimental cage and three leaves were sampled from each of the four randomly selected plants. One leaf was selected at random from the upper, one from the middle, and one from the bottom third of the plant. On each leaf, adults and mobile forms of thrips and adults of phytoseiid mites were counted.

The results for the thrips infestation experiments are shown in FIGS. 10A-B. *A. limonicus* and *A. swirskii* were able to significantly reduce thrips populations either during summer or winter, although *A. limonicus* resulted more effective in winter compared to *A. swirskii* (Summer: F2,31=21.632; P<0.001; Winter: F2,45=48.789; P<0.001; FIGS. 10A-B). During summer, in cages receiving the predators numbers of thrips per leaf decreased progressively throughout the experimental period with almost no thrips being recorded at the end (FIG. 10A). During winter, both predators reduced similarly pest populations during the first weeks, but halfway through the experiment (approximately when average daily temperatures were under 20° C.) thrips density increased rapidly in plots treated with *A. swirskii* reaching similar densities than in untreated cages at the end of the experiment, reflecting no control of the pest by the predator (FIG. 10B). It is known that *A. swirskii* is less active at temperatures below 20° C. Contrary, in cages receiving *A. limonicus*, thrips density remained again constant and always averaged under 3, approximately 6 times lower compared to cages receiving *A. swirskii*. *A limonicus* can thus still be successfully used at temperatures at which *A. swirskii* is less active.

The invention is further described by the following numbered paragraphs:

1. Modified Slmyc2 gene, comprising at least one modification as compared to the wild type sequence of SEQ ID No. 5, which modification leads to the reduction or absence of SlMYC2 protein activity, wherein the modified Slmyc2 gene is capable of conferring an aberrant glandular hair phenotype to a *Solanum lycopersicum* plant.

2. Modified Slmyc2 gene of paragraph 1, wherein the modification is selected from a modification that decreases the mRNA level of the Slmyc2 gene, a modification that decreases the level of the SlMYC2 protein and/or a modification that decreases the activity of the SlMYC2 protein, as compared to the wild type Slmyc2 gene of SEQ ID No. 5.

3. Modified Slmyc2 gene of paragraph 1 or 2, wherein the modification results in the presence of a premature stop codon within the coding sequence.

4. Modified Slmyc2 gene of paragraph 3, wherein the modification comprises a SNP on position 1477 of SEQ ID No. 2, in particular from nucleotide G (wild type) to T.

5. Modified Slmyc2 gene of any of the paragraphs 1 to 4, wherein the aberrant glandular hair phenotype is characterized by the reduction and preferably absence of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs.

6. A *Solanum lycopersicum* plant comprising a modified Slmyc2 gene of any of the paragraphs 1 to 5.

7. A *Solanum lycopersicum* plant of paragraph 6, wherein the plant exhibits an aberrant glandular hair phenotype which allows for the establishment of predatory mites, in particular *Amblyseius swirskii* and/or *Amblydromalus limonicus*, on said *Solanum lycopersicum* plant.

8. A *Solanum lycopersicum* seed comprising the modified Slmyc2 gene of any of the paragraphs 1 to 5, wherein the plant that can be grown from the seed shows the aberrant glandular hair phenotype.

9. Progeny plant of a *Solanum lycopersicum* plant of paragraph 6 or 7, wherein the progeny plant comprises the modified Slmyc2 gene, of any of the paragraphs 1 to 5.

10. Propagation material capable of developing into and/or being derived from a *Solanum lycopersicum* plant of paragraph 6 or 7, wherein the propagation material comprises the modified Slmyc2 gene of any of the paragraphs 1 to 5 and wherein the propagation material is selected from a group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts and cells, or a tissue culture thereof.

11. Use of a modified Slmyc2 gene of any of the paragraphs 1 to 5 for the development of a *Solanum lycopersicum* plant on which predatory mites, in particular *Amblyseius swirskii* and/or *Amblydromalus limonicus* can establish.

12. Use of paragraph 11, wherein the establishment of predatory mites, in particular *Amblyseius swirskii* and/or *Amblydromalus limonicus*, is allowed by an aberrant glandular hair phenotype.

13. Use of paragraph 12, wherein the aberrant glandular hair phenotype is characterized by the reduction and preferably absence of terpenes, in particular α-pinene, myrcene, carene, α-phellandrene, 3-phellandrene, p-cymene, limonene, δ-elemene, (3-caryophyllene and/or α-humulene, and/or is characterized by deformed glandular hairs.

14. Use of a *Solanum lycopersicum* plant of paragraph 6 or paragraph 7, for the cultivation and preservation of predatory mites, or a colony therefrom.

15. Method for obtaining a *Solanum lycopersicum* plant which exhibits an aberrant glandular hair phenotype, that allows for the establishment of mites, in particular the predatory mites *Amblyseius swirskii* and/or *Amblydromalus limonicus*, comprising reducing the endogenous level of SlMYC2 protein in the plant by mutation of the Slmyc2 gene of the plant.

16. Modified myc2 gene, which when expressed in a plant leads to the reduction and preferably absence of terpenes in said plant, and/or which is preferably capable of conferring an aberrant glandular hair phenotype to said plant, which gene comprises a modification that leads to reduction or absence of MYC2 protein activity, and wherein the modification is selected from a modification that decreases the mRNA level of the myc2 gene, a modification that decreases the level of the MYC2 protein and/or a modification that decreases the activity of the MYC2 protein, as compared to a non-modified wild type myc2 gene.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A non-naturally occurring *Solanum lycopersicum* plant having homozygously a non-naturally occurring mutated gene comprising a mutation,
   wherein the mutation comprises a G>T mutation at position 1477, with reference to SEQ ID NO: 2,
   wherein the protein expressed from the non-naturally occurring mutated gene terminates prior to amino acid 493, with reference to SEQ ID NO: 7, and
   wherein the mutation confers an aberrant type VI glandular hair phenotype that allows for the establishment of predatory mites on the plant and/or a reduction or absence of terpenes in glandular hair.

2. A non-naturally occurring *Solanum lycopersicum* seed having homozygously a non-naturally occurring mutated gene comprising a mutation,
   wherein the mutation comprises a G>T mutation at position 1477, with reference to SEQ ID NO: 2,
   wherein the protein expressed from the non-naturally occurring mutated gene terminates prior to amino acid 493, with reference to SEQ ID NO: 7, and
   wherein the mutation confers on a plant grown from the seed an aberrant type VI glandular hair phenotype that allows for the establishment of predatory mites on the plant and/or a reduction or absence of terpenes in glandular hair.

* * * * *

UNITED STATES PATENT AND TRADEMARK OFFICE
CERTIFICATE OF CORRECTION

Page 1 of 1

PATENT NO. : 11,091,513 B2
APPLICATION NO. : 15/412241
DATED : August 17, 2021
INVENTOR(S) : Van Herwijnen et al.

It is certified that error appears in the above-identified patent and that said Letters Patent is hereby corrected as shown below:

On the Title Page

Item (73), should read as follows:
(73) Assignee: RIJK ZWAAN ZAADTEELT EN ZAADHANDEL B.V., De Lier (NL)

Signed and Sealed this
First Day of March, 2022

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 20

<210> SEQ ID NO 1
<211> LENGTH: 8000
<212> TYPE: DNA
<213> ORGANISM: Solanum lycopersicum

<400> SEQUENCE: 1
attcaataat taattgtaat tgtctggcat tgttatggtg gttcacatgt caagttgctt      60
ttatattatt tgttattaaa ataaaaatag aaaaatcaat gttattttca cgttcagcat     120
```

```
ccaccaaaac gtgctattaa taatttaatg tctaaaacat atctacaaat tatattatat      180
tagtataata tactttatga tatcttgaac aaagacaatt acaagtagga ccaatcaaaa      240
tgattccaca acgtgacgcc aacgcgtaca aataaggatt ttcctttatt ataactttat      300
aataattaac tcaccgtaat taatttgtat gattataatg aaatgactga aacttttcg       360 ctcttaacaa gaaatctcga tcgaacttta gccatgaaat aaaaataatt gtgttgagag      420 tagaattttcc aaaaatagat tttatagtgt gtaaaattat atttattaat ttttaatatg    480
attatcaaaa taccgaatcg aagaaagtaa gtaaattta aggaatgtaa tatgtatgtg      540
gtctcaccct tacatgcatt gaatatgtaa agagtgtttt cgaaggacaa ggattttttt     600
gttttactta ttaatgtatt ttaaaaactt aagacaaaat tatttactca aaatttacat     660
gcgatattgt actaaaacga tttacaatta ttgtaggtac cttaattact ctgatagtgc     720
atggccttta attcaaggg ataccaataa caaaaaagtc catatttgtg atgaatatgt      780
cttatcacaa aaattgagag gaatattatg atagatttaa tgaaaaattt taatatggac     840
aaaagaatat tatgatagat ttaaagaaaa aatttaatat ggacaaaatt tgtgatggac    900
taataaattt actttttttca ttacgaattt ttggagcctc acgttgaaga tccaatgact   960
tgttttcaaa ttagtttcaa agaatggctg agaatagtct ttctaaaaaa gcatcttcaa    1020
tcgatggctt gaatttaatt attaaaagaa ttattatatt tgataatgta ttgattagat    1080
gcacgttatg aatttaaaat ttcatttag acatgaacct aatatttaaa tagacaccaa     1140
cacaagtata tgacgcgaac aagtgatatt taagttatga gttcaaaatt tatgaatcat    1200
tagtcataac taaaaatgtg atactttagg ggataaggat agaagagcaa atttaaattt    1260
tacgtgaacc ttttttattt aaatagaaaa taatagagcg ataaattcat tatttatcga    1320
gtttcaaatc attaaaaata caatatataa tatacgaatt agatgtatat acacatttga    1380
attcaatggt ggactatata atttgatatt taagtaagca aaagtagata aggagttcaa    1440
gtttaaattt gtaaacatag aatttcctat tttagagttt aaggtaaatt tatgtatatt    1500
ttatcgtttg gaatctcatt ttacgatgct acgctaaata ttagaaattg ctaaaaataa    1560
ttgttgttat tgtaatataa tatcaaaatc aacatgattt catttatttt ctttccatat    1620
atgaattatt tccataaagc ctacatgtag gagatatgct aatttaatat ttcctggaaa    1680
tagttaactt agttgaaaca ttgaagtatt agatatttta ttaatataag cactttaaca    1740
aatatggtta taaaaaaaaa tcttcttctt ttcaattcct ttaacattca ttgaaaatct    1800
tcttatttaa caatattttt ccaattagtt caataactcg tcttcaatca tcgaagatat    1860
ttaatgttac ttttttttgaa gtaatgaaat ttacttctaa taatcttgtc ttttttttaa    1920
attggaaatg ggaatagaaa atgataagac gaaattaaat cctcacctac aagataaaag    1980
tttagataag ttttgatagt taattaaatg aatttcaaat tttttaatac ttaaatactt    2040
ctcattaata attgtaaaga tatctacttt tttcattcac tttttacttc aaaaataaat    2100
caaattatgt cacactttca ctgtaataaa ttatatatat ataataaaaa aaagaaaaa     2160 tcttctacct atataagtac gactctctaa tggtgttaag taaaagaaa aatttagtat     2220 aaagtcctag gtagttaaaa agtaaaaagt agaactaatg ccggctttcc ttatcctacg    2280 tataatttc ccataaatcg cccaccttaa ttttttttt ctgatttttc atttggcatc      2340
gaagcttata ttgaattta aacttacgtt aaaatttttt ataatggcac taaaattttt    2400
actaacataa ataattatcc catcctaata aaaatttaaa taaaaaatat ttgattaaaa    2460
atacttaccg ttttttctcgg aaccctcttc tctttgtcca ctcactttcc tcactcattt   2520
```

```
attttttgagc tcacaatatt tttattatat atatatatat atccacaaaa atctctactc    2580
tcatttctca cctaacaaac aaaatctctc attttctgtt ttttgtaaaa ttcttcaatt    2640
taattgaatg acggactata gattatggag taataccaat actactaata catgtgatga    2700
tactatgatg atgattcttt tttatcttc cgatccatcc tctttttggc ctgcttccac     2760
tcccaatcgt ccgactccgg tgaacggagt cggagaaacg atgccgtttt tcaatcaaga    2820
gtcactacag caaaggcttc aggctttaat tgacggtgct cgtgaatcat ggcatatgc    2880 tattttctgg caatcgtcag ttgttgattt tgcgagccaa actgtattgg gttggggaga    2940
tgggtattat aaaggagaag aagataagaa taaacggaga gggtcgtcta gttcagcagc    3000
taattttgtt gctgagcaag agcatagaaa gaaggtgctt cgggagctga attcattaat    3060
atccggtgta caagcttccg ccggaaacgg aactgatgat gcagtggatg aggaagtgac    3120
ggatactgaa tggttttttc tgatttcaat gacccaatcg tttgttaacg gtaacgggct    3180
tccgggcttg gcgatgtaca gttcaagccc aatttgggtt actggaacag agaaattagc    3240
tgcttctcaa tgtgaacggg ccaggcaagc ccaaggtttc gggcttcaga cgattgtgtg    3300
tattccttca gctaacggtg tagtggagct tggttcgact gagctgatat tccaaagctc    3360
ggatttgatg aacaaggtta agtatttgtt taacttcaat attgatatgg ggtctgttac    3420
aggctcaggt tcgggctcag gctcttgtgc tgtgcatcct gagcccgatc cttcggccct    3480
ttggcttacg gatccatctt cctcggttgt ggaacctaag gattcgttaa ttcatagtag    3540
tagtagggat gttcaacttg tgtatggaaa tgagaattct gaaaatcagc agcagcattg    3600
tcaaggattt ttcacaaagg agttgaattt ttcgggttat ggatttgatg gaagtagtaa    3660
taggaataaa actggaattt cttgtaagcc ggagtccagg gagatattga attttggtga    3720
tagtagtaag agattttcag ggcaatcaca gttgggtcct gggcctgggc tcatggagga    3780
gaacaagaac aagaacaaga caagaaaag gtcacttgga tcaaggggaa acaatgaaga    3840
aggaatgctt tcgtttgttt cgggtgtgat cttgccaact tcaacaatgg ggaagtccgg    3900
ggattctgat cactcagatc tcgaagcctc agtggtgaag gaggccgttg tagaacctga    3960
aaagaagccg aggaagcgag ggaggaaacc agccaatgga agggaggagc cattgaatca    4020
cgtggaagcg gagagacaga ggagggagaa attgaatcaa agattctacg cgctcagagc    4080
cgtagtccca aatgtgtcta aaatggataa ggcatcactt ctttgagatg caattgcata    4140
catcaatgag ttgaaatcaa aagttcaaaa ttcagattta gataaagagg agttgaggag    4200
ccaaattgaa tgtttaagga aggaattaac caacaaggga tcatcaaact attccgcctc    4260
ccctccattg aatcaagatg tcaagattgt cgatatggac attgacgtta aggtgattgg    4320
atgggatgct atgattcgta tacaatgtag taaaaagaac catccagctg ccaggctaat    4380
ggcagccctc aaggacttgg acctagacgt gcaccacgct agtgtttccg tggtgaatga    4440
tttgatgatc caacaagcca cagtcaaaat ggggagccgg ctttatgctc aagaacagct    4500
taggatagca ttgacatcaa aaattgctga atcgcgatga aattatgtcc ctagtgagct    4560
atgtataatg ttatcttcta atgagcgaga attttcttct ctgtatataa atgtgatgaa    4620
accaatacta gagatctcga gttgaggctt tttagttcat gtaagattag atatatatat    4680
atgatgcagc ttcatccttt tgtattcttc atccaggaaa taaatgagaa accaataatt    4740
ggtggctgat gatcaacttc atgttattac taattctcgt tccctcttct tttgggatac    4800
aacacttgtc attttacatt aggcaaatta gaagaaaata ctaagcattt tttaattgaa    4860
```

```
cgtaacatgt catgtgtgaa ctagagtcac aagttcaatt catgtaacaa acaatcacct    4920
ttgcatttta gtggagaagg atgcattgag tttcaacttg tacactaact agtcataaga    4980
gattactttg ttataaaaaa aaaaacaatt tttgaccttg ttgtgtatat aatatatgat    5040
tcgagtttgg acgaaagttt ttatttaatt atgatggata tattagttat ggagtacaca    5100
attgccttta ctataaaact tattactttt taataataaa tattttttta atgtaaatat    5160
ataaatataa tcaaaactta atataaatgg atgtattact aatcagttgc ttgttttagt    5220
ctagaagaaa gcaccaaaca aaggggtagg gctgcatttt catttataga gaattcattg    5280
aatttggtca aatcatagct gtattcattg gactaggaaa tatttaaaaa gtatatatat    5340
tattgtttat aataatataa tgtcatgagt atcatttgag tttgaagtga cacaagcccct   5400
ttaaatgcag ttgatttagg cacaaacttt gttattattc ccgccgtcca aatagttgtt    5460
acatttggct tcctaaaaat taatttaact aattttttaaa tttaatttta tattttgaaa   5520
aattaaagtt tataaataca aaaattattt taatttctta catataatta aaaaatatat    5580
ataaaattta tataatttag cgctggaaaa ttattttgaa aacagaggaa gtattattat    5640
tattttggtc ttatgaattg tgtgataaac agtttatatc tgttaatcaa atagacagag    5700
attgatagat gtgacaaaga ttcgtttttt gtttgaggtt ttataaaagg aaaattgtat    5760
aaaatagcaa actaataact taaattaaat ggaatagcta gggtttgatt taattgtgct    5820
ccatagcaaa cgttggcaaa aatttaccag aagtctcgct cgccactctc ccattctcgc    5880
ctctctcgct ttatacatag aagtgtataa tttatgtttc tgttttgtat aaagcgagag    5940
aaaattgtat atacacatgc aaaaatgtat atctttgtgt tatacactta attatataat    6000
ttacaaacat tttacttcaa atattgcagc gaaaaaggcc aaagaattat acaatcgtga    6060
attatataat tgcagtgaaa tacaattttt tctagcttta tacaacagaa gtgtatatat    6120
tgtatttctg ttttttgtata aagcgagaaa acatatatc ttcttgctat acacttataa    6180
ttatgcaata tacatacatt ttaattcgat taaactgtat acaaaactaa ttatacaatt    6240
gcagcgaaat ggcgaattat acaatttagg ccagcgaatt atacactttt atatgtatag    6300
cgaattatac agttttttata tttgctatgg agcgcatata ttatacaaat atgatttttt    6360
tgtttgctat atgtgaaagt tgccctttta taaaagcttt tatgtatagt ttgatttgtt    6420
ttttaaaaa ataaaatatg acaactttag tatcaaaata gattaaattt atatacaata    6480
aatagttata ttttacagcc agccatttat cttttcttttt tttcaagcca caaaatcacc    6540
ttgtagaaag ttattttgtt cgatattttta ttgctaatat ataaaaatat tattataaaa    6600
agcatgtaat atatatataa aaatttgatt tcaaagaata ctttgatcat tataatgata    6660
tgttaatata aataataatt attatagatt aatctgatcg tatattttca gtatacatta    6720
atatatacat ctaaaatatg actgtattaa atatgaacaa aatcatttac atcaccctat    6780
ataatatttt aattaaaaag atgtataaag aagaataaaa aacgctgaag tttaaagcga    6840
atgttattga ccagatcaaa ttgacttgaa gaccaaaatt gaattgttga atacaattaa    6900
ttaatttaaa aatgaccatg ttttacatgt gaaattcatt tatatatata tatatatatc    6960
atatattatt atagtattca catttgttg tttcactga tggttccgtt aagtgttcac      7020
atttctttgt ttaacactaa actttggagg gaaggatgtg aaaataaaaa atttgggtag    7080
aaaattaatc gataatttaa tattgtctaa tttatcttat gtatattatg atcattactc    7140
ccttattatc tttgtatttt tttaatcttg attatcatat tatttagtat ttttttatcc    7200
ttaattttga tatgttttac ttgagtcaaa aatctataga aaataatttt tctattttta    7260
```

```
caagataagg gtaaagatgt gcgaacacaa cttttttgaa gccccactta tgaaattaca    7320
ctgaacatat tgttgtagta actgtacgaa ctcttttttc tttctatata aacaaatgta    7380
taactaaagt atttagtaaa ataaaaatat aattctattt agttcatgaa tgagaccaca    7440
atatgaatgt atagagctgg ggatattttt tgttttgtg tagatggata ttaatcgaag     7500
atgtattggt tcttaatagt aagaataaca atagccatta ccctaaagat tgattcacct    7560 ttatttagg gtataaacca aaaagaatg gacattatta acacgagacc tttagcattt      7620 ccaaaaaaa tgggagaatt ttgttattta tttaaaaga aaaaaaaaa gaacacaccc       7680 ttaacctcaa tatcctcaaa aattcaacca tcaatatcat tattttattt tcatatccta    7740
tgcatttttt attagcttgt aaactttaa ttttcttcct attcttttat acaacaatga     7800
ctctcaattg tttaacctgc caagctctaa aagaacaga ttcacatgag gaactaaggg     7860
aaacactgaa tcatgttaat gataagtcga attttcgtct ttttcagtg ggaatggaga    7920 ggaactggtc agggaacttg gttgaaagac ggaaatatga aaaacgagg ggtcgaacca    7980 taatgggaaa agaaaataat                                                8000

<210> SEQ ID NO 2
<211> LENGTH: 1893
<212> TYPE: DNA
<213> ORGANISM: Solanum lycopersicum

<400> SEQUENCE: 2
atgacggact atagattatg gagtaatacc aatactacta atacatgtga tgatactatg      60
atgatggatt cttttttatc ttccgatcca tcctcttttt ggcctgcttc cactcccaat     120
cgtccgactc cggtgaacgg agtcggagaa acgatgccgt ttttcaatca agagtcacta    180
cagcaaaggc ttcaggcttt aattgacggt gctcgtgaat catgggcata tgctattttc    240
tggcaatcgt cagttgttga tttgcgagc caaactgtat tggttgggg agatgggtat      300 tataaaggag aagaagataa gaataaacgg agagggtcgt ctagttcagc agctaatttt    360
gttgctgagc aagagcatag aaagaaggtg cttcgggagc tgaattcatt aatatccggt    420
gtacaagctt ccgccggaaa cggaactgat gatgcagtgg atgaggaagt gacggatact    480
gaatggtttt ttctgatttc aatgacccaa tcgtttgtta acggtaacgg gcttccgggc    540
ttggcgatgt acagttcaag cccaattttgg gttactggaa cagagaaatt agctgcttct    600
caatgtgaac gggccaggca agcccaaggt ttcgggcttc agacgattgt gtgtattcct    660
tcagctaacg gtgtagtgga gcttggttcg actgagctga tattccaaag ctcggatttg    720
atgaacaagg ttaagtattt gtttaacttc aatattgata ggggtctgt tacaggctca    780 ggttcgggct caggctcttg tgctgtgcat cctgagcccg atccttcggc cctttggctt    840
acggatccat cttcctcggt tgtggaacct aaggattcgt taattcatag tagtagtagg    900
gatgttcaac ttgtgtatgg aaatgagaat tctgaaaatc agcagcagca ttgtcaagga    960 ttttcacaa aggagttgaa ttttcgggt tatggatttg atggaagtag taataggaat      1020
aaaactggaa tttcttgtaa gccggagtcc agggagatat tgaattttgg tgatagtagt    1080
aagagatttt cagggcaatc acagttgggt cctgggcctg gctcatgga ggagaacaag     1140 aacaagaaca agaacaagaa aaggtcactt ggatcaaggg gaaacaatga agaaggaatg    1200
ctttcgtttg tttcgggtgt gatcttgcca acttcaacaa tggggaagtc cggggattct    1260
gatcactcag atctcgaagc ctcagtggtg aaggaggccg ttgtagaacc tgaaaagaag    1320
```

```
ccgaggaagc gagggaggaa accagccaat ggaagggagg agccattgaa tcacgtggaa    1380
gcggagagac agaggaggga gaaattgaat caaagattct acgcgctcag agccgtagtc    1440
ccaaatgtgt ctaaaatgga taaggcatca cttctttgag atgcaattgc atacatcaat    1500
gagttgaaat caaagttcaa aattcagatt tagataaag aggagttgag gagccaaatt    1560
gaatgtttaa ggaaggaatt aaccaacaag ggatcatcaa actattccgc ctcccctcca    1620
ttgaatcaag atgtcaagat tgtcgatatg gacattgacg ttaaggtgat tggatgggat    1680
gctatgattc gtatacaatg tagtaaaaag aaccatccag ctgccaggct aatggcagcc    1740
ctcaaggact tggacctaga cgtgcaccac gctagtgttt ccgtggtgaa tgatttgatg    1800
atccaacaag ccacagtcaa aatggggagc cggctttatg ctcaagaaca gcttaggata    1860
gcattgacat caaaaattgc tgaatcgcga tga                                 1893
```

<210> SEQ ID NO 3
<211> LENGTH: 630
<212> TYPE: PRT
<213> ORGANISM: Solanum lycopersicum
<220> FEATURE:
<221> NAME/KEY: SITE
<222> LOCATION: 493
<223> OTHER INFORMATION: site of stop codon

<400> SEQUENCE: 3

```
Met Thr Asp Tyr Arg Leu Trp Ser Asn Thr Asn Thr Thr Asn Thr Cys
1               5                   10                  15

Asp Asp Thr Met Met Met Asp Ser Phe Leu Ser Ser Asp Pro Ser Ser
                20                  25                  30

Phe Trp Pro Ala Ser Thr Pro Asn Arg Pro Thr Pro Val Asn Gly Val
            35                  40                  45

Gly Glu Thr Met Pro Phe Phe Asn Gln Glu Ser Leu Gln Gln Arg Leu
        50                  55                  60

Gln Ala Leu Ile Asp Gly Ala Arg Glu Ser Trp Ala Tyr Ala Ile Phe
65                  70                  75                  80

Trp Gln Ser Ser Val Val Asp Phe Ala Ser Gln Thr Val Leu Gly Trp
                85                  90                  95

Gly Asp Gly Tyr Tyr Lys Gly Glu Glu Asp Lys Asn Lys Arg Arg Gly
                100                 105                 110

Ser Ser Ser Ala Ala Asn Phe Val Ala Glu Gln Glu His Arg Lys
            115                 120                 125

Lys Val Leu Arg Glu Leu Asn Ser Leu Ile Ser Gly Val Gln Ala Ser
        130                 135                 140

Ala Gly Asn Gly Thr Asp Asp Ala Val Asp Glu Val Thr Asp Thr
145                 150                 155                 160

Glu Trp Phe Phe Leu Ile Ser Met Thr Gln Ser Phe Val Asn Gly Asn
                165                 170                 175

Gly Leu Pro Gly Leu Ala Met Tyr Ser Ser Pro Ile Trp Val Thr
            180                 185                 190

Gly Thr Glu Lys Leu Ala Ala Ser Gln Cys Glu Arg Ala Arg Gln Ala
        195                 200                 205

Gln Gly Phe Gly Leu Gln Thr Ile Val Cys Ile Pro Ser Ala Asn Gly
    210                 215                 220

Val Val Glu Leu Gly Ser Thr Glu Leu Ile Phe Gln Ser Ser Asp Leu
225                 230                 235                 240

Met Asn Lys Val Lys Tyr Leu Phe Asn Phe Asn Ile Asp Met Gly Ser
                245                 250                 255
```

Val Thr Gly Ser Gly Ser Gly Ser Cys Ala Val His Pro Glu
            260                 265                 270

Pro Asp Pro Ser Ala Leu Trp Leu Thr Asp Pro Ser Ser Val Val
        275                 280                 285

Glu Pro Lys Asp Ser Leu Ile His Ser Ser Arg Asp Val Gln Leu
    290                 295                 300

Val Tyr Gly Asn Glu Asn Ser Glu Asn Gln Gln Gln His Cys Gln Gly
305                 310                 315                 320

Phe Phe Thr Lys Glu Leu Asn Phe Ser Gly Tyr Gly Phe Asp Gly Ser
                325                 330                 335

Ser Asn Arg Asn Lys Thr Gly Ile Ser Cys Lys Pro Glu Ser Arg Glu
            340                 345                 350

Ile Leu Asn Phe Gly Asp Ser Ser Lys Arg Phe Ser Gly Gln Ser Gln
        355                 360                 365

Leu Gly Pro Gly Pro Gly Leu Met Glu Glu Asn Lys Asn Lys Asn Lys
    370                 375                 380

Asn Lys Lys Arg Ser Leu Gly Ser Arg Gly Asn Asn Glu Glu Gly Met
385                 390                 395                 400

Leu Ser Phe Val Ser Gly Val Ile Leu Pro Thr Ser Thr Met Gly Lys
                405                 410                 415

Ser Gly Asp Ser Asp His Ser Asp Leu Glu Ala Ser Val Val Lys Glu
            420                 425                 430

Ala Val Val Glu Pro Glu Lys Lys Pro Arg Lys Arg Gly Lys Pro
        435                 440                 445

Ala Asn Gly Arg Glu Glu Pro Leu Asn His Val Glu Ala Glu Arg Gln
    450                 455                 460

Arg Arg Glu Lys Leu Asn Gln Arg Phe Tyr Ala Leu Arg Ala Val Val
465                 470                 475                 480

Pro Asn Val Ser Lys Met Asp Lys Ala Ser Leu Leu Xaa Asp Ala Ile
                485                 490                 495

Ala Tyr Ile Asn Glu Leu Lys Ser Lys Val Gln Asn Ser Asp Leu Asp
            500                 505                 510

Lys Glu Glu Leu Arg Ser Gln Ile Glu Cys Leu Arg Lys Glu Leu Thr
        515                 520                 525

Asn Lys Gly Ser Ser Asn Tyr Ser Ala Ser Pro Pro Leu Asn Gln Asp
    530                 535                 540

Val Lys Ile Val Asp Met Asp Ile Asp Val Lys Val Ile Gly Trp Asp
545                 550                 555                 560

Ala Met Ile Arg Ile Gln Cys Ser Lys Lys Asn His Pro Ala Ala Arg
                565                 570                 575

Leu Met Ala Ala Leu Lys Asp Leu Asp Leu Asp Val His His Ala Ser
            580                 585                 590

Val Ser Val Val Asn Asp Leu Met Ile Gln Gln Ala Thr Val Lys Met
        595                 600                 605

Gly Ser Arg Leu Tyr Ala Gln Glu Gln Leu Arg Ile Ala Leu Thr Ser
    610                 615                 620

Lys Ile Ala Glu Ser Arg
625                 630

<210> SEQ ID NO 4
<211> LENGTH: 201
<212> TYPE: DNA
<213> ORGANISM: Solanum lycopersicum

<400> SEQUENCE: 4

```
ggaagcggag agacagagga gggagaaatt gaatcaaaga ttctacgcgc tcagagccgt        60
agtcccaaat gtgtctaaaa tggataaggc atcacttctt tgagatgcaa ttgcatacat       120
caatgagttg aaatcaaaag ttcaaaattc agatttagat aaagaggagt tgaggagcca       180
aattgaatgt ttaaggaagg a                                                 201
```

<210> SEQ ID NO 5
<211> LENGTH: 8000
<212> TYPE: DNA
<213> ORGANISM: Solanum lycopersicum

<400> SEQUENCE: 5

```
attcaataat taattgtaat tgtctggcat tgttatggtg gttcacatgt caagttgctt        60
ttatattatt tgttattaaa ataaaaatag aaaaatcaat gttattttca cgttcagcat       120
ccaccaaaac gtgctattaa taatttaatg tctaaaacat atctacaaat tatattatat       180
tagtataata tactttatga tatcttgaac aaagacaatt acaagtagga ccaatcaaaa       240
tgattccaca acgtgacgcc aacgcgtaca aataaggatt ttccttttatt ataactttat      300
aataattaac tcaccgtaat taatttgtat gattataatg aaatgactga aacttttttcg      360
ctcttaacaa gaaatctcga tcgaacttta gccatgaaat aaaaataatt gtgttgagag       420
tagaattttcc aaaaatagat tttatagtgt gtaaaattat atttattaat ttttaatatg      480
attatcaaaa taccgaatcg aagaaagtaa gtaaatttta aggaatgtaa tatgtatgtg       540
gtctcaccct tacatgcatt gaatatgtaa agagtgtttt cgaaggacaa ggattttttt       600
gttttttacta ttaatgtatt ttaaaaactt aagacaaaat tatttactca aaatttacat      660
gcgatattgt actaaaacga tttacaatta ttgtaggtac cttaattact ctgatagtgc       720
atggccttta attcaaggg ataccaataa caaaaaagtc catatttgtg atgaatatgt        780
cttatcacaa aaattgagag gaatattatg atagatttaa tgaaaaattt taatatggac       840
aaaagaatat tatgatagat ttaaagaaaa aatttaatat ggacaaaatt tgtgatggac       900
taataaattt acttttttca ttacgaattt ttggagcctc acgttgaaga tccaatgact       960
tgttttcaaa ttagtttcaa agaatggctg agaatagtct ttctaaaaaa gcatcttcaa      1020
tcgatggctt gaatttaatt attaaaagaa ttattatatt tgataatgta ttgattagat      1080
gcacgttatg aatttaaaat ttcattttag acatgaacct aatatttaaa tagacaccaa     1140
cacaagtata tgacgcgaac aagtgatatt taagttatga gttcaaaatt tatgaatcat     1200
tagtcataac taaaaatgtg atactttagg ggataaggat agaagagcaa atttaaattt     1260
tacgtgaacc tttttttattt aaatagaaaa taatagagcg ataaattcat tatttatcga    1320
gtttcaaatc attaaaaata caatatataa tatacgaatt agatgtatat acacatttga     1380
attcaatggt ggactatata atttgatatt taagtaagca aaagtagata aggagttcaa     1440
gtttaaattt gtaaacatag aatttcctat tttagagttt aaggtaaatt tatgtatatt     1500
ttatcgtttg gaatctcatt ttacgatgct acgctaaata ttagaaattg ctaaaaataa     1560
ttgttgttat tgtaatataa tatcaaaatc aacatgattt catttatttt ctttccatat     1620
atgaattatt tccataaagc ctacatgtag gagatatgct aatttaatat ttcctggaaa     1680
tagtaaactt agttgaaaca ttgaagtatt agatatttta ttaatataag cactttaaca     1740
aatatggtta taaaaaaaaa tcttcttctt ttcaattcct ttaacattca ttgaaaatct     1800
tcttatttaa caatattttt ccaattagtt caataactcg tcttcaatca tcgaagatat     1860
```

```
ttaatgttac ttttttgaa gtaatgaaat ttacttctaa taatcttgtc ttttttttaa    1920
attggaaatg gaatagaaa atgataagac gaaattaaat cctcacctac aagataaaag    1980
tttagataag ttttgatagt taattaaatg aatttcaaat tttttaatac ttaaatactt    2040
ctcattaata attgtaaaga tatctacttt tttcattcac tttttacttc aaaaataaat    2100
caaattatgt cacactttca ctgtaataaa ttatatatat ataataaaaa aaaagaaaaa    2160
tcttctacct ataaagtac gactctctaa tggtgttaag taaaaagaaa aatttagtat    2220
aaagtcctag gtagttaaaa agtaaaaagt agaactaatg ccggctttcc ttatcctacg    2280
tataattttc ccataaatcg cccaccttaa ttttttttt ctgattttc atttggcatc     2340 gaagcttata ttagaattta aacttacgtt aaaattttt ataatggcac taaaatttt     2400 actaacataa ataattatcc catcctaata aaaatttaaa taaaaaatat ttgattaaaa    2460
atacttaccg ttttctcgg aaccctcttc tctttgtcca ctcactttcc tcactcattt    2520 attttgagc tcacaatatt tttattatat atatatatat atccacaaaa atctctactc     2580
tcatttctca cctaacaaac aaaatctctc attttctgtt ttttgtaaaa ttcttcaatt    2640
taattgaatg acggactata gattatggag taataccaat actactaata catgtgatga    2700
tactatgatg atggattctt ttttatcttc cgatccatcc tcttttggc ctgcttccac     2760 tcccaatcgt ccgactccgg tgaacggagt cggagaaacg atgccgtttt tcaatcaaga    2820
gtcactacag caaaggcttc aggctttaat tgacggtgct cgtgaatcat gggcatatgc    2880
tattttctgg caatcgtcag ttgttgattt tgcgagccaa actgtattgg gttggggaga    2940
tgggtattat aaaggagaag aagataagaa taaacggaga gggtcgtcta gttcagcagc    3000
taattttgtt gctgagcaag agcatagaaa gaaggtgctt cgggagctga attcattaat    3060
atccggtgta caagcttccg ccggaaacgg aactgatgat gcagtggatg aggaagtgac    3120
ggatactgaa tggttttttc tgatttcaat gacccaatcg tttgttaacg gtaacgggct    3180
tccgggcttg gcgatgtaca gttcaagccc aatttgggtt actggaacag agaaattagc    3240
tgcttctcaa tgtgaacggg ccaggcaagc ccaaggtttc gggcttcaga cgattgtgtg    3300
tattccttca gctaacggtg tagtggagct tggttcgact gagctgatat tccaaagctc    3360
ggatttgatg aacaaggtta agtatttgtt taacttcaat attgtatggg gtctgttac     3420 aggctcaggt tcgggctcag gctcttgtgc tgtgcatcct gagcccgatc cttcggccct    3480
ttggcttacg gatccatctt cctcggttgt ggaacctaag gattcgttaa ttcatagtag    3540
tagtagggat gttcaacttg tgtatggaaa tgagaattct gaaaatcagc agcagcattg    3600
tcaaggattt ttcacaaagg agttgaattt ttcgggttat ggatttgatg gaagtagtaa    3660
taggaataaa actggaattt cttgtaagcc ggagtccagg gagatattga attttggtga    3720
tagtagtaag agattttcag ggcaatcaca gttgggtcct gggcctgggc tcatggagga    3780
gaacaagaac aagaacaaga acaagaaaag gtcacttgga tcaaggggaa caatgaaga    3840 aggaatgctt tcgtttgttt cgggtgtgat cttgccaact tcaacaatgg ggaagtccgg    3900
ggattctgat cactcagatc tcgaagcctc agtggtgaag gaggccgttg tagaacctga    3960
aaagaagccg aggaagcgag ggaggaaacc agccaatgga agggaggagc cattgaatca    4020
cgtggaagcg gagagacaga ggagggagaa attgaatcaa agattctacg cgctcagagc    4080
cgtagtccca aatgtgtcta aaatggataa ggcatcactt cttggagatg caattgcata    4140
catcaatgag ttgaaatcaa aagttcaaaa ttcagattta gataaagagg agttgaggag    4200
```

```
ccaaattgaa tgtttaagga aggaattaac caacaaggga tcatcaaact attccgcctc    4260
ccctccattg aatcaagatg tcaagattgt cgatatggac attgacgtta aggtgattgg    4320
atgggatgct atgattcgta tacaatgtag taaaaagaac catccagctg ccaggctaat    4380
ggcagccctc aaggacttgg acctagacgt gcaccacgct agtgtttccg tggtgaatga    4440
tttgatgatc caacaagcca cagtcaaaat ggggagccgg ctttatgctc aagaacagct    4500
taggatagca ttgacatcaa aaattgctga atcgcgatga aattatgtcc ctagtgagct    4560
atgtataatg ttatcttcta atgagcgaga atttcttct ctgtatataa atgtgatgaa    4620
accaatacta gagatctcga gttgaggctt tttagttcat gtaagattag atatatatat    4680
atgatgcagc ttcatccttt tgtattcttc atccaggaaa taaatgagaa accaataatt    4740
ggtggctgat gatcaacttc atgttattac taattctcgt tccctcttct tttgggatac    4800
aacacttgtc attttacatt aggcaaatta gaagaaaata ctaagcattt tttaattgaa    4860
cgtaacatgt catgtgtgaa ctagagtcac aagttcaatt catgtaacaa acaatcacct    4920
ttgcatttta gtggagaagg atgcattgag tttcaacttg tacactaact agtcataaga    4980
gattactttg ttataaaaaa aaaaacaatt tttgaccttg ttgtgtatat aatatatgat    5040
tcgagtttgg acgaaagttt ttatttaatt atgatggata tattagttat ggagtacaca    5100
attgccttta ctataaaact tattactttt taataataaa tatttttta atgtaaatat    5160 ataaatataa tcaaaactta atataaatgg atgtattact aatcagttgc ttgttttagt    5220
ctagaagaaa gcaccaaaca aaggggtagg gctgcatttt catttataga gaattcattg    5280
aatttggtca aatcatagct gtattcattg gactaggaaa tatttaaaaa gtatatatat    5340
tattgtttat aataatataa tgtcatgagt atcatttgag tttgaagtga cacaagccct    5400
ttaaatgcag ttgatttagg cacaaacttt gttattattc ccgccgtcca aatagttgtt    5460
acatttggct tcctaaaaat taatttaact aattttttaaa tttaatttta tattttgaaa    5520
aattaaagtt tataaataca aaaattattt taatttctta catataatta aaaaatatat    5580
ataaaattta tataatttag cgctggaaaa ttattttgaa aacagaggaa gtattattat    5640
tattttggtc ttatgaattg tgtgataaac agtttatatc tgttaatcaa atagacagag    5700
attgatagat gtgacaaaga ttcgtttttt gtttgaggtt ttataaaagg aaaattgtat    5760
aaaatagcaa actaataact taaattaaat ggaatagcta gggtttgatt taattgtgct    5820
ccatagcaaa cgttggcaaa aatttaccag aagtctcgct cgccactctc ccattctcgc    5880
ctctctcgct ttatacatag aagtgtataa tttatgtttc tgttttgtat aaagcgagag    5940
aaaattgtat atacacatgc aaaaatgtat atctttgtgt tatacactta attatataat    6000
ttacaaacat tttacttcaa atattgcagc gaaaaaggcc aaagaattat acaatcgtga    6060
attatataat tgcagtgaaa tacaattttt tctagcttta tacaacagaa gtgtatatat    6120
tgtatttctg tttttgtata aagcgagaaa aacatatatc ttcttgctat acacttataa    6180
ttatgcaata tacatacatt ttaattcgat taaactgtat acaaaactaa ttatacaatt    6240
gcagcgaaat ggcgaattat acaatttagg ccagcgaatt atacactttt atatgtatag    6300
cgaattatac agttttata tttgctatgg agcgcatata ttatacaaat atgatttttt    6360
tgtttgctat atgtgaaagt tgccctttta taaaagcttt tatgtatagt ttgatttgtt    6420
tttttaaaaa ataaaatatg acaacttag tatcaaaata gattaaattt atatacaata    6480
aatagttata ttttacagcc agccattat ctttctttt tttcaagcca caaaatcacc    6540
ttgtagaaag ttatttttgtt cgatatttta ttgctaatat ataaaaatat tattataaaa    6600
```

-continued

```
agcatgtaat atatatataa aaatttgatt tcaaagaata ctttgatcat tataatgata      6660
tgttaatata aataataatt attatagatt aatctgatcg tatattttca gtatacatta      6720
atatatacat ctaaaatatg actgtattaa atatgaacaa atcatttac atcaccctat       6780
ataatatttt aattaaaaag atgtataaag aagaataaaa aacgctgaag tttaaagcga      6840
atgttattga ccagatcaaa ttgacttgaa gaccaaaatt gaattgttga atacaattaa      6900
ttaatttaaa aatgaccatg ttttacatgt gaaattcatt tatatatata tatatatatc      6960
atatattatt atagtattca cattttgttg tttacactga tggttccgtt aagtgttcac      7020
atttctttgt ttaacactaa actttggagg gaaggatgtg aaaataaaaa atttgggtag      7080
aaaattaatc gataatttaa tattgtctaa tttatcttat gtatattatg atcattactc      7140
ccttattatc tttgtatttt tttaatcttg attatcatat tatttagtat ttttttatcc      7200
ttaattttga tatgttttac ttgagtcaaa aatctataga aaataatttt tctattttta      7260
caagataagg gtaaagatgt gcgaacacaa ctttttttgaa gccccactta tgaaattaca     7320
ctgaacatat tgttgtagta actgtacgaa ctctttttc tttctatata aacaaatgta       7380
taactaaagt atttagtaaa ataaaaatat aattctattt agttcatgaa tgagaccaca      7440
atatgaatgt atagagctgg ggatattttt tgttttgtg tagatggata ttaatcgaag       7500
atgtattggt tcttaatagt aagaataaca atagccatta ccctaaagat tgattcacct     7560
ttatttttagg gtataaacca aaaagaatg gacattatta acacgagacc tttagcatt      7620
ccaaaaaaaa tgggagaatt ttgttattta tttaaaaaga aaaaaaaaa gaacacaccc      7680
ttaacctcaa tatcctcaaa aattcaacca tcaatatcat tattttattt tcatatccta      7740
tgcatttttt attagcttgt aaactttaa ttttcttcct attctttttat acaacaatga     7800
ctctcaattg tttaacctgc caagctctaa aaagaacaga ttcacatgag gaactaaggg      7860
aaacactgaa tcatgttaat gataagtcga attttcgtct ttttcagtg ggaatggaga      7920
ggaactggtc agggaacttg gttgaaagac ggaaatatga aaaacgagg ggtcgaacca      7980
taatgggaaa agaaaataat                                                   8000
```

<210> SEQ ID NO 6
<211> LENGTH: 1893
<212> TYPE: DNA
<213> ORGANISM: Solanum lycopersicum

<400> SEQUENCE: 6

```
atgacggact atagattatg gagtaatacc aatactacta atacatgtga tgatactatg       60
atgatggatt cttttttatc ttccgatcca tcctcttttt ggcctgcttc cactcccaat       120
cgtccgactc cggtgaacgg agtcggagaa acgatgccgt ttttcaatca agagtcacta      180
cagcaaaggc ttcaggcttt aattgacggt gctcgtgaat catgggcata tgctatttc       240
tggcaatcgt cagttgttga ttttgcgagc caaactgtat tgggttgggg agatgggtat      300
tataaaggag aagaagataa gaataaacgg agagggtcgt ctagttcagc agctaatttt      360
gttgctgagc aagagcatag aaagaaggtg cttcgggagc tgaattcatt aatatccggt      420
gtacaagctt ccgccggaaa cggaactgat gatgcagtgg atgaggaagt gacggatact      480
gaatggtttt ttctgatttc aatgacccaa tcgtttgtta acggtaacgg gcttccgggc      540
ttggcgatta cagttcaag cccaatttgg gttactggaa cagagaaatt agctgcttct      600
caatgtgaac gggccaggca agcccaaggt ttcgggcttc agacgattgt gtgtattcct      660
```

```
tcagctaacg gtgtagtgga gcttggttcg actgagctga tattccaaag ctcggatttg    720
atgaacaagg ttaagtattt gtttaacttc aatattgata tggggtctgt tacaggctca    780
ggttcgggct caggctcttg tgctgtgcat cctgagcccg atccttcggc cctttggctt    840
acggatccat cttcctcggt tgtggaacct aaggattcgt taattcatag tagtagtagg    900
gatgttcaac ttgtgtatgg aaatgagaat tctgaaaatc agcagcagca ttgtcaagga    960
tttttcacaa aggagttgaa ttttcgggt tatggatttg atggaagtag taataggaat    1020
aaaactggaa tttcttgtaa gccggagtcc agggagatat tgaattttgg tgatagtagt    1080
aagagatttt cagggcaatc acagttgggt cctgggcctg ggctcatgga ggagaacaag    1140
aacaagaaca agaacaagaa aaggtcactt ggatcaaggg gaaacaatga agaaggaatg    1200 cttcgtttg tttcgggtgt gatcttgcca acttcaacaa tggggaagtc cggggattct    1260
gatcactcag atctcgaagc ctcagtggtg aaggaggccg ttgtagaacc tgaaaagaag    1320
ccgaggaagc gagggaggaa accagccaat ggaagggagg agccattgaa tcacgtggaa    1380
gcggagagac agaggaggga gaaattgaat caaagattct acgcgctcag agccgtagtc    1440
ccaaatgtgt ctaaaatgga taaggcatca cttcttggag atgcaattgc atacatcaat    1500
gagttgaaat caaaagttca aaattcagat ttagataaag aggagttgag gagccaaatt    1560
gaatgtttaa ggaaggaatt aaccaacaag ggatcatcaa actattccgc ctcccctcca    1620
ttgaatcaag atgtcaagat tgtcgatatg gacattgacg ttaaggtgat tggatgggat    1680
gctatgattc gtatacaatg tagtaaaaag aaccatccag ctgccaggct aatggcagcc    1740
ctcaaggact tggacctaga cgtgcaccac gctagtgttt ccgtggtgaa tgatttgatg    1800
atccaacaag ccacagtcaa aatggggagc cggctttatg ctcaagaaca gcttaggata    1860
gcattgacat caaaaattgc tgaatcgcga tga                                 1893

<210> SEQ ID NO 7
<211> LENGTH: 630
<212> TYPE: PRT
<213> ORGANISM: Solanum lycopersicum

<400> SEQUENCE: 7

Met Thr Asp Tyr Arg Leu Trp Ser Asn Thr Asn Thr Thr Asn Thr Cys
1               5                   10                  15

Asp Asp Thr Met Met Met Asp Ser Phe Leu Ser Asp Pro Ser Ser
            20                  25                  30

Phe Trp Pro Ala Ser Thr Pro Asn Arg Pro Thr Pro Val Asn Gly Val
        35                  40                  45

Gly Glu Thr Met Pro Phe Phe Asn Gln Glu Ser Leu Gln Gln Arg Leu
    50                  55                  60

Gln Ala Leu Ile Asp Gly Ala Arg Glu Ser Trp Ala Tyr Ala Ile Phe
65                  70                  75                  80

Trp Gln Ser Ser Val Val Asp Phe Ala Ser Gln Thr Val Leu Gly Trp
                85                  90                  95

Gly Asp Gly Tyr Tyr Lys Gly Glu Glu Asp Lys Asn Lys Arg Arg Gly
            100                 105                 110

Ser Ser Ser Ala Ala Asn Phe Val Ala Glu Gln Glu His Arg Lys
        115                 120                 125

Lys Val Leu Arg Glu Leu Asn Ser Leu Ile Ser Gly Val Gln Ala Ser
    130                 135                 140

Ala Gly Asn Gly Thr Asp Asp Ala Val Asp Glu Glu Val Thr Asp Thr
145                 150                 155                 160
```

```
Glu Trp Phe Phe Leu Ile Ser Met Thr Gln Ser Phe Val Asn Gly Asn
                165                 170                 175

Gly Leu Pro Gly Leu Ala Met Tyr Ser Ser Pro Ile Trp Val Thr
            180                 185                 190

Gly Thr Glu Lys Leu Ala Ala Ser Gln Cys Glu Arg Ala Arg Gln Ala
        195                 200                 205

Gln Gly Phe Gly Leu Gln Thr Ile Val Cys Ile Pro Ser Ala Asn Gly
    210                 215                 220

Val Val Glu Leu Gly Ser Thr Glu Leu Ile Phe Gln Ser Ser Asp Leu
225                 230                 235                 240

Met Asn Lys Val Lys Tyr Leu Phe Asn Phe Asn Ile Asp Met Gly Ser
                245                 250                 255

Val Thr Gly Ser Gly Ser Gly Ser Cys Ala Val His Pro Glu
            260                 265                 270

Pro Asp Pro Ser Ala Leu Trp Leu Thr Asp Pro Ser Ser Val Val
        275                 280                 285

Glu Pro Lys Asp Ser Leu Ile His Ser Ser Arg Asp Val Gln Leu
    290                 295                 300

Val Tyr Gly Asn Glu Asn Ser Glu Asn Gln Gln His Cys Gln Gly
305                 310                 315                 320

Phe Phe Thr Lys Glu Leu Asn Phe Ser Gly Tyr Gly Phe Asp Gly Ser
                325                 330                 335

Ser Asn Arg Asn Lys Thr Gly Ile Ser Cys Lys Pro Glu Ser Arg Glu
            340                 345                 350

Ile Leu Asn Phe Gly Asp Ser Ser Lys Arg Phe Ser Gly Gln Ser Gln
        355                 360                 365

Leu Gly Pro Gly Pro Gly Leu Met Glu Glu Asn Lys Asn Lys Asn Lys
    370                 375                 380

Asn Lys Lys Arg Ser Leu Gly Ser Arg Gly Asn Asn Glu Glu Gly Met
385                 390                 395                 400

Leu Ser Phe Val Ser Gly Val Ile Leu Pro Thr Ser Thr Met Gly Lys
                405                 410                 415

Ser Gly Asp Ser Asp His Ser Asp Leu Glu Ala Ser Val Val Lys Glu
            420                 425                 430

Ala Val Val Glu Pro Glu Lys Lys Pro Arg Lys Arg Gly Arg Lys Pro
        435                 440                 445

Ala Asn Gly Arg Glu Glu Pro Leu Asn His Val Glu Ala Glu Arg Gln
    450                 455                 460

Arg Arg Glu Lys Leu Asn Gln Arg Phe Tyr Ala Leu Arg Ala Val Val
465                 470                 475                 480

Pro Asn Val Ser Lys Met Asp Lys Ala Ser Leu Leu Gly Asp Ala Ile
                485                 490                 495

Ala Tyr Ile Asn Glu Leu Lys Ser Lys Val Gln Asn Ser Asp Leu Asp
            500                 505                 510

Lys Glu Glu Leu Arg Ser Gln Ile Glu Cys Leu Arg Lys Glu Leu Thr
        515                 520                 525

Asn Lys Gly Ser Ser Asn Tyr Ser Ala Ser Pro Pro Leu Asn Gln Asp
    530                 535                 540

Val Lys Ile Val Asp Met Asp Ile Asp Val Lys Val Ile Gly Trp Asp
545                 550                 555                 560

Ala Met Ile Arg Ile Gln Cys Ser Lys Lys Asn His Pro Ala Ala Arg
                565                 570                 575
```

```
Leu Met Ala Ala Leu Lys Asp Leu Asp Leu Asp Val His His Ala Ser
            580                 585                 590
Val Ser Val Val Asn Asp Leu Met Ile Gln Gln Ala Thr Val Lys Met
        595                 600                 605
Gly Ser Arg Leu Tyr Ala Gln Glu Gln Leu Arg Ile Ala Leu Thr Ser
    610                 615                 620
Lys Ile Ala Glu Ser Arg
625             630

<210> SEQ ID NO 8
<211> LENGTH: 201
<212> TYPE: DNA
<213> ORGANISM: Solanum lycopersicum

<400> SEQUENCE: 8
ggaagcggag agacagagga gggagaaatt gaatcaaaga ttctacgcgc tcagagccgt      60
agtcccaaat gtgtctaaaa tggataaggc atcacttctt ggagatgcaa ttgcatacat    120
caatgagttg aaatcaaaag ttcaaaattc agatttagat aaagaggagt tgaggagcca    180
aattgaatgt ttaaggaagg a                                              201

<210> SEQ ID NO 9
<211> LENGTH: 6700
<212> TYPE: DNA
<213> ORGANISM: Capsicum annuum

<400> SEQUENCE: 9
ctctaaatat gtaaaatgaa ttaggaataa atgcacatat tttccttcgc agaaagagat      60
agcaacatgg acctcaaaca gcctcttggc atattattta cttaactatc aaaatggtta    120
aatgtgtatt ttataataac taaaagctta acaataaag taataaatct tattagtata     180 tttatttct atctgtatca tcgactcctt catatgtcta taattaatac ttttgctaa      240 acataacatt atttcttttt ataagttgaa acactgaatt atcacacttt catattatat    300
aaactcgtaa ctgaaaatgt ttcaaaaata gttatagata atatcttttc aattcctaaa    360
ttcaactcct caacccaagg aaagaatgga aatggattca tatacgttga tttctcattc    420
tttttctatc atttcattta ccttcctatt gagagggaaa tggaatcaag aaaatgatca    480
accacattat tagatactca cttcgttagt gttatttgtt aaatattgac ttgatacact    540
gcacctttgg gtgtggttga gttggtttga ggggtgactt tcaaagcgaa ggtcgcggta    600
tcaattccct ctaatgcttt ttcaatctag ctcgtcacac taggtttacc tagtgcggtt    660
tacatctcct gtgtggttta cgagtgatta tacagtgagg ggtttaccca atacacacaa    720
agtgctcacc cgaagggcag aggctagtgg ctgggtaaac ccgaagggca gaggctagtg    780 gctgcgggt ttacccagtg cgcacaaagt gctcacccga ctttcctgaa gtttcaaaaa     840
atatatatat atatatatat tgacttgata catttcttaa agagcaaaat aaattaaaaa    900
ttaaataata actcaactct acattttctt aattgaacag aaaaataagt aactatgttt    960
tggtacagtg aataaataga agtggtcgaa aaagtatttt ctccattcta gaagtacacc   1020
aagcttctaa taagagtcaa cacacctaag tttaaacgta attcaaacat caatttctta   1080
gtttttaaaa ctaaattatg gatattaaaa aattataaga aaacaaatg atactcctta    1140 caatttattt ggttatcaga ttacaactga ttcgacttgt caaataataa tgattgaaat   1200
atatgatagg atatgtcgca gtaagagatt tgaatcataa taggtgagga taaacgctat   1260
tgcaaaaaaa gttttaatt ttcaccaaat attgggaaac tacttcaaat atactccatc    1320
```

```
aatttacatt taaagaataa ataattaata ttaaggataa aagatttttt tttttaatct    1380
tatttttgat atatcaaaat gataagtata aataaaaatt caattaaaga aataatgtaa    1440
cgtaaaagtg aacagaggga atccttttta gtagacattt atatttagtt gaagtttaaa    1500
aatcccaaat aattcaaatt aaagttgact ttcataaaca cttattaaaa aaatcagcca    1560
aagataatac atttataaaa atgtaatttt caaatgaatt aactagacgt aaattttttt    1620
tttttcaaaa gtaattttt aataagttat tttaataaaa aagcttctca aaataagaaa    1680 ttttttatagc cacttgacca aacaagtctc ccaaacatga atttgaatta attttttaaaa  1740 aaatttcgca agtaaaaact aaaaagactt cttaaaatgt gttttcaaa atttaaattc    1800 tattcaagtt tgatattatc ctaaaattat tgaccatatt agaaatgttt gattgaaatt   1860
atttcttgaa aattagaaaa aaaatgaggt tctttgatat tttttttgaag cagtggtatg  1920 gccatataag aatacactca ttatatgtta ttgattggtt gctgattaaa aagttcgtc    1980 tttttaattt tttattcgat atttatattg aaactttgat taccttactg taagatgtga   2040
catttctaac aaaattatat ttatattaaa aattttaaaa ttaaaacatt taattaaggg   2100
tgagccagat ccactaccgc accgtagccg cgacccatat ggtacaagag gagtagtagt   2160
gatgttggcg attaattggc gggtccttcg tggaacccgc cagtctcttt cctcattctc   2220
ccaaattcag ctcaaattca cctcaaataa aacccaaact caaattccac tcttattaac   2280
caaacccaat atttctctct cattttctc cgccacaccc ctctatcctc attctctctc    2340
tctctacaca ccattttcac ctgttttctg ctgtgtgttt tatggaatga ctgattacag   2400
cttgcccacc atgaatctct ggaataacag tactactgat gacaacgttt ctatgatgga   2460
ggcttttatg tcttccgatc tttcttttg gggtggtact actacttcta gtgctactgc    2520
tactgctgct gctcttgcta atcccaatta tacttcaact gtttaccctc ctcctggcgc   2580
ttcttgtgca tcttccgtaa cggctacagc tgctgctgtg actgttgatg cgtcaaaaac   2640
catgccattt ttcaaccagg agacgctaca gcagcgtctt cagaccctaa tagacggtgc   2700
tcgtgagacg tggacgtatg ctatcttctg gcagtcgtct gatttagatt tctcgagtcc   2760
gtctgtgttg ggttggggtg atggttatta caaaggggag gaggataaaa acaagaggaa   2820
attatctgtt tcttctccgg cttatattgc tgagcaggaa catcggaaga aggttcttag   2880
agagctgaat tcgttgattt cagggacaca aactggtaca gacgatgctg ttgatgaaga   2940
agttaccgat accgaatggt tcttttctat ctccatgact caatcttttg tcaacgggaa   3000
cgggcttccg ggccaggcta tgtgcagttc cagcccgatt tgggttgccg gagtagagaa   3060
attggctgct tctcactgtg aacgggctcg gcaggcccaa gggttcgggc ttcagacgat   3120
ggtgtgtatc ccttcagcta acggtgttgt tgaattgggt tcgacggagt tgattatcca   3180
gagttctgat ctgatgaata aggttagagt actgttcaat ttcaataatg atttggggtc   3240
aggttcatgg gctgtgcagc cggagagcga tccgtcagcg ctttggttga cggagccatc   3300
ttcctcaggt atggaagtta gagagtcttt aaatacagtt caaacaagtt caattccatc   3360
aagtaatagt aataagcaaa ttgcgtatgg aaatgagaac aatgatcatc catctggaaa   3420
tgggaatggt catagttctt ataatcagca gcatcctcat caacaaacac aaggattttt   3480
cacgaaggag ttaaacttttt cggactttgg gttcgatgga agtagtaata ggaacgggaa   3540
ttcatcgctc tcttgcaagc ctgagtctgg ggaaatcttg aattttggtg atagtacgaa   3600
gaaaagtgct tgtagtgcaa atgggaactt gttttcgggc cattcccaat ttggggcagg   3660
```

| | |
|---|---|
| tgaggagaac aagaacaaga ccaagaaaag gtcagctact tccaggggaa gcaatgaaga | 3720 |
| aggaatgctt tcatttgttt cgggtacagt tttgccttct tccggtatga agtcaggcgg | 3780 |
| aggcgaagac tctgaccatt cagatcttga agcttcggtg gtgaaagaag ctgatagtag | 3840 |
| tagagttgta gaaccggaaa agaagccaag gaagcgagga aggaagcctg ctaatggaag | 3900 |
| ggaggaacct ttgaatcatg ttgaggcaga gaggcaaagg agggagaaat tgaaccaaag | 3960 |
| attctacgcg cttagagctg ttgtaccgaa tgtgtctaag atggacaagg catcacttct | 4020 |
| tggagatgca atttcataca taaatgagtt gaaatcgaag cttcacaata cagagtcaga | 4080 |
| taaagaagac ttgaagagcc aaatagagga tttgaagaaa gaattagcta gtaaagaatc | 4140 |
| aaggcgccct ggtcaaccac caccaaacca agatctcaag atgtctagcc acaccggaac | 4200 |
| caagattgta gacgcggaga tagacattaa gataatggga tgggatgtta tgattcgtgt | 4260 |
| acaatctaat aaaaagaatc atccagccgc aaggtttatg gcggccctca tggaactaga | 4320 |
| cctagatgtg aaccatgcca gtgtttcatt ggtgaacgag ttgatgatcc agcaagccac | 4380 |
| agtgaaaatg agtagccgtc attacactga agagcagctt aggatagcat tgatgtcaag | 4440 |
| aattgctgaa acgcgctaaa aaagaccctg gaaagtagat agaactcaaa gaaagcatgt | 4500 |
| gggctttgat ggcgctctgg ttgctgcagc tctatgtaat gttttttgtta tgaattagag | 4560 |
| atttcatcag gctatcttcg tgttattttt cgaacttgta ccttaggtgg ttgtcgaaat | 4620 |
| attcttgtac ataaatgtta ttacccgaaa actcaacata atcgggcttt agctcatgta | 4680 |
| attaaacata tattccaact ccgtcttgtc tgttagattg catctatcat tatgtattct | 4740 |
| ttgtccatgc ataaatgaag aaatttgatg gcaggtgaat ttgattttga agcaaatgtg | 4800 |
| atttactgtc gtgctgctta ttcttatacc caattttttga gctgcattag gattgtgtga | 4860 |
| agtactttaa gctattcatt catgagaaaa atgtgaaaga gatcatcatt tcagaaatat | 4920 |
| gcactatttc tccaattcaa acttcatgtt caaattgtat taaataattg tattggaggt | 4980 |
| cattgcttac gacctttatg catcacattt tgactaaaaa caataacgga ttatttcatg | 5040 |
| agaatatttg gatttacata tacacctcag aaaaactatc atctttcatt tgagtttttt | 5100 |
| aatgtcatac tccatccgac tcaatttaat ttgcgccgaa gaatgccaaa aaagtttcac | 5160 |
| atttatggtc aatagatgag taatctcctt ataaggcttg gattatcctc tttcctaatg | 5220 |
| ctcaaaaggt gtaagtttag ccatgaccta attttatata tactttttttt ttgacatttc | 5280 |
| tttaatctta atttttcata cgacatattt aagattataa aattaaataa tattttaata | 5340 |
| cattctatct tgtgtcaagt taaatgagac aaacaaatta taacaaagga agcatcaaat | 5400 |
| aaaataggaa agaaggaaaa agggatttcg taaaagagcg ataagataag gtgatagttt | 5460 |
| gatagactag attggactag atgcaacagc aaaatagaac aggaaactac aaggaactag | 5520 |
| tccatttatt catttggctg cttgctcgtt tatattgtga attgtatatc tccacatatt | 5580 |
| ttattctaat aaagatatca ggaagaaggc atgtgtctta ttattttcct ttaggagaat | 5640 |
| acactgaact tggttcttct tttggtccct attgtctact atagaccaat gtatattttc | 5700 |
| cataatagta ttggcataac atgctaaagt attttccata atagtattgg caagaaacgc | 5760 |
| catgaatatc atgtaggttg aaactgacag caacgtttca aattcacttc atttgaactt | 5820 |
| tcacttcacc caagtacagt ctccccgtcc gaagcaggat tttcatcaaa gagatgcaac | 5880 |
| atttaccata aataaatttt ctccccccca tccctctctc tctatatatt agtaactttg | 5940 |
| gatccagatg aaccctttttc cgcctcacaa gtttcaccca agttccaagt atatgttact | 6000 |
| ctagaagttt taactttctt tttagtaatt ctttgttaat atgttgtccc tatactagta | 6060 |

```
tctggacatg ccactactga aaaattcaaa atttaccttc attctttaag gtaatttaca    6120
attcaatctt taaggttttt atattgacct tattatattt taaagttatg aatttatatt    6180
tattattatt actttctata tttttaaata agtgacattt tagtcttttc attttatttc    6240
taaataactt ggtgttttag ataattaaga agatattaat gatgttatta taagtttacc    6300 acttttaaa taaagaaagt tttacatgac ttaaggagta ctaagaatta catcatttcc     6360
aaagaaatat taagaataag ttggtaaaaa tactatttat ttaaaaataa aaaaaaataa    6420
ttttaacaaa ctaatacata taaatttata tttcctattg aaaatacaat tcatactaat    6480
ctcaacgccg ctcggtaaaa ttagatccgc ttcactttaa ctgctaatta ttgaataaag    6540
tgtagggaca aatttgatgt aaataaaatc atctactcca ctaatatatt aatttgtttt    6600
taatttaata tatattttc atacactaga caacaaagaa ttgtgacgtg acgcaaattt     6660
ggtggaagtg gacatgcaga caaaaaagat catgtgttac                          6700

<210> SEQ ID NO 10
<211> LENGTH: 2073
<212> TYPE: DNA
<213> ORGANISM: Capsicum annuum

<400> SEQUENCE: 10
atgactgatt acagcttgcc caccatgaat ctctggaata acagtactac tgatgacaac      60
gtttctatga tggaggcttt tatgtcttcc gatctttctt tttggggtgg tactactact     120
tctagtgcta ctgctactgc tgctgctctt gctaatccca attatacttc aactgtttac     180
cctcctcctg gcgcttcttg tgcatcttcc gtaacggcta cagctgctgc tgtgactgtt     240
gatgcgtcaa aaaccatgcc atttttcaac caggagacgc tacagcagcg tcttcagacc     300
ctaatagacg gtgctcgtga gacgtggacg tatgctatct tctggcagtc gtctgattta     360
gatttctcga gtccgtctgt gttggggtgg ggtgatggtt attacaaagg ggaggaggat     420
aaaaacaaga ggaaattatc tgtttcttct ccggcttata ttgctgagca ggaacatcgg     480
aagaaggttc ttagagagct gaattcgttg atttcaggga cacaaactgg tacagacgat    540
gctgttgatg aagaagttac cgataccgaa tggttctttc ttatctccat gactcaatct    600
tttgtcaacg ggaacgggct tccgggccag gctatgtgca gttccagccc gatttgggtt    660
gccggagtag agaaattggc tgcttctcac tgtgaacggg ctcggcaggc ccaagggttc    720
gggcttcaga cgatggtgtg tatcccttca gctaacggtg ttgttgaatt gggttcgacg    780
gagttgatta tccagagttc tgatctgatg aataaggtta gagtactgtt caatttcaat    840
aatgatttgg ggtcaggttc atgggctgtg cagccggaga gcgatccgtc agcgctttgg    900
ttgacggagc atcttcctc aggtatggaa gttagagagt ctttaaatac agttcaaaca     960
agttcaattc catcaagtaa tagtaataag caaattgcgt atggaaatga gaacaatgat   1020
catccatctg gaaatgggaa tggtcatagt tcttataatc agcagcatcc tcatcaacaa   1080
acacaaggat tttcacgaa ggagttaaac ttttcggact tgggttcga tggaagtagt    1140 aataggaacg ggaattcatc gctctcttgc aagcctgagt ctggggaaat cttgaatttt   1200
ggtgatagta cgaagaaaag tgcttgtagt gcaaatggga acttgttttc gggccattcc   1260
caatttgggg caggtgagga gaacaagaac aagaccaaga aaggtcagc tacttccagg   1320 ggaagcaatg aagaaggaat gctttcattt gtttcgggta cagttttgcc ttcttccggt   1380
atgaagtcag gcggaggcga agactctgac cattcagatc ttgaagcttc ggtggtgaaa   1440
```

```
gaagctgata gtagtagagt tgtagaaccg gaaaagaagc caaggaagcg aggaaggaag    1500
cctgctaatg gaagggagga acctttgaat catgttgagg cagagaggca aggaggag      1560 aaattgaacc aaagattcta cgcgcttaga gctgttgtac cgaatgtgtc taagatggac    1620
aaggcatcac ttcttggaga tgcaatttca tacataaatg agttgaaatc gaagcttcac    1680
aatacagagt cagataaaga agacttgaag agccaaatag aggatttgaa gaaagaatta    1740
gctagtaaag aatcaaggcg ccctggtcaa ccaccaccaa accaagatct caagatgtct    1800
agccacaccg gaaccaagat tgtagacgcg gagatagaca ttaagataat gggatgggat    1860
gttatgattc gtgtacaatc taataaaaag aatcatccag ccgcaaggtt tatggcggcc    1920
ctcatggaac tagacctaga tgtgaaccat gccagtgttt cattggtgaa cgagttgatg    1980
atccagcaag ccacagtgaa aatgagtagc cgtcattaca ctgaagagca gcttaggata    2040
gcattgatgt caagaattgc tgaaacgcgc taa                                 2073
```

<210> SEQ ID NO 11
<211> LENGTH: 690
<212> TYPE: PRT
<213> ORGANISM: Capsicum annuum

<400> SEQUENCE: 11

Met Thr Asp Tyr Ser Leu Pro Thr Met Asn Leu Trp Asn Asn Ser Thr
1               5                   10                  15

Thr Asp Asp Asn Val Ser Met Met Glu Ala Phe Met Ser Ser Asp Leu
            20                  25                  30

Ser Phe Trp Gly Gly Thr Thr Thr Ser Ser Ala Thr Ala Thr Ala Ala
        35                  40                  45

Ala Leu Ala Asn Pro Asn Tyr Thr Ser Thr Val Tyr Pro Pro Pro Gly
    50                  55                  60

Ala Ser Cys Ala Ser Ser Val Thr Ala Thr Ala Ala Val Thr Val
65                  70                  75                  80

Asp Ala Ser Lys Thr Met Pro Phe Phe Asn Gln Glu Thr Leu Gln Gln
                85                  90                  95

Arg Leu Gln Thr Leu Ile Asp Gly Ala Arg Glu Thr Trp Thr Tyr Ala
            100                 105                 110

Ile Phe Trp Gln Ser Ser Asp Leu Asp Phe Ser Ser Pro Ser Val Leu
        115                 120                 125

Gly Trp Gly Asp Gly Tyr Tyr Lys Gly Glu Glu Asp Lys Asn Lys Arg
    130                 135                 140

Lys Leu Ser Val Ser Ser Pro Ala Tyr Ile Ala Glu Gln Glu His Arg
145                 150                 155                 160

Lys Lys Val Leu Arg Glu Leu Asn Ser Leu Ile Ser Gly Thr Gln Thr
                165                 170                 175

Gly Thr Asp Asp Ala Val Asp Glu Glu Val Thr Asp Thr Glu Trp Phe
            180                 185                 190

Phe Leu Ile Ser Met Thr Gln Ser Phe Val Asn Gly Asn Gly Leu Pro
        195                 200                 205

Gly Gln Ala Met Cys Ser Ser Pro Ile Trp Val Ala Gly Val Glu
    210                 215                 220

Lys Leu Ala Ala Ser His Cys Glu Arg Ala Arg Gln Ala Gln Gly Phe
225                 230                 235                 240

Gly Leu Gln Thr Met Val Cys Ile Pro Ser Ala Asn Gly Val Val Glu
                245                 250                 255

Leu Gly Ser Thr Glu Leu Ile Ile Gln Ser Ser Asp Leu Met Asn Lys

```
                260             265             270
Val Arg Val Leu Phe Asn Phe Asn Asn Asp Leu Gly Ser Gly Ser Trp
            275             280             285

Ala Val Gln Pro Glu Ser Asp Pro Ser Ala Leu Trp Leu Thr Glu Pro
            290             295             300

Ser Ser Ser Gly Met Glu Val Arg Glu Ser Leu Asn Thr Val Gln Thr
305             310             315             320

Ser Ser Ile Pro Ser Ser Asn Ser Asn Lys Gln Ile Ala Tyr Gly Asn
                325             330             335

Glu Asn Asn Asp His Pro Ser Gly Asn Gly Asn Gly His Ser Ser Tyr
                340             345             350

Asn Gln Gln His Pro His Gln Thr Gln Gly Phe Phe Thr Lys Glu
            355             360             365

Leu Asn Phe Ser Asp Phe Gly Phe Asp Gly Ser Ser Asn Arg Asn Gly
            370             375             380

Asn Ser Ser Leu Ser Cys Lys Pro Glu Ser Gly Glu Ile Leu Asn Phe
385             390             395             400

Gly Asp Ser Thr Lys Lys Ser Ala Cys Ser Ala Asn Gly Asn Leu Phe
                405             410             415

Ser Gly His Ser Gln Phe Gly Ala Gly Glu Glu Asn Lys Asn Lys Thr
                420             425             430

Lys Lys Arg Ser Ala Thr Ser Arg Gly Ser Asn Glu Glu Gly Met Leu
            435             440             445

Ser Phe Val Ser Gly Thr Val Leu Pro Ser Ser Gly Met Lys Ser Gly
            450             455             460

Gly Gly Glu Asp Ser Asp His Ser Asp Leu Glu Ala Ser Val Val Lys
465             470             475             480

Glu Ala Asp Ser Ser Arg Val Val Glu Pro Lys Lys Pro Arg Lys
                485             490             495

Arg Gly Arg Lys Pro Ala Asn Gly Arg Glu Glu Pro Leu Asn His Val
            500             505             510

Glu Ala Glu Arg Gln Arg Arg Glu Lys Leu Asn Gln Arg Phe Tyr Ala
            515             520             525

Leu Arg Ala Val Val Pro Asn Val Ser Lys Met Asp Lys Ala Ser Leu
            530             535             540

Leu Gly Asp Ala Ile Ser Tyr Ile Asn Glu Leu Lys Ser Lys Leu His
545             550             555             560

Asn Thr Glu Ser Asp Lys Glu Asp Leu Lys Ser Gln Ile Glu Asp Leu
                565             570             575

Lys Lys Glu Leu Ala Ser Lys Glu Ser Arg Arg Pro Gly Gln Pro Pro
            580             585             590

Pro Asn Gln Asp Leu Lys Met Ser Ser His Thr Gly Thr Lys Ile Val
            595             600             605

Asp Ala Glu Ile Asp Ile Lys Ile Met Gly Trp Asp Val Met Ile Arg
610             615             620

Val Gln Ser Asn Lys Lys Asn His Pro Ala Arg Phe Met Ala Ala
625             630             635             640

Leu Met Glu Leu Asp Leu Asp Val Asn His Ala Ser Val Ser Leu Val
                645             650             655

Asn Glu Leu Met Ile Gln Gln Ala Thr Val Lys Met Ser Ser Arg His
                660             665             670

Tyr Thr Glu Glu Gln Leu Arg Ile Ala Leu Met Ser Arg Ile Ala Glu
            675             680             685
```

Thr Arg
    690

<210> SEQ ID NO 12
<211> LENGTH: 5200
<212> TYPE: DNA
<213> ORGANISM: Cucumis sativus

<400> SEQUENCE: 12

```
ttttaaattt gaggcgtcat aaagttagtt tatatgtgag aggtatcttg ttgaattttt      60
taagttttta aaattttta ttcaataaag ttctaaaatt tgctctattt tttttctgtt     120
tggcatccaa ctgtagacat acttttcaa aattttaaca ctcggtttgg tatttgaatt     180
taattaaata aagctatact caacaaaaaa atatattgtt ttttaaagta gttaattaag     240
ttggttaata ccataaagta agcacaaagc aatatgtgac aaataagtga taaataagta     300
atttgtctta cgggtatttg tgacaaataa gtttataagg ataactcaac catcttagac     360
aacctatcaa catcaacttg cctaaggtga atgttaatat tgattgttag gggtgagtgt     420
cacttgccat tgaagttgat tatcaaaggt gattttcatt gcagtttatc atataagcag     480
tagttggagt ctgaaattga aggtggttat cgaagttgat aatcaaaaag tgattttctc     540
aaagtttgta gtcatagctt ggaattcatc gtgtaaacgt ggtcatcaaa gttggctttt     600
tttggagttt cctattggag atagttacca tagcccaaaa ttagttgttg gaggtggtca     660
cataaaggta tctagtcgtt aggtcagttt gtcatcgaag gtggttgcca gaccttgaaa     720
tcgatcatca aagttggtta tctgagtgtg gtaatggtaa ttgatcgttg aatctattag     780
aaaaactgga gagagcttca tcaacctata agttagtgg accaaagaga actcaaactc     840
aacttatatt ttgatgtgtt aactccccta aaataaaaca aacgaaacaa aaaaaaaaa     900
tcataaagac aaaaatgaaa aatggagta ccatcattgt actaaaaaaa tatattttaa     960
caaagaaaa aatcaatgac tacaaataaa ttttaaaaca ctagatttaa aaaaaaaat    1020
caaagaacaa aaatagaaga tatttatata tatatatatt taaaaaagaa aattaataga    1080
tattataatg aggcttagta ttttcaaaat cctgttttag ggcaaaaaaa agaggggaaa    1140
aataaaacaa cttccgtctt tgattcacaa acaagagacg tgtcatgttc tcattagcta    1200
aaaccggaaa aaagcgatg agtaaaaaag tcataaaaac ggttaaccct caacgcctct    1260
caagggttct tcacgtgcca gtcacgtgga aggaagggaa gcgaaccggg tctaagaaaa    1320
ccgcactatc tggggtaagt actattagta taattgtact ataagcgcgg agttgagaaa    1380
gacgccggct ttttgaacga tttaatcggc gatctaaaga agaagcctct tggttccttc    1440
ttctcctctt cgcttctctg ttaaatgttc atcacaaata aatcccatac caatcgcccg    1500
acatttctct cactccacaa tcggagacca aagattattc cttttttccc atttctattt    1560
cttccaatct caatcgcatg acggattatc gtttgtcgac gatgaatctc tggactgacg    1620
agaacgcgtc ggttatggac gctttcatga attccgatct gtcttcctac tgggctccgt    1680
cagccgcctc ctctcactct cttccaccac caccgccacc tcagtcctcc gcctccacat    1740
ccactccccc gccggacgca cctaagtccc tccccgtttt caatcaggag actctgcagc    1800
agcggctcca ggcgctgatc gacggtgcta gggagagttg gacttatgcg attttctggc    1860
agtcgtctta tgattattct ggtgggtctg ttttggggtg gggtgatggg tattacaaag    1920
gagaggaaga taaggaaag ggaaaagcga aaatggtgtc gtcagcggcg agcaggctc    1980
accggaagaa ggttttacgg gagcttaact ctttgatttc tggctctgcc gccggacctg    2040
```

```
acgatgcggt ggatgaggag gttacggata cggagtggtt cttttttggtt tcgatgactc    2100
agtcgtttgt taatggtgtt gggttaccga gtcaagcgtt ttaccactcg acgccgattt    2160
gggtctctgg tgccgatcgg ctgtcggcgt ctgcctgtga acgagctaga caggggaggg    2220
tttttgggtt acagacgatg gtctgtattc catcgcctaa cggtgttgtg gaaatggggtt    2280
cgacggaatt gattcatcga acgtcggatt tgatgaataa ggtcaagatt ctgttcaatt    2340
tcaacaatct cgaaacgagt tcttggattt cgggaactac cgccgccgca tccgctgccg    2400
acgaagggga aaacgacccg tcgtcgatgt ggatcagtga gccatcgagt acaatcgaga    2460
tgaaggattc aatcaccacc actgttcctt ccagcaacgt tccggcaaag ccaatccgtt    2520
cggaaaatcc cagtacaagt agcttaacgg aaaatatgag cacgattcaa caatcccatc    2580
ataaacagag ccaaagcttc ttaaatttct ccgattacgg cttcgaatca atcccacaa    2640
agaacaccac cgctaccgcc accgcaacca ccagcaccac cccatcattc aagccggaat    2700
ccggcgggat gctgaatttc ggcaacggga gcctcttctc cggccattca cagtacgtaa    2760
caaacgaaca gaacgagaaa aagagatccc ctgcttctcg aagtagcaac gacgaaggga    2820
tcctctcttt cacctccggc gtgatcttac cctcttccgg taaggtaaaa tccggtgatt    2880
cagaccattc agatctcgaa gcatcagcga tcagagaagt ggatagctgt acaaaatcat    2940
tagaacccga aaaacgtcca agaaaaagag gtagaaaacc agcaaacgga agagaagagc    3000
cattgaatca cgtagaagca gagagacaac ggcgagagaa attaaaccag aaattctacg    3060
ctctccgagc tgtagttcca aacgtatcta agatggacaa agcctcacta ctaggtgacg    3120
cggtttcgta cataaacgag ctcaaatcga agctccaaat ggcagaatcg gagaaaacag    3180
atatgggaaa acatctagaa ttgctgaaga aggagatggg aggaaaagat ttaggatgtt    3240
actcaaaccc aaatgatgaa gatctgaaaa cagggaaaag aaaggtaatg gatatggaga    3300
ttgaagttaa aatcatgggt tgggatgcga tgataaggat tcaaagcaac aagaagaatc    3360
atccggcggc gaggttgatg acggcgttta aggatttgga tttagaaatg cttcacgcga    3420
gtgtttctgt agtgaatgat ttgatgattc aacaagcaac agtgaagatg gggagcagat    3480
tttacacaca agagcagctt aaaatggctc ttgtcgcccg agtcggcggt ggtggaagtg    3540
gaggcggcgg tggaatcatg taaatggggt tagggacat ttttgaagct cccaattagt    3600
agagtttagt tgagggaatc tgatttagta ttgtgtaata taaatgttgg taaattattt    3660
ttgataattc tcttgttgtt catcttttgt tgttagagta atttgggagt tcttctatat    3720
gtagttttg tttattaaat atgaaatcta atagaagtaa agatcaaaga ccttcaaact    3780
ttgtgtttga tcatttcaat tctccttctt tccttttttt tttttttttt tgtttttgtt    3840
tttgttttta gggttttgtt tgaactagta ggtctagttt agggaaaatc taggtttgat    3900
cggaaattaa ggactaacct taacctttct tggtacaaac tttagttaaa cctacatgtc    3960
aatagactta aaagatttag tattaaggtc caaactttcc cacggttgag atcgaaagcc    4020
cctgatataa gaacaactca taaaatttga catttgatta ggttattaag tggatttcaa    4080
tggggatcga gacctactct cttaggtcaa cattttttcat aaatacataa gttggttagt    4140
ctagatttgt aaatttttaat tgggtttagt tgtttatgta tggagatagg taattgaact    4200
tctcatattg agttatatac tcctacaagt aaagggagaa actcccaata gatattggtt    4260
gtgttggaaa ggttatgaat cgattaataa gtcaattacc attatcttga ttttgaacgc    4320
caatgcatca catgcatata tatatatata tattgtcggc tagtacacga ccaattaatg    4380
```

```
tttggataaa gttctttcca gaatcatcct attttcaaga ctcactaaaa tccttcagat    4440
atatggttcc acaattggtc ctatgtacaa cagtgtattg aactacttca acacgatgtt    4500
cgtacaacaa tacccacaac tcattttgc actccatagc aaaaaataat atattatgtt     4560
aaggacaacc ccttaggtaa attgcttga atgagttaat caatcattta ccttgtgga     4620 tctaacatta atcctctcat acctactaat tggtatgctt gagatgcatt ttctcgagca    4680
cctatagaag acgttatata tagactggat taaaagggac actcatccta aaattaggat    4740
tcatttcttg tagcaaatat tcacttgtag catacgatat ctaaagggac tggcgtaagt    4800
tttctactgc gggtacgttt ccataatgat ggtgtctttt caatatcaaa ctttactgtt    4860
caccatcttg aactagccat cctttagaga gtattgttaa aagatatcaa ttcctaatga    4920
aatggatgtc gcagtggccc actaaaagtc tttaattgat attacaatct ttatgctagt    4980
tgagctatgc tcgatttatc attttgtata caataagctc taacaagtta gttaggttcc    5040
atcctttata tatagtttgt acacattatt atttttagat gcatgccaca tgcctaaacc    5100
ttcaaatgat tggttactat attggagagt ttaagctacc tctcatacat agaaatgtta    5160
agtagattca atgaagttta gaattttaa ttttgaaaat                           5200

<210> SEQ ID NO 13
<211> LENGTH: 1986
<212> TYPE: DNA
<213> ORGANISM: Cucumis sativus

<400> SEQUENCE: 13
atgacggatt atcgtttgtc gacgatgaat ctctggactg acgagaacgc gtcggttatg      60
gacgctttca tgaattccga tctgtcttcc tactgggctc cgtcagccgc ctcctctcac     120
tctcttcacc acccaccgcc acctcagtcc tccgcctcca catccactcc ccgccggac     180 gcacctaagt ccctcccgt ttcaatcag agactctgc agcagcggct ccaggcgctg        240
atcgacggtg ctagggagag ttggactat gcgattttct ggcagtcgtc ttatgattat       300
tctggtgggt ctgttttggg gtggggtgat gggtattaca aaggagagga agataaagga      360
aagggaaaag cgaaaatggt gtcgtcagcg gcggagcagg ctcaccggaa gaaggtttta      420
cgggagctta actctttgat ttctggctct gccgccggac ctgacgatgc ggtggatgag      480
gaggttacgg atacggagtg gttcttttg gtttcgatga ctcagtcgtt tgttaatggt      540
gttgggttac cgagtcaagc gttttaccac tcgacgccga tttgggtctc tggtgccgat    600
cggctgtcgg cgtctgcctg tgaacgagct agacagggga gggttttgg gttacagacg    660 atggtctgta ttccatcgcc taacggtgtt gtggaaatgg gttcgacgga attgattcat    720
cgaacgtcgg atttgatgaa taaggtcaag attctgttca atttcaacaa tctcgaaacg    780
agttcttgga tttcgggaac taccgccgcc gcatccgctg ccgacgaagg ggaaaacgac    840
ccgtcgtcga tgtggatcag tgagccatcg agtacaatcg agatgaagga ttcaatcacc    900
accactgttc cttccagcaa cgttccggca aagccaatcc gttcggaaaa tcccagtaca    960
agtagcttaa cggaaaatat gagcacgatt caacaatccc atcataaaca gagccaaagc   1020
ttcttaaatt tctccgatta cggcttcgaa tcaaatccca caagaacac caccgctacc    1080 gccaccgcaa ccaccagcac caccccatca ttcaagccgg aatccggcgg gatgctgaat   1140
ttcggcaacg ggagcctctt ctccggccat tcacagtacg taacaaacga acagaacgag   1200
aaaaagagat cccctgcttc tcgaagtagc aacgacgaag ggatcctctc tttcacctcc   1260
ggcgtgatct taccctcttc cggtaaggta aaatccggtg attcagacca ttcagatctc    1320
```

-continued

```
gaagcatcag cgatcagaga agtggatagc tgtacaaaat cattagaacc cgaaaaacgt   1380
ccaagaaaaa gaggtagaaa accagcaaac ggaagagaag agccattgaa tcacgtagaa   1440
gcagagagac aacggcgaga gaaattaaac cagaaattct acgctctccg agctgtagtt   1500
ccaaacgtat ctaagatgga caaagcctca ctactaggtg acgcggtttc gtacataaac   1560
gagctcaaat cgaagctcca aatggcagaa tcggagaaaa cagatatggg aaaacatcta   1620
gaattgctga agaaggagat gggaggaaaa gatttaggt gttactcaaa cccaaatgat   1680
gaagatctga aaacagggaa agaaaggta atggatatgg agattgaagt taaaatcatg   1740
ggttgggatg cgatgataag gattcaaagc aacaagaaga atcatccggc ggcgaggttg   1800
atgacggcgt ttaaggattt ggatttagaa atgcttcacg cgagtgtttc tgtagtgaat   1860
gatttgatga ttcaacaagc aacagtgaag atggggagca gattttacac acaagagcag   1920
cttaaaatgg ctccttgtcgc ccgagtcggc ggtggtggaa gtggaggcgg cggtggaatc   1980
atgtaa                                                             1986
```

<210> SEQ ID NO 14
<211> LENGTH: 661
<212> TYPE: PRT
<213> ORGANISM: Cucumis sativus

<400> SEQUENCE: 14

```
Met Thr Asp Tyr Arg Leu Ser Thr Met Asn Leu Trp Thr Asp Glu Asn
1               5                   10                  15

Ala Ser Val Met Asp Ala Phe Met Asn Ser Asp Leu Ser Ser Tyr Trp
            20                  25                  30

Ala Pro Ser Ala Ala Ser Ser His Ser Leu His His Pro Pro Pro Pro
        35                  40                  45

Gln Ser Ser Ala Ser Thr Ser Thr Pro Pro Pro Asp Ala Pro Lys Ser
    50                  55                  60

Leu Pro Val Phe Asn Gln Glu Thr Leu Gln Gln Arg Leu Gln Ala Leu
65                  70                  75                  80

Ile Asp Gly Ala Arg Glu Ser Trp Thr Tyr Ala Ile Phe Trp Gln Ser
                85                  90                  95

Ser Tyr Asp Tyr Ser Gly Gly Ser Val Leu Gly Trp Gly Asp Gly Tyr
            100                 105                 110

Tyr Lys Gly Glu Glu Asp Lys Gly Lys Gly Lys Ala Lys Met Val Ser
        115                 120                 125

Ser Ala Ala Glu Gln Ala His Arg Lys Lys Val Leu Arg Glu Leu Asn
    130                 135                 140

Ser Leu Ile Ser Gly Ser Ala Ala Gly Pro Asp Asp Ala Val Asp Glu
145                 150                 155                 160

Glu Val Thr Asp Thr Glu Trp Phe Phe Leu Val Ser Met Thr Gln Ser
                165                 170                 175

Phe Val Asn Gly Val Gly Leu Pro Ser Gln Ala Phe Tyr His Ser Thr
            180                 185                 190

Pro Ile Trp Val Ser Gly Ala Asp Arg Leu Ser Ala Ser Ala Cys Glu
        195                 200                 205

Arg Ala Arg Gln Gly Arg Val Phe Gly Leu Gln Thr Met Val Cys Ile
    210                 215                 220

Pro Ser Pro Asn Gly Val Val Glu Met Gly Ser Thr Glu Leu Ile His
225                 230                 235                 240

Arg Thr Ser Asp Leu Met Asn Lys Val Lys Ile Leu Phe Asn Phe Asn
```

```
                    245                 250                 255
Asn Leu Glu Thr Ser Ser Trp Ile Ser Gly Thr Thr Ala Ala Ala Ser
                260                 265                 270

Ala Ala Asp Glu Gly Glu Asn Asp Pro Ser Ser Met Trp Ile Ser Glu
            275                 280                 285

Pro Ser Ser Thr Ile Glu Met Lys Asp Ser Ile Thr Thr Thr Val Pro
        290                 295                 300

Ser Ser Asn Val Pro Ala Lys Pro Ile Arg Ser Glu Asn Pro Ser Thr
305                 310                 315                 320

Ser Ser Leu Thr Glu Asn Met Ser Thr Ile Gln Gln Ser His His Lys
                325                 330                 335

Gln Ser Gln Ser Phe Leu Asn Phe Ser Asp Tyr Gly Phe Glu Ser Asn
            340                 345                 350

Pro Thr Lys Asn Thr Thr Ala Thr Ala Thr Ala Thr Thr Ser Thr Thr
        355                 360                 365

Pro Ser Phe Lys Pro Glu Ser Gly Gly Met Leu Asn Phe Gly Asn Gly
    370                 375                 380

Ser Leu Phe Ser Gly His Ser Gln Tyr Val Thr Asn Glu Gln Asn Glu
385                 390                 395                 400

Lys Lys Arg Ser Pro Ala Ser Arg Ser Ser Asn Asp Glu Gly Ile Leu
                405                 410                 415

Ser Phe Thr Ser Gly Val Ile Leu Pro Ser Ser Gly Lys Val Lys Ser
            420                 425                 430

Gly Asp Ser Asp His Ser Asp Leu Glu Ala Ser Ala Ile Arg Glu Val
        435                 440                 445

Asp Ser Cys Thr Lys Ser Leu Glu Pro Glu Lys Arg Pro Arg Lys Arg
    450                 455                 460

Gly Arg Lys Pro Ala Asn Gly Arg Glu Glu Pro Leu Asn His Val Glu
465                 470                 475                 480

Ala Glu Arg Gln Arg Arg Glu Lys Leu Asn Gln Lys Phe Tyr Ala Leu
                485                 490                 495

Arg Ala Val Val Pro Asn Val Ser Lys Met Asp Lys Ala Ser Leu Leu
            500                 505                 510

Gly Asp Ala Val Ser Tyr Ile Asn Glu Leu Lys Ser Lys Leu Gln Met
        515                 520                 525

Ala Glu Ser Glu Lys Thr Asp Met Gly Lys His Leu Glu Leu Leu Lys
    530                 535                 540

Lys Glu Met Gly Gly Lys Asp Leu Gly Cys Tyr Ser Asn Pro Asn Asp
545                 550                 555                 560

Glu Asp Leu Lys Thr Gly Lys Arg Lys Val Met Asp Met Glu Ile Glu
                565                 570                 575

Val Lys Ile Met Gly Trp Asp Ala Met Ile Arg Ile Gln Ser Asn Lys
            580                 585                 590

Lys Asn His Pro Ala Ala Arg Leu Met Thr Ala Phe Lys Asp Leu Asp
        595                 600                 605

Leu Glu Met Leu His Ala Ser Val Ser Val Asn Asp Leu Met Ile
    610                 615                 620

Gln Gln Ala Thr Val Lys Met Gly Ser Arg Phe Tyr Thr Gln Glu Gln
625                 630                 635                 640

Leu Lys Met Ala Leu Val Ala Arg Val Gly Gly Gly Ser Gly Gly
                645                 650                 655

Gly Gly Gly Ile Met
            660
```

<210> SEQ ID NO 15
<211> LENGTH: 6400
<212> TYPE: DNA
<213> ORGANISM: Cucumis melo
<220> FEATURE:
<221> NAME/KEY: misc_feature
<222> LOCATION: 5198..5369
<223> OTHER INFORMATION: /note="n = a or c or t or g"

<400> SEQUENCE: 15

| | | | | | | |
|---|---|---|---|---|---|---|
| ttcctgtcct | aaggttgcag | taattttaga | ttttactttg | agataaaaat | tgtaaaaatt | 60 |
| aaatgggttt | agtattacaa | taatcgattt | aactataaaa | ttcttaaata | ataaattaat | 120 |
| atattttaat | tatattatgt | aagttaggct | ttgtaagtta | tttattctct | tacattaatt | 180 |
| atagtatgtg | ttttttttata | tgatttgaat | ttcaattcat | tttattgtat | ttaaattatc | 240 |
| tgataaaagt | ttaggatttt | ttaataaaat | taaatcaatt | actatagaag | attaaaaata | 300 |
| ttttaattta | aaaatgagtt | attttgaaaa | agaaataaa | ggatatatat | atatacatat | 360 |
| tgaaataagt | gagagtatta | ctttattttg | agtaaagtgg | gaaaataaat | ttttgcgtag | 420 |
| aaaatttgct | aactttcaaa | aaagcatttg | tcgtcttttc | tctttcttct | attttttgtaa | 480 |
| ttttgttgtt | tttttccct | ctcattcctt | aatcatttta | ttgcaatgtt | tttcccttaa | 540 |
| aaagaagcat | agctcaattt | tttaaatatt | ttgataatgt | gtagaattga | ataatcaaat | 600 |
| ctctaatatt | catgctaacc | attttaacta | tttttttgata | gggttgaaag | tatgttaggt | 660 |
| ttttatgagt | atttactata | tattaacaat | tgggctcaat | ttttataaat | ttgtaatttg | 720 |
| atggtttgag | ttttaaaagg | aaagaaatgg | ttggaatgtt | aataatcaat | atggtttaga | 780 |
| ttaaagtaat | cgatttcaca | aaagttggag | ttgagctagg | gatatgacat | gcattcaacc | 840 |
| cacctaggct | tgaggggaga | cgagagtttg | gaccaaatgt | ccaaatatga | accgatcaat | 900 |
| ttttaccttg | gtcgagacat | acccacactt | ttgattaaat | aggcatgtta | aacgtgtagg | 960 |
| acaacatatt | gagtttgaga | aaaagcctaa | tctaactcca | aaaccctaat | ttaaatgtct | 1020 |
| taggtcataa | gtaagttaac | tatatcatcc | aaactcttgc | gagttgcgac | aacttaaaga | 1080 |
| gtttaattag | ttacaatcat | tattgtaatt | ttttttaaatt | tgaggcatca | tatgttgtta | 1140 |
| ctcgatgagg | ctgtttaggg | cgttgagttg | atgtagggtg | ttgttaagaa | gcaaagtaat | 1200 |
| atgtcttatg | gatacttgtg | acaaataagt | ttataaggat | gatccaacca | atcttagaca | 1260 |
| acttctcaac | atcaaattgc | cttaggtgaa | tgttagtata | tattgattgt | tagaggtagt | 1320 |
| tgtcactatt | tgtcattgaa | gttgattatc | aaaggtgatt | ctcgttgaag | tttatcatag | 1380 |
| aggtgggttg | ttggagccca | aagttaaagg | tggttttcga | agttgataat | caaaggcgat | 1440 |
| tttcgctaaa | gtttgtagtc | atagcttgga | attcatcgca | tggacgtagt | catcaaagtt | 1500 |
| ggctttcgtt | ggatttgtta | tcagagatga | ttacaggctc | gaaattagtg | gttggaggtg | 1560 |
| gtcgtgcaaa | ggtaatctag | ttgtcatagt | ttttcatcga | aggtggttgt | aggaccctga | 1620 |
| aatcgattgt | caagttgga | ggtgtgaaag | tggctgttgt | cggagtcgga | tcctagagtt | 1680 |
| tggtaatggg | taattgtcat | aatggtaatc | gatcgtcgaa | tccattgaaa | acattggaaa | 1740 |
| gaactccacc | aacatgtaaa | gttggtaggc | caaacgaaac | tcaaacccat | cttatattga | 1800 |
| tgtgcaaaac | atctctagga | taaacaaac | caaactaata | aatcataaag | acaaaaatga | 1860 |
| aaatgagag | taccaaaaaa | aaaaaaaaaa | gagcaataac | ttcaaataag | ttttaaaaca | 1920 |
| ctagatttaa | aaaaaaaatc | aaagaacaaa | aatagaagat | attttaatct | ctacaaaaaa | 1980 |

```
aaaaaaaaag aaaaaaagaa aattatagat attaataatt gtaatgaggc ttagtatttt    2040
caaaatcctc atttagagga aaaaaaaagg gagaaaataa actaacttcc gtctttgttt    2100
cacaaacaag acacgcgtca tattctcatt agctaaaacc gcaaaaaaag caatcagtca    2160
aaaagtctta aaaacggtta acactctaaa cgcctctcaa gaattcttca cgtgtcagtc    2220
acatggaaaa gaaaccggcc gaaccgggtc gaagtaaacc gcgttatctg gcgaagtaca    2280
aagtataata gtactataac cgcggagttg aaaaagacgc cggctttttg aacgattaaa    2340
tcggcgatct aaagaagaag gctcttggtt ccttcttcct ctgtgttcgc tcctttctta    2400
aatgttcatc acaaataaat cccaatccaa tcgcccgaca tttctctcac tccacaatcg    2460
gagacagaag attattcctt ttttccgatt tctgtttctt ccaatctcaa tcgcatgacg    2520
gattatcgtt tgtcgacgat gaatctctgg actgacgaga acgcgtcggt gatggacgct    2580
ttcatgaatt ccgatctctc ttcctactgg gctccatcag ccgcctcctc tcactctctt    2640
caccatccac caccacctca gtcctccgcc tcaacgtcca ctccccgcc ggacccacct    2700 aagtccctcc ccgttttcaa tcaggagact ctgcagcagc ggctccaggc gctgattgac    2760
ggtgctaggg agagttggac ttatgcgatt ttctggcagt catcttatga ttattccggt    2820
gggtctgttt tggggtgggg tgatgggtat tacaaaggag aggaagataa aggaaagggg    2880
aaagcgaaaa tggtgtcgtc agcggcagag caggctcacc ggaagaaggt tttacgggag    2940
cttaactctt tgatttctgg ctctgccgct ggaccggacg atgcggtgga tgaggaggtt    3000
acggatacag agtggttctt tttggtttcg atgactcagt cgtttgttaa tggtgttggg    3060
ttaccgagtc aggcgtttta ccactcgacg ccgatttggg tctctggtgc cgatcggctg    3120
tcggcgtctg cctgtgaacg agctagacag gggagggttt ttgggttaca gacgatggtc    3180
tgtattccat cgcctaacgg tgttgtggaa atgggttcga cggaattgat tcatcgaaca    3240
tcggatttga tgaataaggt caaaattctg ttcaatttca acaatctcga gacgagttct    3300
tggatttcgg gaactaccgc cgccgcatcc gctgcagacg aaggggaaaa cgacccgtcg    3360
tcgatgtgga tcagtgagcc atctagtaca atcgagatga aggattcaat taccaccacc    3420
gtcccttcca gcaacgttcc ggcaaagcca atccgatccg aaaatcccag ttcaagtagc    3480
ttaacggaaa atatgagcac gattcaacaa tcccatcata aacagagcca aagcttctta    3540
aatttctccg attacggctt cgagtcaaat ccctcaaaga acaccaccgc caccgccacc    3600
gtaaccacca gcaccactcc atcattcaag ccggaatccg gcgggatgct gaattttgga    3660
aacggaagcc tcttctccgg ccattcacag tacgtaacaa acgaacagaa cgaagaaaag    3720
agatcccctg cttctcgaag tagcaacgac gaagggatcc tctcttttcac ctccggcgtg    3780 atcttaccct cttccggtaa ggtaaaatca ggcgattcgg accactcaga tctcgaagca    3840
tcagtgatca gagaagtaga tagctgtaca aaatcattag aacccgaaaa acgtccaaga    3900
aaaagaggta gaaaccagc aaacggaaga gaagagccat tgaatcacgt agaagcagag    3960
agacaacggc gagagaaatt aaaccagaaa ttctacgctc tacgagctgt agttccaaac    4020
gtatctaaaa tggacaaagc ctcactactc ggtgacgccg tttcgtacat aaacgagctg    4080
aaatcgaagc tccaaatggc agaatcggag aaaacagata tgggaaaaca tctagaattg    4140
ctgaagaagg agatgggagg gaaagatgta ggatgttaca caaacccaaa tgatgaagat    4200
ctgaaaatag ggaaaagaaa ggtaatggat atggagattg aagttaaaat catgggttgg    4260
gatgcgatga tcagaattca aagcaacaag aagaatcatc cggcggcgag gttgatgacg    4320
gcgtttaagg atttggattt agaaatgctt cacgccagtg tttctgtagt gaatgatttg    4380
```

```
atgattcaac aagcaacagt gaagatgggg agcagatttt acacacaaga gcagcttaaa      4440
atggctcttg tggcccgagt cggtggtggt ggtggaggcg gaagcggcgg tggaatgatg      4500
taaatggggt tagggacat ttttgaagct cccaagtagt agagattagt tgagggaata       4560
taaatctgat ttagtattgt gtaatattaa tgttggtaaa ttattttga taattttgtt       4620
gttcatcttt tgttgttaga gtaatttggg agttcttctt ctatatatat gtagttttg       4680
ttgattaaat atcaaatcta atagaagtga agatcaaaga ccttcaaact ttgtgtttga      4740
tgatttcagt tctctttcct ttgttttag gttttgttt gaagtaaaaa tctaggtttg        4800
attggaaatt taggactaac cttaacctcc cagctcagta caaaccttag ttaaacctaa      4860
atgtcaatgg acctaagatt tggtattggg tccacatttc gtgtggttga gatagaaaac     4920
cccaactttc atataagaac aacccatata aaattcgtca tttgattagg ttattcgata     4980
agtggatttc aaaagggatc gggagaataa ctagtctctt aagtcaacat ttttcatata     5040
tacataagtt ggtcgatcta gatttctaaa ttttaagttg ggtttagttg tttttgtaca     5100
ataggaacg tgcgtgtgcg tgtgcgcgtg cgtgtgtgtg tggttgtgtg tgtgtgtgtg      5160
tcgctagttg tgtgtgtgtg tgtggttcgc taatacannn nnnnnnnnn nnnnnnnnn        5220
nnnnnnnnnn nnnnnnnnnn nnnnnnnnnn nnnnnnnnnn nnnnnnnnnn nnnnnnnnnn     5280
nnnnnnnnnn nnnnnnnnnn nnnnnnnnnn nnnnnnnnnn nnnnnnnnnn nnnnnnnnnn     5340
nnnnnnnnnn nnnnnnnnnn nnnnnnnnnt caatggactg acgtatttat ttactaggtc     5400
ataatgatgg tgttttcca aaatcaaact ttgctgttca atatcttaga ctagccatcc      5460
tttagaggag attgttaaaa atcatcaat tactaataaa aaaagacta ttgcagtggc       5520
ccactggaag tctttagttg atactacaat ctttatgcta gttaagctac gctcaatttg     5580
tccgtttgta tacaatgaac tctagcaaat tagcttacat catttataca tactttaaat     5640
gattggttac tgtctatcgg ggagagttta acctagctct tatacataga aattttaagc     5700
aggtttaacg aaagttgaag tttagaaaat ttaattttga aaataatcat ataaacatgc     5760
atgtcacaca tgtttattga tatgctaagt caatgagcta tagagagtta ggttcatagc     5820
cacataaata aaacctataa ctcttagttt tatgttttcg aaatttatgg ccgtttctta     5880
ctatttaaac ttttctaaaa gaaaaaattt gaactcatta aattctaaca acaaaaacat     5940
gttttgaaa acgaaataaa aatagataat aaaacacaaa aaacttatag atgaaaatag      6000
tgtttataag gttacttaaa aaaaaccaa acaatcatca aatacgaagt ttttgaaatt      6060
tgatttagat ttattcgatg tgtggttaat aattgggatg tagaaagata agctatggat     6120
gatagtgaag aattgaaggt gaccttacac ttcatatatg gacataaaaa aggaccattt     6180
tcatagaatc ttcaagaaga tattgatgga gataattttc tctcttttg tgaccccttc      6240
ttcatataaa gtaattccat tgttgaagtt aaatggtaaa aagaaaaaa aaaaagaac       6300
tttttattat tgtataaaac aatgatttag atttgaatt tatttgtga caatttggtc       6360
atttttgaata tctaaactac gttggttatt ttatcgtcac                          6400
```

<210> SEQ ID NO 16
<211> LENGTH: 1989
<212> TYPE: DNA
<213> ORGANISM: Cucumis melo

<400> SEQUENCE: 16

```
atgacggatt atcgtttgtc gacgatgaat ctctggactg acgagaacgc gtcggtgatg       60
```

```
gacgctttca tgaattccga tctctcttcc tactgggctc catcagccgc ctcctctcac    120
tctcttcacc atccaccacc acctcagtcc tccgcctcaa cgtccactcc ccgccggac    180
ccacctaagt ccctccccgt tttcaatcag gagactctgc agcagcggct ccaggcgctg    240
attgacggtg ctagggagag ttggacttat gcgattttct ggcagtcatc ttatgattat    300
tccggtgggt ctgttttggg gtggggtgat gggtattaca aaggagagga agataaagga    360
aaggggaaag cgaaaatggt gtcgtcagcg gcagagcagg ctcaccggaa gaaggtttta    420
cgggagctta actctttgat ttctggctct gccgctggac cggacgatgc ggtggatgag    480
gaggttacgg atacagagtg gttcttttg gtttcgatga ctcagtcgtt tgttaatggt    540
gttgggttac cgagtcaggc gttttaccac tcgacgccga tttgggtctc tggtgccgat    600
cggctgtcgg cgtctgcctg tgaacgagct agacagggga gggttttttgg gttacagacg    660
atggtctgta ttccatcgcc taacggtgtt gtggaaatgg gttcgacgga attgattcat    720
cgaacatcgg atttgatgaa taaggtcaaa attctgttca atttcaacaa tctcgagacg    780
agttcttgga tttcgggaac taccgccgcc gcatccgctg cagacgaagg ggaaaacgac    840
ccgtcgtcga tgtggatcag tgagccatct agtacaatcg agatgaagga ttcaattacc    900
accaccgtcc cttccagcaa cgttccggca aagccaatcc gatccgaaaa tcccagttca    960
agtagcttaa cggaaaatat gagcacgatt caacaatccc atcataaaca gagccaaagc   1020
ttcttaaatt tctccgatta cggcttcgag tcaaatccct caaagaacac caccgccacc   1080
gccaccgtaa ccaccagcac cactccatca ttcaagccgg aatccggcgg gatgctgaat   1140
tttgaaaacg gaagcctctt ctccggccat tcacagtacg taacaaacga acagaacgaa   1200
gaaaagagat cccctgcttc tcgaagtagc aacgacgaag ggatcctctc tttcacctcc   1260
ggcgtgatct taccctcttc cggtaaggta aaatcaggcg attcggacca ctcagatctc   1320
gaagcatcag tgatcagaga agtagatagc tgtacaaaat cattagaacc gaaaaacgt    1380
ccaagaaaaa gaggtagaaa accagcaaac ggaagagaag agccattgaa tcacgtagaa   1440
gcagagagac aacggcgaga gaaattaaac cagaaattct acgctctacg agctgtagtt   1500
ccaaacgtat ctaaaatgga caaagcctca ctactcggtg acgccgtttc gtacataaac   1560
gagctgaaat cgaagctcca aatggcagaa tcggagaaaa cagatatggg aaaacatcta   1620
gaattgctga gaaggagat gggagggaaa gatgtaggat gttacacaaa cccaaatgat   1680
gaagatctga aaatagggaa aagaaaggta atggatatgg agattgaagt taaaatcatg   1740
ggttgggatg cgatgatcag aattcaaagc aacaagaaga atcatccggc ggcgaggttg   1800
atgacggcgt ttaaggattt ggatttagaa atgcttcacg ccagtgtttc tgtagtgaat   1860
gatttgatga ttcaacaagc aacagtgaag atggggagca gattttacac acaagagcag   1920
cttaaaatgg ctcttgtggc ccgagtcggt ggtggtggtg gaggcggaag cggcggtgga   1980
atgatgtaa                                                           1989
```

<210> SEQ ID NO 17
<211> LENGTH: 662
<212> TYPE: PRT
<213> ORGANISM: Cucumis melo

<400> SEQUENCE: 17

Met Thr Asp Tyr Arg Leu Ser Thr Met Asn Leu Trp Thr Asp Glu Asn
1               5                   10                  15

Ala Ser Val Met Asp Ala Phe Met Asn Ser Asp Leu Ser Ser Tyr Trp
            20                  25                  30

```
Ala Pro Ser Ala Ala Ser Ser His Ser Leu His His Pro Pro Pro
            35                  40                  45

Gln Ser Ser Ala Ser Thr Ser Thr Pro Pro Asp Pro Pro Lys Ser
 50                  55                  60

Leu Pro Val Phe Asn Gln Glu Thr Leu Gln Gln Arg Leu Gln Ala Leu
 65                  70                  75                  80

Ile Asp Gly Ala Arg Glu Ser Trp Thr Tyr Ala Ile Phe Trp Gln Ser
                 85                  90                  95

Ser Tyr Asp Tyr Ser Gly Gly Ser Val Leu Gly Trp Gly Asp Gly Tyr
                100                 105                 110

Tyr Lys Gly Glu Glu Asp Lys Gly Lys Gly Lys Ala Lys Met Val Ser
                115                 120                 125

Ser Ala Ala Glu Gln Ala His Arg Lys Lys Val Leu Arg Glu Leu Asn
130                 135                 140

Ser Leu Ile Ser Gly Ser Ala Ala Gly Pro Asp Asp Ala Val Asp Glu
145                 150                 155                 160

Glu Val Thr Asp Thr Glu Trp Phe Phe Leu Val Ser Met Thr Gln Ser
                165                 170                 175

Phe Val Asn Gly Val Gly Leu Pro Ser Gln Ala Phe Tyr His Ser Thr
                180                 185                 190

Pro Ile Trp Val Ser Gly Ala Asp Arg Leu Ser Ala Ser Ala Cys Glu
                195                 200                 205

Arg Ala Arg Gln Gly Arg Val Phe Gly Leu Gln Thr Met Val Cys Ile
                210                 215                 220

Pro Ser Pro Asn Gly Val Val Glu Met Gly Ser Thr Glu Leu Ile His
225                 230                 235                 240

Arg Thr Ser Asp Leu Met Asn Lys Val Lys Ile Leu Phe Asn Phe Asn
                245                 250                 255

Asn Leu Glu Thr Ser Ser Trp Ile Ser Gly Thr Thr Ala Ala Ala Ser
                260                 265                 270

Ala Ala Asp Glu Gly Glu Asn Asp Pro Ser Ser Met Trp Ile Ser Glu
                275                 280                 285

Pro Ser Ser Thr Ile Glu Met Lys Asp Ser Ile Thr Thr Thr Val Pro
                290                 295                 300

Ser Ser Asn Val Pro Ala Lys Pro Ile Arg Ser Glu Asn Pro Ser Ser
305                 310                 315                 320

Ser Ser Leu Thr Glu Asn Met Ser Thr Ile Gln Gln Ser His His Lys
                325                 330                 335

Gln Ser Gln Ser Phe Leu Asn Phe Ser Asp Tyr Gly Phe Glu Ser Asn
                340                 345                 350

Pro Ser Lys Asn Thr Thr Ala Thr Ala Thr Val Thr Thr Ser Thr Thr
                355                 360                 365

Pro Ser Phe Lys Pro Glu Ser Gly Gly Met Leu Asn Phe Gly Asn Gly
                370                 375                 380

Ser Leu Phe Ser Gly His Ser Gln Tyr Val Thr Asn Glu Gln Asn Glu
385                 390                 395                 400

Glu Lys Arg Ser Pro Ala Ser Arg Ser Ser Asn Asp Glu Gly Ile Leu
                405                 410                 415

Ser Phe Thr Ser Gly Val Ile Leu Pro Ser Ser Gly Lys Val Lys Ser
                420                 425                 430

Gly Asp Ser Asp His Ser Asp Leu Glu Ala Ser Val Ile Arg Glu Val
                435                 440                 445
```

```
Asp Ser Cys Thr Lys Ser Leu Glu Pro Glu Lys Arg Pro Arg Lys Arg
    450                 455                 460

Gly Arg Lys Pro Ala Asn Gly Arg Glu Glu Pro Leu Asn His Val Glu
465                 470                 475                 480

Ala Glu Arg Gln Arg Arg Glu Lys Leu Asn Gln Lys Phe Tyr Ala Leu
                485                 490                 495

Arg Ala Val Val Pro Asn Val Ser Lys Met Asp Lys Ala Ser Leu Leu
            500                 505                 510

Gly Asp Ala Val Ser Tyr Ile Asn Glu Leu Lys Ser Lys Leu Gln Met
        515                 520                 525

Ala Glu Ser Glu Lys Thr Asp Met Gly Lys His Leu Glu Leu Leu Lys
530                 535                 540

Lys Glu Met Gly Gly Lys Asp Val Gly Cys Tyr Thr Asn Pro Asn Asp
545                 550                 555                 560

Glu Asp Leu Lys Ile Gly Lys Arg Lys Val Met Asp Met Glu Ile Glu
                565                 570                 575

Val Lys Ile Met Gly Trp Asp Ala Met Ile Arg Ile Gln Ser Asn Lys
            580                 585                 590

Lys Asn His Pro Ala Ala Arg Leu Met Thr Ala Phe Lys Asp Leu Asp
        595                 600                 605

Leu Glu Met Leu His Ala Ser Val Ser Val Val Asn Asp Leu Met Ile
610                 615                 620

Gln Gln Ala Thr Val Lys Met Gly Ser Arg Phe Tyr Thr Gln Glu Gln
625                 630                 635                 640

Leu Lys Met Ala Leu Val Ala Arg Val Gly Gly Gly Gly Gly Gly Gly
                645                 650                 655

Ser Gly Gly Gly Met Met
            660
```

<210> SEQ ID NO 18
<211> LENGTH: 6400
<212> TYPE: DNA
<213> ORGANISM: Citrullus lanatus

<400> SEQUENCE: 18

```
ttttatataa atactaaatt gttataaatt aaactacgtt attactttgt ttttatttca    60
tctgcaaaca ttcaaaattg aaatccttct agtcacaagt taaaaaaatt gggagactat   120
accaggtgta cagtgaaagg aaaattacaa ggagtaaaaa aattaatatt gaatttata    180
aactatctta acatttatt ttttattttt tattttgcca actacaacaa ataagagaaa    240
ttatgttaaa ttgcaaaact gctaaaaata tttaaaatca atagcaaaat acaccgtcta   300
catgcgaatg tgggatcaaa tctcccctgt ttgaagtgaa aaaagttaaa ggagcatttg   360
actaaattaa caaagaaatt tttgttttca accaaaacaa atgttactct gttactttgt   420
tttgagtgaa ttgtgaaagt aagctaatgt gtagaaaatg tgataacttt caaaaaagca   480
ttcgtcgcct tttatatttc tacaatattg tttcgtttca tttttatttt tattttttca   540
tccctccctt ccttaatata actattgcaa atttcttaaa tgagtttaac aacctttcaa   600
tgcaagtttt tttctttttt tttttttta caatctgtga agttgaaaaa attgatacta   660
tcaccttata ttggcagtat taaccttatg ccatatgagt tatatttatt ttgataaata   720
cttacaatat gttaatgatt aagttcaatt tttatgtagt gtaaatttaa attttttaaat   780
ttaattaat gaatattctg cttcctgaaa caacatgttg gtcccacggg tggtatcagg    840
tggaggttgt ctttggattg acaagcattg gaagatttaa aagctcttcg ttttccattc   900
```

```
gggattgtca ttctgtcact tttggtggaa tctgattatg ttgaagtgat cacgtccctt    960
tgcaagattg atagtgatct ttcgaatatt acatttgttt tttgttgtgt tttaaagcta   1020
gatgaagaat ttgggaacat ccatttttgct aagtgttcga ggtttagtaa ttatttggct   1080
gcacactcgc tagctagatt ggttgtgtct ccttttttga attctttttt aggctcgaat   1140
ttgacttcct cctccttgga aaggttttaa ttttagttca tggggttcta atgtccctaa   1200
gttgttagtt gctgttattg gtgaggttga ttgtcagttg gggaaaaaaa attttaatag   1260
tttagaccta gttttacacc tcatttggta actatttggt tttttttgaat gattttgctg   1320
gttgagagag ataagtgaaa tttttatata tttgtaaata gttgatatt tttttcattt   1380
ataataattt ctcttcaaaa ttcaatcaaa tttttaaagt ataaattaaa agaaagggat   1440
cataacaaat cactcatcca tttgaaatac aaaaataaat tttgcactat atatatataa   1500
actcaacatc tcttataaga taaagcaaaa taactaaata aaataaattg ttttcaaata   1560
taagaaaatg aacaaaaaca tttataacta caatcaaatt ttactgtcta tttgcgatag   1620
atctcgatct attgtagata gattgtaata tttttgttatt tttttaaata tattctgcaa   1680
ctttatcatt taaaataatt tttcaaataa aaatttagaa acaaaattgt tgattgcaag   1740
taagtacata gactaaaaat atttgttaac aaaaaaaaaa aaaaaaaaac aatcaaagac   1800
tttaaataat tttaaaata aaaattgcag agagattaga aaaaaaatca agaacagaa   1860
atggtagata tttttagctt tttttaaaaa aagaaaaata atagatattt taatatggcg   1920
tagtattttc aaaagcgatt tatttggagc aaaaaaagga aagaataaaa ccacttcagt   1980
ctttgattaa caaatcagac acgtgtcaac ctctcattag tggaaaatgc aaacaaaccg   2040
atcagtcaaa agtcttaaaa acggttaccc cccaaagctc acaaacgaaa cgcccccgat   2100
gatccttcac gtgcccgtca cgtggaaaga aacgaaccga accgggtcta aatgagccgc   2160
actctctggc aggagtacta gtatagtact acaagcgcgg agttgaaaac gacgccggct   2220
ttttgaacga ttaaatcggc gatccaaaga agaagcctct tggttccttc ttccctgtt   2280
cgctcctctg taaatgttca tcacaaataa atcccaatcc aatcgcccga catttctctc   2340
actccacaat tggagaccca gaattattct ctttttccca ttctgtttct tctcgaatcc   2400
caatcgcatg acggattatc gtttgtcgac gatgaatctc tggactgacg aaaacgcgtc   2460
ggtgatggac gctttcatga actccgatct gtcctcttac tgggctccat ctgccgcctc   2520
ctctcactct cttcaccacc caccgccgcc tcagtcctcc gcctccacct ccactccccc   2580
accggacccg cccaagtccc tgcctgtttt caatcaggag actctgcagc agcggctcca   2640
ggcgctgatc gatggcgcta gggagagttg gacttacgcg attttctggc agtcgtccta   2700
tgattattcc ggtgcgtcgg ttttagggtg gggagatggg tattacaaag gggaggagga   2760
taaagggaag ggaaaagcga aaatggtgtc gtcggcggca gagcaggctc atcggaagaa   2820
ggttttacgg gagcttaact cttaatttc tggctccgct gccggaccgg acgatgcgt   2880
ggatgaggag gttacggata cggagtggtt cttttttggtt tcgatgactc agtcttttga   2940
taatggagtt tggttaccga gtcaggcgtt ttacaactcg acgccgattt gggtttctgg   3000
cgccgatcgg ctgtcggcgt ctgcctgtga acgggccaga caggggaggg ttttggggtt   3060
acagacgatg gtctgtattc catcgccaaa cggagttgtg gaaatgggtt cgacggaatt   3120
gattcatcga acgtcggatt tgatgaacaa ggtcaagatt ctgttcaatt tcaacaatct   3180
cgaaacgagt tcttggatat cgggaaccac cgccgccgat gaaggggaaa acgacccgtc   3240
```

```
gtcgatgtgg atcagtgagc cgtcgagtac tatcgagatg aaggattcca ttaccaccac    3300
cgtcccttcc ggcaacgtcc cggcaaagcc aatccattcg gaaaatccca gttccagcag    3360
cttaacggaa aatatcagcg cgatccaaca accatcccat caaaaacaaa gccaaagctt    3420
cttaaatttc tccgattacg gcttcgaatc aaatccctca aagaacacca ccgcggccgc    3480
aacaaccacc accgccaccc catcattcaa gccggaatcc ggcgggatgc tgaatttcgg    3540
caacggaaac ctcttctcta gccattcaca gtatgtaaca aacgaacaga acgagaaaaa    3600
gagatcccct gcttctcgga gtagcaacga cgaagggatc ctctctttca cctctggcgt    3660
gatcttaccc tcctccggta aggtaaaatc cggggactca gaccactcag atctcgaagc    3720
atcggtgatc agagaagtgg atagctgtac aaaatcatta gaacccgaaa acgtccaag    3780 aaaaagaggt agaaaaccag caaacggaag agaagagcca ttgaatcatg tagaagcaga    3840
gagacaacgg cgagagaagt tgaaccagaa attctacgct ctccgagctg tagttccaaa    3900
cgtatctaaa atggacaagg cctcactact gggagacgcg gtttcttaca tcaacgagct    3960
caaatcaaag ctccaaatag cggaaacgga gaaacagaga tgggaaaac atttagaatt    4020 gctgaagaag gagatgggag ggaaagattt cgggaattac ccgaacccaa atgatgaaga    4080
tctgaaaata gggaaagaa aggtaatgga tatggagatc gaagttaaaa tcatgggttg    4140
ggatgcgatg ataaggattc aaagcagcaa gaaaaatcat ccggcggcaa ggctgatggc    4200
ggcgtttaag gatttagatt tagaaatgct tcatgcgagt gtttctgtag tgaatgattt    4260
gatgattcaa caggcaacgg tgaagatggg gagcagattt tacacacagg agcagcttaa    4320
aatggctctc gtcgcccgag tcgggggcgg cggcggcagc agccatggaa tgatgtaaat    4380
gggttgtgta attacaagtg ggagggggaca ttttgaggg ctcccaagta gagattagct    4440
gagggaatct gattagtatg tgtaagataa aatgttggta aattattttg atcattttgt    4500
tgttgtttca tctttttttg gttgttagag taatttggga agttctttgt gtagttttg    4560 ttaaatatca aatctaatag aacagaagat gaaagacctt caaactttgt gatgggttgc    4620
tgtcttcaaa aatacccatt gcgtttctct cttttttggt agaagtttag tcggtaggta    4680
cttcttccac taaaccttaa cctcacatag tatccacacg agttaagtct agagttctca    4740
atagccatga gttgggccca aaggccgaga agcccaactt tcgtatctca aatcagatta    4800
ggtttaagac ttaagtcatc ctcaatttgt ctgtttgtat aataatatct atctattatg    4860
cttattaatg agctattata aggtaaggta ggttacatca tttatattta tagttagata    4920
atcactcaaa gttaatttta gatgcatgcc gcacgtctaa acttgcaaat gattggttac    4980
catatttggg aggagttcat aaaaatgtta aagtgaaaat atcatataca acatgttgat    5040
gccacatgtt tgtttcatat gctaattcag tgtgagctat ggtcagtttg gttgagagtt    5100
acactttata aaaactattt ttttaaggca gtgtcttata acaaatttca ttttaatt    5160 tatgattttt caaattttg aaatttattt ccttctaatt ctaatttttc tattatggtg    5220
ttcacatgtc tacatgaaac tcttgaattc cttgtcaaat tctaataaca aaaacatgtt    5280
tttggaaact acatatttta gttttttttc tttaacaaaa catggaaact taggatgaaa    5340
gtagtgttta taaggttatt tttcaaaaac aaaatatcaa atgattatca aatgagacct    5400
taattcttaa aatttggcta cgattttgaa atattattaa aaagtatata acaaaacaaa    5460
aacaaagaat gtcacgagta aattttgttt ctataaattt aaattaaaaa aaatttaaaa    5520
atagagatca aataatcata aaaaagagcc tatgtgtgat tggcatgtaa aaagataagg    5580
tttttgagcc attgatgata gtggaagctt gtgaagaatt aaagatgacc ttacacttca    5640
```

```
tgtatggaca taaaatgtca tcttcataga atattcaaga agattttgat aaatataatt    5700
tttcactctt tgtgacttct ataaagtagt tcaattgttg aagtaaaatg gcaaaaaatg    5760
gttttatgaa ctttcataaa attgataatc ctcaccccaa ttccatttgt ttgttttttag   5820 ttttttaaaa ttaaacctat ttttttctatt tcttgtaatg atttacatct ttcttaggtg   5880
taatcgttga attcgtagtc aaattctaaa atgaaaaact aattttttta gttttcaaaa    5940
tttggcttga cttttaaacc attggtaaaa aattagata caaaggcaa aaatttggaa      6000 ttggaagtag tctctataaa cttaattttc aaaacaaaa aaaagaccaa aaaccaaatg     6060
gttaccaaac gggatagtaa ttttttgaatt gatttgtaca atttagttct tcttttgtaa   6120
taattaagtg tgtcaattct taatacgtaa taactaactt aatatttgta gctaataaaa    6180
taatattttt tgtctttaat tagtttataa gatgtgactg taagaaattc tattaaatgt    6240
ttttttttca ccatagaagt taaattgtta aataattgaa agtttatgga ttaaacttta    6300
cataattgtt taaaaattaa attattacaa aactagaaaa tttagaggtt aaaagtgttt    6360
tttttttttt tttttttttaa cttaaaaggt tttatttgga                         6400
```

<210> SEQ ID NO 19
<211> LENGTH: 1971
<212> TYPE: DNA
<213> ORGANISM: Citrullus lanatus

<400> SEQUENCE: 19

```
atgacggatt atcgtttgtc gacgatgaat ctctggactg acgaaaacgc gtcggtgatg      60
gacgctttca tgaactccga tctgtcctct tactgggctc catctgccgc ctcctctcac     120
tctcttcacc acccaccgcc gcctcagtcc tccgcctcca cctccactcc cccaccggac     180
ccgcccaagt ccctgcctgt tttcaatcag gagactctgc agcagcggct ccaggcgctg     240
atcgatggcg ctagggagag ttggacttac gcgattttct ggcagtcgtc ctatgattat     300
tccggtgcgt cggttttagg gtggggagat gggtattaca aaggggagga ggataaaggg     360
aagggaaaag cgaaaatggt gtcgtcggcg gcagagcagg ctcatcggaa gaaggtttta     420
cgggagctta actcttttaat ttctggctcc gctgccggac cggacgatgc ggtggatgag    480
gaggttacgg atacggagtg gttcttttttg gtttcgatga ctcagtcttt tgataatgga   540
gtttggttac cgagtcaggc gttttacaac tcgacgccga tttgggtttc tggcgccgat    600
cggctgtcgg cgtctgcctg tgaacgggcc agacagggga gggtttttgg gttacagacg    660
atggtctgta ttccatcgcc aaacggagtt gtggaaatgg gttcgacgga attgattcat    720
cgaacgtcgg atttgatgaa caaggtcaag attctgttca atttcaacaa tctcgaaacg    780
agttcttgga tatcgggaac caccgccgcc gatgaagggg aaaacgaccc gtcgtcgatg    840
tggatcagtg agccgtcgag tactatcgag atgaaggatt ccattaccac caccgtccct    900
tccggcaacg tccggcaaa gccaatccat tcggaaaatc ccagttccag cagcttaacg     960
gaaaatatca gcgcgatcca acaaccatcc catcaaaaac aaagccaaag cttcttaaat   1020
ttctccgatt acggcttcga atcaaatccc tcaaagaaca ccaccgcggc cgcaacaacc   1080
accaccgcca cccatcatt caagccggaa tccggcggga tgctgaattt cggcaacgga    1140
aacctcttct ctagccattc acagtatgta acaaacgaac agaacgagaa aaagagatcc    1200
cctgcttctc ggagtagcaa cgacgaaggg atcctctctt tcacctctgg cgtgatctta    1260
ccctcctccg gtaaggtaaa atccggggac tcagaccact cagatctcga agcatcggtg    1320
```

-continued

```
atcagagaag tggatagctg tacaaaatca ttagaacccg aaaaacgtcc aagaaaaaga    1380
ggtagaaaac cagcaaacgg aagagaagag ccattgaatc atgtagaagc agagagacaa    1440
cggcgagaga agttgaacca gaaattctac gctctccgag ctgtagttcc aaacgtatct    1500
aaaatggaca aggcctcact actgggagac gcggtttctt acatcaacga gctcaaatca    1560
aagctccaaa tagcggaaac ggagaaaaca gagatgggaa acatttaga attgctgaag    1620 aaggagatgg gagggaaaga tttcgggaat tacccgaacc caaatgatga agatctgaaa    1680
ataggaaaaa gaaaggtaat ggatatggag atcgaagtta aaatcatggg ttgggatgcg    1740
atgataagga ttcaaagcag caagaaaaat catccggcgg caaggctgat ggcggcgttt    1800
aaggatttag atttagaaat gcttcatgcg agtgtttctg tagtgaatga tttgatgatt    1860
caacaggcaa cggtgaagat ggggagcaga ttttacacac aggagcagct taaaatggct    1920
ctcgtcgccc gagtcggggg cggcggcggc agcagccatg gaatgatgta a            1971
```

<210> SEQ ID NO 20
<211> LENGTH: 656
<212> TYPE: PRT
<213> ORGANISM: Citrullus lanatus

<400> SEQUENCE: 20

```
Met Thr Asp Tyr Arg Leu Ser Thr Met Asn Leu Trp Thr Asp Glu Asn
1               5                   10                  15

Ala Ser Val Met Asp Ala Phe Met Asn Ser Asp Leu Ser Ser Tyr Trp
                20                  25                  30

Ala Pro Ser Ala Ala Ser Ser His Ser Leu His His Pro Pro Pro
            35                  40                  45

Gln Ser Ser Ala Ser Thr Ser Thr Pro Pro Pro Asp Pro Pro Lys Ser
        50                  55                  60

Leu Pro Val Phe Asn Gln Glu Thr Leu Gln Gln Arg Leu Gln Ala Leu
65                  70                  75                  80

Ile Asp Gly Ala Arg Glu Ser Trp Thr Tyr Ala Ile Phe Trp Gln Ser
                85                  90                  95

Ser Tyr Asp Tyr Ser Gly Ala Ser Val Leu Gly Trp Gly Asp Gly Tyr
                100                 105                 110

Tyr Lys Gly Glu Glu Asp Lys Gly Lys Gly Lys Ala Lys Met Val Ser
            115                 120                 125

Ser Ala Ala Glu Gln Ala His Arg Lys Lys Val Leu Arg Glu Leu Asn
        130                 135                 140

Ser Leu Ile Ser Gly Ser Ala Ala Gly Pro Asp Asp Ala Val Asp Glu
145                 150                 155                 160

Glu Val Thr Asp Thr Glu Trp Phe Phe Leu Val Ser Met Thr Gln Ser
                165                 170                 175

Phe Asp Asn Gly Val Trp Leu Pro Ser Gln Ala Phe Tyr Asn Ser Thr
                180                 185                 190

Pro Ile Trp Val Ser Gly Ala Asp Arg Leu Ser Ala Ser Ala Cys Glu
            195                 200                 205

Arg Ala Arg Gln Gly Arg Val Phe Gly Leu Gln Thr Met Val Cys Ile
        210                 215                 220

Pro Ser Pro Asn Gly Val Val Glu Met Gly Ser Thr Glu Leu Ile His
225                 230                 235                 240

Arg Thr Ser Asp Leu Met Asn Lys Val Lys Ile Leu Phe Asn Phe Asn
                245                 250                 255

Asn Leu Glu Thr Ser Ser Trp Ile Ser Gly Thr Thr Ala Ala Asp Glu
```

```
                260                 265                 270
Gly Glu Asn Asp Pro Ser Ser Met Trp Ile Ser Glu Pro Ser Ser Thr
            275                 280                 285
Ile Glu Met Lys Asp Ser Ile Thr Thr Thr Val Pro Ser Gly Asn Val
290                 295                 300
Pro Ala Lys Pro Ile His Ser Glu Asn Pro Ser Ser Ser Ser Leu Thr
305                 310                 315                 320
Glu Asn Ile Ser Ala Ile Gln Gln Pro Ser His Gln Lys Gln Ser Gln
                325                 330                 335
Ser Phe Leu Asn Phe Ser Asp Tyr Gly Phe Glu Ser Asn Pro Ser Lys
            340                 345                 350
Asn Thr Thr Ala Ala Ala Thr Thr Thr Thr Ala Thr Pro Ser Phe Lys
            355                 360                 365
Pro Glu Ser Gly Gly Met Leu Asn Phe Gly Asn Gly Asn Leu Phe Ser
        370                 375                 380
Ser His Ser Gln Tyr Val Thr Asn Glu Gln Asn Glu Lys Lys Arg Ser
385                 390                 395                 400
Pro Ala Ser Arg Ser Ser Asn Asp Glu Gly Ile Leu Ser Phe Thr Ser
                405                 410                 415
Gly Val Ile Leu Pro Ser Ser Gly Lys Val Lys Ser Gly Asp Ser Asp
            420                 425                 430
His Ser Asp Leu Glu Ala Ser Val Ile Arg Glu Val Asp Ser Cys Thr
            435                 440                 445
Lys Ser Leu Glu Pro Glu Lys Arg Pro Arg Lys Arg Gly Arg Lys Pro
        450                 455                 460
Ala Asn Gly Arg Glu Glu Pro Leu Asn His Val Glu Ala Glu Arg Gln
465                 470                 475                 480
Arg Arg Glu Lys Leu Asn Gln Lys Phe Tyr Ala Leu Arg Ala Val Val
                485                 490                 495
Pro Asn Val Ser Lys Met Asp Lys Ala Ser Leu Leu Gly Asp Ala Val
            500                 505                 510
Ser Tyr Ile Asn Glu Leu Lys Ser Lys Leu Gln Ile Ala Glu Thr Glu
            515                 520                 525
Lys Thr Glu Met Gly Lys His Leu Glu Leu Leu Lys Lys Glu Met Gly
        530                 535                 540
Gly Lys Asp Phe Gly Asn Tyr Pro Asn Pro Asn Asp Glu Asp Leu Lys
545                 550                 555                 560
Ile Gly Lys Arg Lys Val Met Asp Met Glu Ile Glu Val Lys Ile Met
                565                 570                 575
Gly Trp Asp Ala Met Ile Arg Ile Gln Ser Ser Lys Lys Asn His Pro
            580                 585                 590
Ala Ala Arg Leu Met Ala Ala Phe Lys Asp Leu Asp Leu Glu Met Leu
            595                 600                 605
His Ala Ser Val Ser Val Val Asn Asp Leu Met Ile Gln Gln Ala Thr
        610                 615                 620
Val Lys Met Gly Ser Arg Phe Tyr Thr Gln Glu Gln Leu Lys Met Ala
625                 630                 635                 640
Leu Val Ala Arg Val Gly Gly Gly Gly Ser Ser His Gly Met Met
                645                 650                 655
```